(12) United States Patent
Rajeev et al.

(10) Patent No.: US 9,290,760 B2
(45) Date of Patent: Mar. 22, 2016

(54) MODIFIED IRNA AGENTS

(75) Inventors: Kallanthottathil G. Rajeev, Cambridge, MA (US); Tracy Zimmermann, Cambridge, MA (US); Muthiah Manoharan, Cambridge, MA (US); Martin Maier, Cambridge, MA (US); Kevin Fitzgerald, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 32 days.

(21) Appl. No.: 13/822,441

(22) PCT Filed: Sep. 14, 2011

(86) PCT No.: PCT/US2011/051597
§ 371 (c)(1),
(2), (4) Date: Jun. 27, 2013

(87) PCT Pub. No.: WO2012/037254
PCT Pub. Date: Mar. 22, 2012

(65) Prior Publication Data
US 2013/0317080 A1 Nov. 28, 2013

Related U.S. Application Data

(60) Provisional application No. 61/383,250, filed on Sep. 15, 2010.

(51) Int. Cl.
*C12N 15/113* (2010.01)
*C12N 15/11* (2006.01)

(52) U.S. Cl.
CPC ............ *C12N 15/113* (2013.01); *C12N 15/111* (2013.01); *C12N 2310/14* (2013.01); *C12N 2310/315* (2013.01); *C12N 2310/322* (2013.01); *C12N 2310/343* (2013.01); *C12N 2310/346* (2013.01); *C12N 2310/351* (2013.01); *C12N 2310/3515* (2013.01); *C12N 2320/32* (2013.01); *C12N 2320/52* (2013.01)

(58) Field of Classification Search
None
See application file for complete search history.

(56) References Cited

U.S. PATENT DOCUMENTS

2006/0094032 A1* 5/2006 Fougerolles et al. ............. 435/6

FOREIGN PATENT DOCUMENTS

| WO | 2004015107 A2 | 2/2004 |
|---|---|---|
| WO | 2004044136 A2 | 5/2004 |
| WO | 2009073809 A2 | 6/2009 |
| WO | 2009126933 A2 | 10/2009 |
| WO | 2009134487 A2 | 11/2009 |
| WO | 2009142822 A2 | 11/2009 |
| WO | 2010148013 A2 | 12/2010 |

\* cited by examiner

*Primary Examiner* — Tracy Vivlemore
(74) *Attorney, Agent, or Firm* — Jeffrey N. Townes; LeClairRyan

(57) ABSTRACT

The present invention provides effective motifs for RNA agents conjugated to at least one ligand, which are advantageous for the in vivo delivery of iRNA duplex agents. Additionally, the present invention provides methods of making these compositions, as well as methods of introducing these iRNA duplex agents into cells using these compositions, e.g., for the treatment of various disease conditions.

33 Claims, 5 Drawing Sheets

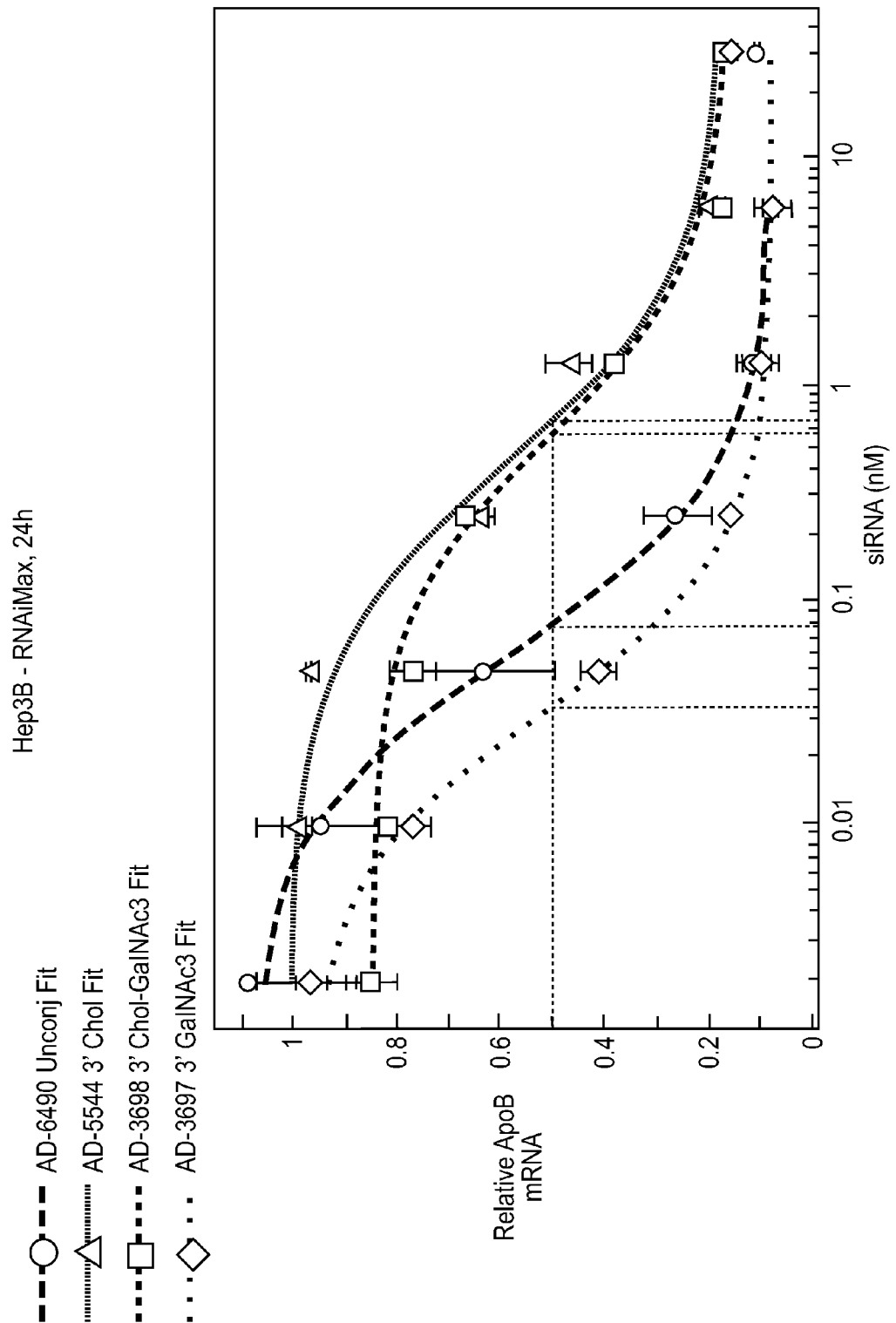

SEQUENCE LISTING

```
<160> NUMBER OF SEQ ID NOS: 32

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Ala Leu Ala
1

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25
```

```
<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Glu Ala Leu Ala Glu Ala Leu Glu Ala Leu Ala Glu Ala
1               5                   10                  15

<210> SEQ ID NO 5
<211> LENGTH: 16
<212> TYPE: PRT
<213> ORGANISM: Drosophila sp.

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 14
<212> TYPE: PRT
<213> ORGANISM: Human immunodeficiency virus

<400> SEQUENCE: 6

Gly Arg Lys Lys Arg Arg Gln Arg Arg Arg Pro Pro Gln Cys
1               5                   10

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Leu Leu Ile Ile Leu Arg Arg Arg Ile Arg Lys Gln Ala His Ala His
1               5                   10                  15

Ser Lys

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Arg Arg Arg Arg Arg Arg Arg
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Phe Phe Lys Phe Phe Lys Phe Phe Lys
1               5                   10

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 13

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
                35

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
                35

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Lys Cys Arg Ile Val Val Ile Arg Val Cys Arg
1               5                   10
```

```
<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro Gly Lys Arg
        35                  40

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Leu Pro Trp Lys Trp Pro Trp Trp Pro Trp Arg Arg
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Val Ala Leu Leu Pro Ala Val Leu Leu Ala Leu Leu Ala Pro
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Leu Leu Pro Val Leu Leu Ala Ala Pro
1               5                   10

<210> SEQ ID NO 22
<211> LENGTH: 13
<212> TYPE: PRT
<213> ORGANISM: Human immunodeficiency virus

<400> SEQUENCE: 22

Gly Arg Lys Lys Arg Arg Gln Arg Arg Pro Pro Gln
1               5                   10

<210> SEQ ID NO 23
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
gccuggaguu uauucggaat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
uuccgaauaa acuccaggct t                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaaucuuau auuugaucca a                                              21

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uuggaucaaa uauaagauuc ccu                                            23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ggaucaucuc aagucuuact t                                              21

<210> SEQ ID NO 28
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
guaagacuug agaugaucct t                                              21

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uuggaucaaa uauaagauuc caa                                            23

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
gaugauguuu gaaacuauut t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
aauaguuuca aacaucauct t                                              21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
aauaguuuca aacaucauct tg                                             22
```

MODIFIED IRNA AGENTS

PRIORITY CLAIM

This application claims priority to PCT Application No. PCT/US2011/051597, filed Sep. 14, 2011, which claims priority of U.S. Provisional Application No. 61/383,250, filed Sep. 15, 2010, both of which are incorporated herein by reference in their entirety.

FIELD OF INVENTION

The present invention provides effective motifs for RNA agents conjugated to at least one ligand, which are advantageous for the in vivo delivery of these iRNA duplex agents, as well as iRNA compositions suitable for in vivo therapeutic use. Additionally, the present invention provides methods of making these compositions, as well as methods of introducing these iRNA duplex agents into cells using these compositions, e.g., for the treatment of various disease conditions.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

RNA interference or "RNAi" is a term initially coined by Fire and co-workers to describe the observation that double-stranded RNA (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

siRNA has been shown to be extremely effective as a potential anti-viral therapeutic with numerous published examples appearing recently. siRNA molecules directed against targets in the viral genome dramatically reduce viral titers by orders of magnitude in animal models of influenza (Ge et al., (2004) *Proc. Natl. Acad. Sci. USA*, 101, 8676-8681; Tompkins et al. (2004) *Proc. Natl. Acad. Sci. USA*, 101, 8682-8686; Thomas et al. (2005) *Expert Opin. Biol. Ther.* 5, 495-505), respiratory synctial virus (RSV) (Bitko et al. (2005) *Nat. Med.* 11, 50-55), hepatitis B virus (HBV) (Morrissey et al. (2005) *Nat. Biotechnol.* 23, 1002-1007), hepatitis C virus (Kapadia et al. (2003) *Proc. Natl. Acad. Sci. USA*, 100, 2014-2018; Wilson et al. (2003) *Proc. Natl. Acad. Sci. USA*, 100, 2783-2788) and SARS coronavirus (Li et al. (2005) *Nat. Med.* 11, 944-951).

Efficient delivery to cells in vivo requires specific targeting and substantial protection from the extracellular environment, particularly serum proteins. One method of achieving specific targeting is to conjugate a targeting moiety to the iRNA duplex agent. The targeting moiety helps in targeting the iRNA duplex agent to the required target site. One way a targeting moiety can improve delivery is by receptor mediated endocytotic activity. This mechanism of uptake involves the movement of iRNA duplex agent bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal. Previous work has shown that multivalency is required to achieve nM affinity, while spacing among sugars is also crucial. While there are few successes with the use of targeting ligand, however such successes do not always stranslate to in vivo setting. Not withstanding the successes so far, there is a clear need for more efficacous receptor specific ligand conjugated iRNA duplex agents and methods for their preparation, that address the shortcomings of the in vivo delivery of oligonucleotide therapeutics as described above. The present invention is directed to this very important end.

SUMMARY

The present invention provides effective motifs for RNA agents conjugated to at least one ligand, which are advantageous for the in vivo delivery of iRNA duplex agents, as well as iRNA compositions suitable for in vivo therapeutic use.

In one aspect, the invention provides effective motifs for iRNA duplex agent that is conjugated with at least one carbohydrate ligand, e.g., monosaccharide, disaccharide, trisaccharide, tetrasaccharide, oligosaccharide, polysaccharide. These carbohydrate-conjugated iRNA duplex agents target, in particular, the parenchymal cells of the liver. In one embodiment, the iRNA duplex agent includes more than one carbohydrate ligand, preferably two or three. In one embodiment, the iRNA duplex agent comprises one or more galactose moiety. In another embodiment, the iRNA duplex agent includes at least one (e.g., two or three or more) lactose molecules (lactose is a glucose coupled to a galactose). In another embodiment, the iRNA duplex agent includes at least one (e.g., two or three or more) N-Acetyl-Galactosamine (GalNAc), N—Ac-Glucosamine (GluNAc), or mannose (e.g., mannose-6-phosphate). In one embodiment, iRNA duplex agent comprises at least one mannose ligand, and the iRNA duplex agent targets macrophages.

In one aspect, the invention features an iRNA duplex agent comprising a carbohydrate ligand, and the presence of the carbohydrate ligand can increase delivery of the iRNA duplex agent to the liver. Thus an iRNA duplex agent comprising a carbohydrate ligand can be useful for targeting a gene for which expression is undesired in the liver. For example, an iRNA duplex agent comprising a carbohydrate ligand can target a nucleic acid expresses by a hepatitis virus (e.g., hepatitis C, hepatitis B, hepatitis A, hepatitis D, hepatitis E, hepatitis F, hepatitis G, or hepatitis H).

In one aspect, the invention further provides a method for delivering a polynucleotide to specific target in a subject subcutaneously.

DETAILED DESCRIPTION

Figure 1A:
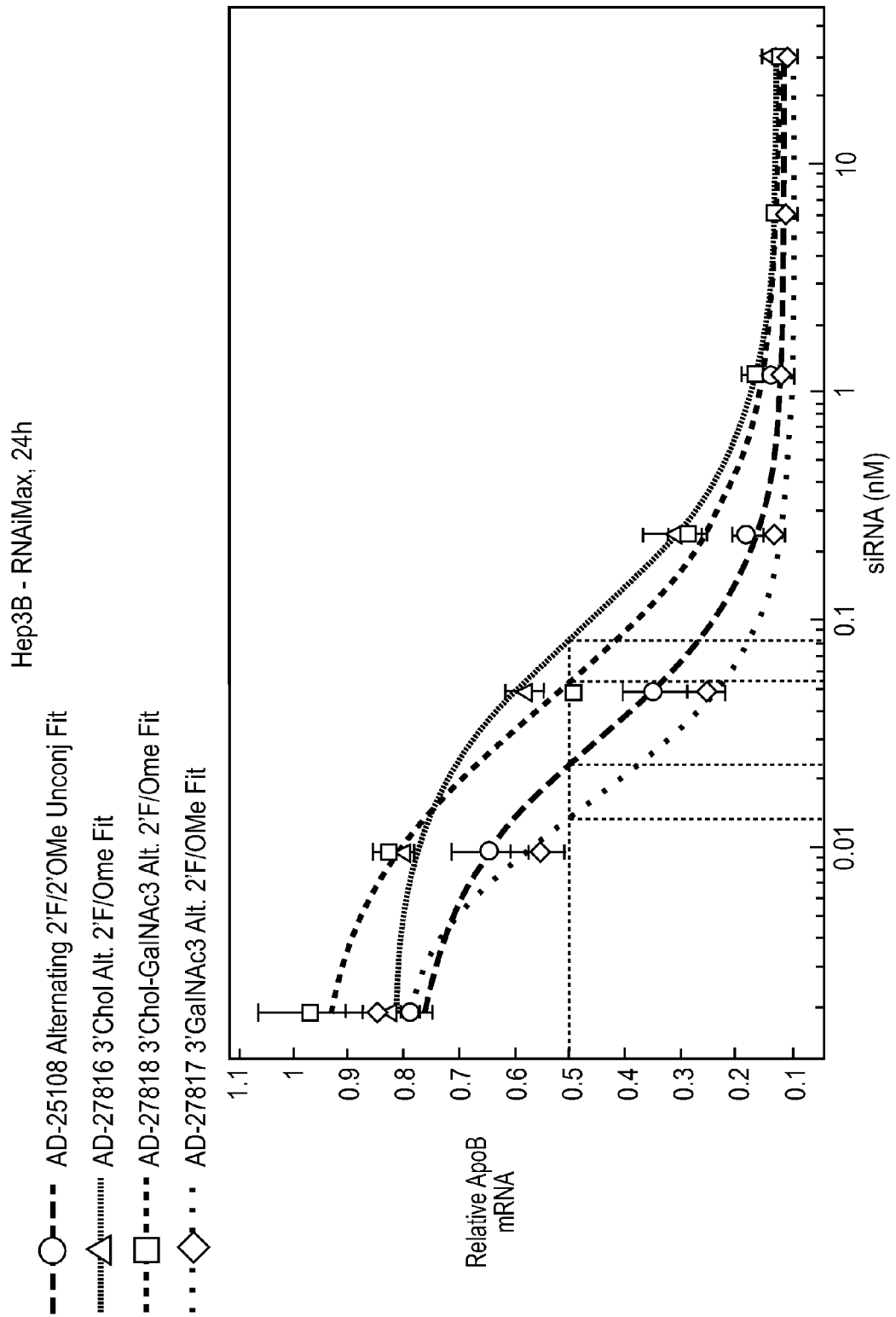
FIG. 1. In vitro silencing of ApoB siRNAs containing chemically modified motifs in combination with various conjugates.

This invention is based on the superior result obtained by combining an alternating motif of the duplex region in an siRNA in combination with a GalNAc3 containing ligand. Particularly said siRNA were effectively delivered to the target site in a subject by subcutaneous or intravenous administration.

In one aspect, the invention provides an iRNA duplex agent capable of silencing a target gene in vivo, comprising:
(a) a sense strand, wherein said sense strand comprises
    (i) an alternating motif with at least 2 different chemically modified nucleotides;
    (ii) at least one ligand; and
(b) an antisense strand, wherein said antisense strand comprises
    (i) an alternating motif with at least 2 different chemically modified nucleotides; and
    wherein the alternating motif is within the duplex region and the composition optionally further comprises one or more overhangs and/or capping groups.

In one embodiment, the iRNA duplex agent of the invention further comprising at least one phosphorothioate internucleotide linkage; or at least one methylphosphonate internucleoside linkage.

In one embodiment, the iRNA duplex agent of the invention comprising a chemically modified nucleotide is selected from the group consisting of LNA, HNA, CeNA, 2'-methoxyethyl, 2'-OCH$_3$, 2'-O-allyl, 2'-C-allyl, and 2'-fluoro.

In one embodiment, the iRNA duplex agent of the invention comprising an overhang, wherein the overhang comprises at least 2 nucleotides in length and is selected from the group consisting of thymidine (T), 2'-O-methoxyethyl-5-methyluridine (Teo), 2'-O-methoxyethyladenosine (Aeo), 2'-O-methoxyethyl-5-methylcytidine (m5Ceo), and combinations thereof, and optionally comprising a phosphorothioate between the two nucleotides, wherein the 2 nucleotides can be the same or different. The overhang can form a mismatch with the target mRNA or it can fully complement with the target mRNA.

In one embodiment, the ligand is attached to the 3' end of the sense strand.

In one embodiment, the iRNA duplex agent further comprises differential modification of the terminal duplex stability (DMTDS).

Differential Modification of Terminal Duplex Stability (DMTDS)

In addition, the invention includes iRNA agents having DMTDS and another element described herein. E.g., the invention includes an iRNA agent described herein, e.g., a palindromic iRNA agent, an iRNA agent having a non canonical pairing, an iRNA agent which targets a gene described herein, e.g., a gene active in the liver, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates DMTDS.

iRNA agents can be optimized by increasing the propensity of the duplex to disassociate or melt (decreasing the free energy of duplex association), in the region of the 5' end of the antisense strand duplex. This can be accomplished, e.g., by the inclusion of subunits which increase the propensity of the duplex to disassociate or melt in the region of the 5' end of the antisense strand. It can also be accomplished by the attachment of a ligand that increases the propensity of the duplex to disassociate of melt in the region of the 5' end. While not wishing to be bound by theory, the effect may be due to promoting the effect of an enzyme such as helicase, for example, promoting the effect of the enzyme in the proximity of the 5' end of the antisense strand.

The inventors have also discovered that iRNA agents can be optimized by decreasing the propensity of the duplex to disassociate or melt (increasing the free energy of duplex association), in the region of the 3' end of the antisense strand duplex. This can be accomplished, e.g., by the inclusion of subunits which decrease the propensity of the duplex to disassociate or melt in the region of the 3' end of the antisense strand. It can also be accomplished by the attachment of ligand that decreases the propensity of the duplex to disassociate of melt in the region of the 5' end.

Modifications which increase the tendency of the 5' end of the duplex to dissociate can be used alone or in combination with other modifications described herein, e.g., with modifications which decrease the tendency of the 3' end of the duplex to dissociate. Likewise, modifications which decrease the tendency of the 3' end of the duplex to dissociate can be used alone or in combination with other modifications described herein, e.g., with modifications which increase the tendency of the 5' end of the duplex to dissociate.

Decreasing the Stability of the AS 5' End of the Duplex

Subunit pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation:
  A:U is preferred over G:C;
  G:U is preferred over G:C;
  I:C is preferred over G:C (I=inosine);
  mismatches, e.g., non-canonical or other than canonical pairings (as described elsewhere herein) are preferred over canonical (A:T, A:U, G:C) pairings;
  pairings which include a universal base are preferred over canonical pairings.

A typical ds iRNA agent can be diagrammed as follows:

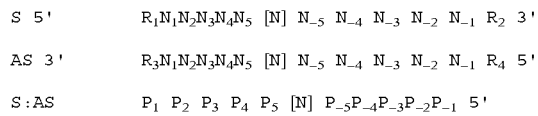

```
S    5'      R₁N₁N₂N₃N₄N₅ [N] N₋₅ N₋₄ N₋₃ N₋₂ N₋₁ R₂ 3'
AS   3'      R₃N₁N₂N₃N₄N₅ [N] N₋₅ N₋₄ N₋₃ N₋₂ N₋₁ R₄ 5'
S:AS         P₁ P₂ P₃ P₄ P₅ [N] P₋₅ P₋₄ P₋₃ P₋₂ P₋₁ 5'
```

S indicates the sense strand; AS indicates antisense strand; $R_1$ indicates an optional (and nonpreferred) 5' sense strand overhang; $R_2$ indicates an optional (though preferred) 3' sense overhang; $R_3$ indicates an optional (though preferred) 3' antisense sense overhang; $R_4$ indicates an optional (and nonpreferred) 5' antisense overhang; N indicates subunits; [N] indicates that additional subunit pairs may be present; and $P_x$, indicates a paring of sense $N_x$ and antisense $N_x$. Overhangs are not shown in the P diagram. In some embodiments a 3' AS overhang corresponds to region Z, the duplex region corresponds to region X, and the 3' S strand overhang corresponds to region Y, as described elsewhere herein. (The diagram is not meant to imply maximum or minimum lengths, on which guidance is provided elsewhere herein.)

It is preferred that pairings which decrease the propensity to form a duplex are used at 1 or more of the positions in the duplex at the 5' end of the AS strand. The terminal pair (the most 5' pair in terms of the AS strand) is designated as $P_{-1}$, and the subsequent pairing positions (going in the 3' direction in terms of the AS strand) in the duplex are designated, $P_{-2}$, $P_{-3}$, $P_{-4}$, $P_{-5}$, and so on. The preferred region in which to modify to modulate duplex formation is at $P_{-5}$ through $P_{-1}$, more preferably $P_{-4}$ through $P_{-1}$, more preferably $P_{-3}$ through $P_{-1}$. Modification at $P_{-1}$, is particularly preferred, alone or with modification(s) other position(s), e.g., any of the positions just identified. It is preferred that at least 1, and more preferably 2, 3, 4, or 5 of the pairs of one of the recited regions be chosen independently from the group of:

A:U
G:U
I:C
mismatched pairs, e.g., non-canonical or other than canonical pairings or pairings which include a universal base.

In preferred embodiments the change in subunit needed to achieve a pairing which promotes dissociation will be made in the sense strand, though in some embodiments the change will be made in the antisense strand.

In a preferred embodiment the at least 2, or 3, of the pairs in $P_{-1}$, through $P_{-4}$, are pairs which promote disociation.

In a preferred embodiment the at least 2, or 3, of the pairs in $P_{-1}$, through $P_{-4}$, are A:U.

In a preferred embodiment the at least 2, or 3, of the pairs in $P_{-1}$, through $P_{-4}$, are G:U.

In a preferred embodiment the at least 2, or 3, of the pairs in $P_{-1}$, through $P_{-4}$, are I:C.

In a preferred embodiment the at least 2, or 3, of the pairs in $P_{-1}$, through $P_{-4}$, are mismatched pairs, e.g., non-canonical or other than canonical pairings pairings.

In a preferred embodiment the at least 2, or 3, of the pairs in $P_{-1}$, through $P_{-4}$, are pairings which include a universal base.

Increasing the Stability of the AS 3' End of the Duplex

Subunit pairs can be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability:

G:C is preferred over A:U
Watson-Crick matches (A:T, A:U, G:C) are preferred over non-canonical or other than canonical pairings
analogs that increase stability are preferred over Watson-Crick matches (A:T, A:U, G:C)
2-amino-A:U is preferred over A:U
2-thio U or 5 Me-thio-U:A are preferred over U:A
G-clamp (an analog of C having 4 hydrogen bonds):G is preferred over C:G
guanadinium-G-clamp:G is preferred over C:G
psuedo uridine:A is preferred over U:A
sugar modifications, e.g., 2' modifications, e.g., 2'F, ENA, or LNA, which enhance binding are preferred over non-modified moieties and can be present on one or both strands to enhance stability of the duplex. It is preferred that pairings which increase the propensity to form a duplex are used at 1 or more of the positions in the duplex at the 3' end of the AS strand. The terminal pair (the most 3' pair in terms of the AS strand) is designated as $P_1$, and the subsequent pairing positions (going in the 5' direction in terms of the AS strand) in the duplex are designated, $P_2$, $P_3$, $P_4$, $P_5$, and so on. The preferred region in which to modify to modulate duplex formation is at $P_5$ through $P_1$, more preferably $P_4$ through $P_1$, more preferably $P_3$ through $P_1$. Modification at $P_1$, is particularly preferred, alone or with mdification(s) at other position(s), e.g., any of the positions just identified. It is preferred that at least 1, and more preferably 2, 3, 4, or 5 of the pairs of the recited regions be chosen independently from the group of:

G:C
a pair having an analog that increases stability over Watson-Crick matches (A:T, A:U, G:C)
2-amino-A:U
2-thio U or 5 Me-thio-U:A
G-clamp (an analog of C having 4 hydrogen bonds):G
guanadinium-G-clamp:G
psuedo uridine:A
a pair in which one or both subunits has a sugar modification, e.g., a 2' modification, e.g., 2'F, ENA, or LNA, which enhance binding.

In a preferred embodiment the at least 2, or 3, of the pairs in $P_{-1}$, through $P_{-4}$, are pairs which promote duplex stability.

In a preferred embodiment the at least 2, or 3, of the pairs in $P_1$, through $P_4$, are G:C.

In a preferred embodiment the at least 2, or 3, of the pairs in $P_1$, through $P_4$, are a pair having an analog that increases stability over Watson-Crick matches.

In a preferred embodiment the at least 2, or 3, of the pairs in $P_1$, through $P_4$, are 2-amino-A:U.

In a preferred embodiment the at least 2, or 3, of the pairs in $P_1$, through $P_4$, are 2-thio U or 5 Me-thio-U:A.

In a preferred embodiment the at least 2, or 3, of the pairs in $P_1$, through $P_4$, are G-clamp:G.

In a preferred embodiment the at least 2, or 3, of the pairs in $P_1$, through $P_4$, are guanidinium-G-clamp:G.

In a preferred embodiment the at least 2, or 3, of the pairs in $P_1$, through $P_4$, are psuedo uridine:A.

In a preferred embodiment the at least 2, or 3, of the pairs in $P_1$, through $P_4$, are a pair in which one or both subunits has a sugar modification, e.g., a 2' modification, e.g., 2'F, ENA, or LNA, which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003;

Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

Simultaneously Decreasing the Stability of the AS 5' End of the Duplex and Increasing the Stability of the AS 3' End of the Duplex As is discussed above, an iRNA agent can be modified to both decrease the stability of the AS 5' end of the duplex and increase the stability of the AS 3' end of the duplex. This can be effected by combining one or more of the stability decreasing modifications in the AS 5' end of the duplex with one or more of the stability increasing modifications in the AS 3' end of the duplex. Accordingly a preferred embodiment includes modification in $P_{-5}$ through $P_{-1}$, more preferably $P_{-4}$ through $P_{-1}$ and more preferably $P_{-3}$ through $P_{-1}$. Modification at $P_{-1}$, is particularly preferred, alone or with other position, e.g., the positions just identified. It is preferred that at least 1, and more preferably 2, 3, 4, or 5 of the pairs of one of the recited regions of the AS 5' end of the duplex region be chosen independently from the group of:

A:U
G:U
I:C
mismatched pairs, e.g., non-canonical or other than canonical pairings which include a universal base; and
a modification in $P_5$ through $P_1$, more preferably $P_4$ through $P_1$ and more preferably $P_3$ through $P_1$. Modification at $P_1$, is particularly preferred, alone or with other position, e.g., the positions just identified. It is preferred that at least 1, and more preferably 2, 3, 4, or 5 of the pairs of one of the recited regions of the AS 3' end of the duplex region be chosen independently from the group of:

G:C
a pair having an analog that increases stability over Watson-Crick matches (A:T, A:U, G:C)
2-amino-A:U
2-thio U or 5 Me-thio-U:A
G-clamp (an analog of C having 4 hydrogen bonds):G
guanadinium-G-clamp:G
psuedo uridine:A
a pair in which one or both subunits has a sugar modification, e.g., a 2' modification, e.g., 2'F, ENA, or LNA, which enhance binding.

The invention also includes methods of selecting and making iRNA agents having DMTDS. E.g., when screening a target sequence for candidate sequences for use as iRNA agents one can select sequences having a DMTDS property described herein or one which can be modified, preferably with as few changes as possible, especially to the AS strand, to provide a desired level of DMTDS.

The invention also includes, providing a candidate iRNA agent sequence, and modifying at least one P in $P_{-5}$ through $P_{-1}$ and/or at least one P in $P_5$ through $P_1$ to provide a DMTDS iRNA agent.

DMTDS iRNA agents can be used in any method described herein, e.g., to silence any gene disclosed herein, to treat any disorder described herein, in any formulation described herein, and generally in and/or with the methods and compositions described elsewhere herein. DMTDS iRNA agents can incorporate other modifications described herein, e.g., the attachment of targeting agents or the inclusion of modifications which enhance stability, e.g., the inclusion of nuclease resistant monomers or the inclusion of single strand overhangs (e.g., 3' AS overhangs and/or 3' S strand overhangs) which self associate to form intrastrand duplex structure.

In one aspect, the invention provides a method for delivering polynucleotide to specific target in a subject by administering said iRNA duplex agent comprising:
(a) a sense strand, wherein said sense strand comprises
(i) an alternating motif with at least 2 different chemically modified nucleotides;
(ii) at least one ligand; and
(b) an antisense strand, wherein said antisense strand comprises
(i) an alternating motif with at least 2 different chemically modified nucleotides.

In one embodiment, the delivery of the iRNA duplex agent of the invention is carried out by an administration means comprising intramuscular, intrabronchial, intrapleural, intraperitoneal, intraarterial, lymphatic, intravenous, subcutaneous, cerebrospinal, or combinations thereof.

In one aspect, the invention provides a method for delivering a polynucleotide to specific target of a subject, the method comprising: delivering an iRNA duplex agent of the invention subcutaneously into the subject, such that the polynucleotide is delivered into specific target of the subject.

In one aspect, the invention provides a pharmaceutical composition comprising an iRNA duplex agent of any claim above alone or in combination with a pharmaceutically acceptable carrier or excipient.

In one aspect the duplex that conjugation of a carbohydrate moiety to an iRNA duplex agent can optimize one or more properties of the iRNA duplex agent. In many cases, the carbohydrate moiety will be attached to a modified subunit of the iRNA duplex agent. E.g., the ribose sugar of one or more ribonucleotide subunits of an iRNA duplex agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

In one embodiment, the ligand is attached to the polynucleotide via a carrier. The carriers include (i) at least one "backbone attachment point", preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one aspect, the invention features, a compound having the structure shown in formula (CI)

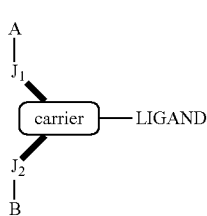

(CI)

A and B are independently for each occurrence hydrogen, protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, or —P($Z^1$)($Z^2$)—O-oligonucleotide; wherein $Z^1$ and $Z^2$ are each independently for each occurrence O, S, N(alkyl) or optionally substituted alkyl; wherein the oligonucleotide comprises (a) a sense strand, wherein said sense strand comprises
  (i) alternating 2'-fluoro modification
  (ii) at least one ligand; and
(b) an antisense strand, wherein said antisense strand comprises
  (i) an alternating 2'-halogen modification; and
  (ii) a first 5' terminal antisense nucleotide, wherein said first 5' terminal antisense nucleotide is phosphorylated at its 5' carbon position.

$J_1$ and $J_2$ are independently O, S, NR$^N$, optionally substituted alkyl, OC(O)NH, NHC(O)O, C(O)NH, NHC(O), OC(O), C(O)O, OC(O)O, NHC(O)NH, NHC(S)NH, OC(S)NH, OP(N(R$^P$)$_2$)O, or OP(N(R$^P$)$_2$); and ⟨carrier⟩ is cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In preferred embodiments, ligand is a carbohydrate e.g. monosaccharide, disaccharide, trisaccharide, tetrasaccharide, polysaccharide.

In one embodiment, the compound is a pyrroline ring system as shown in formula (CII)

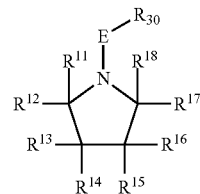

Formula (CII)

wherein E is absent or C(O), C(O)O, C(O)NH, C(S), C(S)NH, SO, SO$_2$, or SO$_2$NH;

$R^{11}$, $R^{12}$, $R^{13}$, $R^{14}$, $R^{15}$, $R^{16}$, $R^{17}$, and $R^{18}$ are each independently for each occurrence H, —CH$_2$OR$^a$, or OR$^b$, $R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^1$)($Z^2$)—O-oligonucleotide, —P($Z^1$)(O-linker-R$^L$)—O-nucleoside, or —P($Z^1$)(O-linker-R$^L$)—O-oligonucleotide; wherein the oligonucleotide comprises (a) a sense strand, wherein said sense strand comprises
  (i) alternating 2'-fluoro modification
  (ii) at least one ligand; and
(b) an antisense strand, wherein said antisense strand comprises
  (i) an alternating 2'-halogen modification; and
  (ii) a first 5' terminal antisense nucleotide, wherein said first 5' terminal antisense nucleotide is phosphorylated at its 5' carbon position.

$R^{30}$ is independently for each occurrence -linker-R$^L$ or R$^{31}$;
$R^L$ is hydrogen or a ligand;
$R^{31}$ is —C(O)CH(N(R$^{32}$)$_2$)(CH$_2$)$_h$N(R$^{32}$)$_2$;
$R^{32}$ is independently for each occurrence H, —R$^L$, -linker-R$^L$ or R$^{31}$;
$Z^1$ is independently for each occurrence O or S;
$Z^2$ is independently for each occurrence O, S, N(alkyl) or optionally substituted alkyl; and
h is independently for each occurrence 1-20.

For the pyrroline-based click-carriers, $R^{11}$ is —CH$_2$OR$^a$ and $R^3$ is OR$^b$; or $R^{11}$ is —CH$_2$OR$^a$ and $R^9$ is OR$^b$; or $R^{11}$ is —CH$_2$OR$^a$ and $R^{17}$ is OR$^b$; or $R^{13}$ is —CH$_2$OR$^a$ and $R^{11}$ is OR$^b$; or $R^{13}$ is —CH$_2$OR$^a$ and $R^{15}$ is OR$^b$; or $R^{13}$ is —CH$_2$OR$^a$ and $R^{17}$ is OR$^b$. In certain embodiments, CH$_2$OR$^a$ and OR$^b$ may be geminally substituted. For the 4-hydroxyproline-based carriers, $R^{11}$ is —CH$_2$OR and $R^{17}$ is OR$^b$. The pyrroline- and 4-hydroxyproline-based compounds may therefore contain linkages (e.g., carbon-carbon bonds) wherein bond rotation is restricted about that particular linkage, e.g. restriction resulting from the presence of a ring. Thus, CH$_2$OR$^a$ and OR$^b$ may be cis or trans with respect to one another in any of the pairings delineated above Accordingly, all cis/trans isomers are expressly included. The compounds may also contain one or more asymmetric centers and thus occur as racemates and racemic mixtures, single enantiomers, individual diastereomers and diastereomeric mixtures. All such isomeric forms of the compounds are expressly included (e.g., the centers bearing CH$_2$OR$^a$ and OR$^b$ can both have the R configuration; or both have the S configuration; or one center can have the R configuration and the other center can have the S configuration and vice versa).

In one embodiment, $R^{11}$ is $CH_2OR^a$ and $R^9$ is $OR^b$.

In one embodiment, $R^b$ is a solid support.

In one embodiment, carrier of formula (CII) is a phosphoramidite, i.e., one of $R^a$ or $R^b$ is —P(O-alkyl)N(alkyl)$_2$, e.g., —P(OCH$_2$CH$_2$CN)N(i-propyl)$_2$. In one embodiment, $R^b$ is —P(O-alkyl)N(alkyl)$_2$.

In embodiment, the compound is a ribose ring system as shown in formula (CIII).

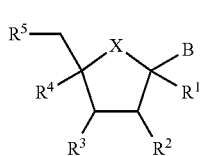

Formula (CIII)

wherein:

X is O, S, NR$^N$ or CR$^P$2;

B is independently for each occurrence hydrogen, optionally substituted natural or non-natural nucleobase, optionally substituted natural nucleobase conjugated with -linker-R$^L$ or optionally substituted non-natural nucleobase conjugated with -linker-R$^L$;

$R^1$, $R^2$, $R^3$, $R^4$ and $R^5$ are each independently for each occurrence H, OR$^6$, F, N(R$^N$)$_2$, or -J-linker-R$_L$;

J is absent, O, S, NR$^N$, OC(O)NH, NHC(O)O, C(O)NH, NHC(O), NHSO, NHSO$_2$, NHSO$_2$NH, OC(O), C(O)O, OC(O)O, NHC(O)NH, NHC(S)NH, OC(S)NH, OP(N(R$^P$)$_2$)O, or OP(N(RP)$_2$);

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(Z$^2$)-formula (CIII), —P(Z$^1$)(O-linker-R$^L$)—O-nucleoside, —P(Z$^1$)(O-linker-R$^L$)—O-oligonucleotide, or —P(Z$^1$)(O-linker-R$^L$)—O-formula (CIII); wherein the oligonucleotide comprises (a) a sense strand, wherein said sense strand comprises
(i) alternating 2'-fluoro modification
(ii) at least one ligand; and
(b) an antisense strand, wherein said antisense strand comprises
(i) an alternating 2'-halogen modification; and
(ii) a first 5' terminal antisense nucleotide, wherein said first 5' terminal antisense nucleotide is phosphorylated at its 5' carbon position.

R$^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

R$^P$ is independently for each occurrence occurrence H, optionally substituted alkyl, optionally substituted alkenyl, optionally substituted alkynyl, optionally substituted aryl, optionally substituted cycloalkyl or optionally substituted heteroaryl;

R$^L$ is hydrogen or a ligand;

$Z^1$ and $Z^2$ are each independently for each occurrence O, S N(alkyl) or optionally substituted alkyl; and provided that R$^L$ is present at least once and further provided that R$^L$ is a ligand at least once.

In one embodiment, the carrier of formula (CI) is an acyclic group and is termed an "acyclic carrier". Preferred acyclic carriers can have the structure shown in formula (CIV) or formula (CV) below.

In one embodiment, the compound is an acyclic carrier having the structure shown in formula (CIV).

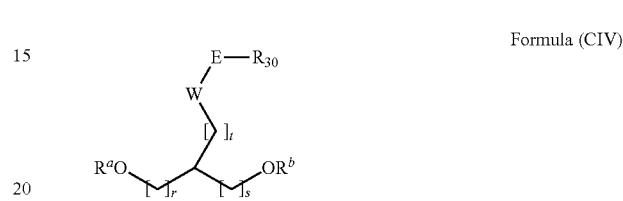

Formula (CIV)

wherein:

W is absent, O, S and N(R$^N$), where R$^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, SO$_2$, or SO$_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(O-linker-R$^L$)—O-nucleoside, or —P(Z$^1$)(O-linker-R$^L$)—O-oligonucleotide; wherein the oligonucleotide comprises (a) a sense strand, wherein said sense strand comprises
(i) alternating 2'-fluoro modification
(ii) at least one ligand; and
(b) an antisense strand, wherein said antisense strand comprises
(i) an alternating 2'-halogen modification; and
(ii) a first 5' terminal antisense nucleotide, wherein said first 5' terminal antisense nucleotide is phosphorylated at its 5' carbon position.

R$^{30}$ is independently for each occurrence -linker-R$^L$ or R$^{31}$;

R$^L$ is hydrogen or a ligand;

R$^{31}$ is —C(O)CH(N(R$^{32}$)$_2$)(CH$_2$)$_h$N(R$^{32}$)$_2$;

R$^{32}$ is independently for each occurrence H, —R$^L$, -linker-R$^L$ or R$^{31}$;

$Z^1$ is independently for each occurrence O or S;

$Z^2$ is independently for each occurrence O, S, N(alkyl) or optionally substituted alkyl;

h is independently for each occurrence 1-20; and r, s and t are each independently for each occurrence 0, 1, 2 or 3.

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

In one embodiment, the compound is an acyclic carrier having the structure shown in formula (CV)

Formula (CV)

wherein E is absent or C(O), C(O)O, C(O)NH, C(S), C(S)NH, SO, SO$_2$, or SO$_2$NH;

R$^a$ and R$^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(Z$^2$)-formula (I), —P(Z$^1$)(O-linker-R$^L$)—O-nucleoside, or —P(Z$^1$)(O-linker-R$^L$)—O-oligonucleotide; wherein the oligonucleotide comprises (a) a sense strand, wherein said sense strand comprises (i) alternating 2'-fluoro modification (ii) at least one ligand; and (b) an antisense strand, wherein said antisense strand comprises (i) an alternating 2'-halogen modification; and (ii) a first 5' terminal antisense nucleotide, wherein said first 5' terminal antisense nucleotide is phosphorylated at its 5' carbon position.

R$^{30}$ is independently for each occurrence -linker-R$^L$ or R$^{31}$;

R$^L$ is hydrogen or a ligand;

R$^{31}$ is —C(O)CH(N(R$^{32}$)$_2$)(CH$_2$)$_h$N(R$^{32}$)$_2$;

R$^{32}$ is independently for each occurrence H, —R$^L$, -linker-R$^L$ or R$^{31}$;

Z$^1$ is independently for each occurrence O or S;

Z$^2$ is independently for each occurrence O, S, N(alkyl) or optionally substituted alkyl; and h is independently for each occurrence 1-20; and r and s are each independently for each occurrence 0, 1, 2 or 3. In addition to the cyclic carriers described herein, RRMS can include cyclic and acyclic carriers described in copending and co-owned U.S. application Ser. No. 10/916,185 filed Aug. 10, 2004, U.S. application Ser. No. 10/946,873 filed Sep. 21, 2004, and U.S. application Ser. No. 10/985,426, filed Nov. 9, 2004, U.S. application Ser. No. 10/833,934, filed Aug. 3, 2007 U.S. application Ser. No. 11/115,989 filed Apr. 27, 2005, and U.S. application Ser. No. 11/119,533, filed Apr. 29, 2005, contents of each are hereby incorporated by reference for all purposes.

Accordingly, in one aspect, the invention features, a monomer having the structure shown in formula (I)

(I)

wherein:

A and B are each independently for each occurrence O, N(R$^N$) or S;

R$^N$ is independently for each occurrence H or C$_1$-C$_6$ alkyl;

X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, a nucleoside, —P(Z')(Z")O-Linker-OP(Z''')(Z'''')O-oligonucleotide, an oligonucleotide, —P(Z')(Z")-formula (I), —P(Z')(Z")— or -Linker-R; wherein the oligonucleotide comprises (a) a sense strand, wherein said sense strand comprises (i) alternating 2'-fluoro modification (ii) at least one ligand; and (b) an antisense strand, wherein said antisense strand comprises (i) an alternating 2'-halogen modification; and (ii) a first 5' terminal antisense nucleotide, wherein said first 5' terminal antisense nucleotide is phosphorylated at its 5' carbon position.

R is L$^G$ or has the structure shown below:

L$^G$ is independently for each occurrence a ligand, e.g., carbohydrate, e.g. monosaccharide, disaccharide, trisaccharide, tetrasaccharide, polysaccharide; and Z', Z", Z''' and Z'''' are each independently for each occurrence O or S.

The term "linker" means an organic moiety that connects two parts of a compound. Linkers typically comprise a direct bond or an atom such as oxygen or sulfur, a unit such as NR$^8$, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(R$^8$), C(O), substituted or unsubstituted aryl, substituted or unsubstituted heteroaryl, substituted or unsubstituted heterocyclic; where R$^8$ is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

In one embodiment, the linker is -[(P-Q"-R)$_q$—X—(P'-Q'"-R')$_{q'}$]$_{q''}$-T-, wherein:

P, R, T, P', R' and T are each independently for each occurrence absent, CO, NH, O, S, OC(O), NHC(O), CH$_2$, CH$_2$NH, CH$_2$O; NHCH(R$^a$)C(O), —C(O)—CH(R$^a$)—NH—, CH=N—O,

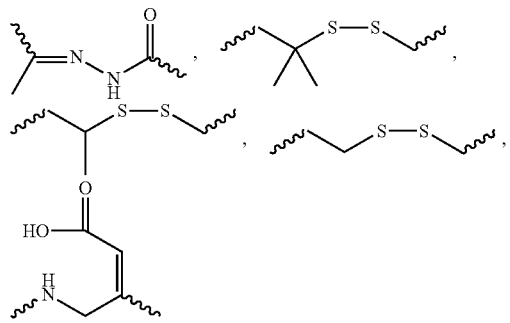

or heterocyclyl;

Q" and Q'" are each independently for each occurrence absent, —(CH$_2$)$_n$—, —C(R$^1$)(R$^2$)(CH$_2$)$_n$—, —(CH$_2$)C(R$^1$)(R$^2$)—, —(CH$_2$CH$_2$O)$_m$CH$_2$CH$_2$—, or —(CH$_2$CH$_2$O)$_m$CH$_2$CH$_2$NH—;

X is absent or a cleavable linking group;

R$^a$ is H or an amino acid side chain;

R$^1$ and R$^2$ are each independently for each occurrence H, CH$_3$, OH, SH or N(R$^N$)$_2$;

R$^N$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —N, —N(Q)—C, —O—C, —S—C, —SS—C, —C(O)N(Q)—C, —OC(O)N(Q)—C, —N(Q)C(O)—C, or —N(Q)C(O)O—C; wherein Q is independently for each occurrence H or optionally substituted alkyl. In other embodiment, the branchpoint is glycerol or glycerol derivative.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NH-CHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The term "monosaccharide" embraces radicals of allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhanmitol, rhamnosamine, rhamnose, ribose, ribulose, sedoheptulose, sorbose, tagatose, talose, tartaric acid, threose, xylose and xylulose. The monosaccharide can be in D- or L-configuration. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide" and "polysaccharide" embrace radicals of abcquose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructooligosachharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, xylobiose, umbelliferose and the like. Further, it is understood that the "disaccharide", "trisaccharide" and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

In one embodiment, the compound having the structure shown in formula (I'):

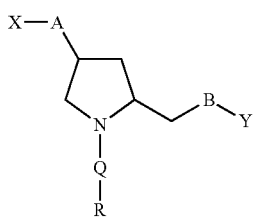

Formula (I')

wherein:

A and B are each independently for each occurrence O, $N(R^N)$ or S;

X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, a nucleoside, —P(Z')(Z")O—$R^1$-Q'-$R^2$—OP(Z''')(Z'''')O-oligonucleotide, or an oligonucleotide, —P(Z')(Z")-formula (I), —P(Z')(Z")— or -Q-R; wherein the oligonucleotide comprises
  (a) a sense strand, wherein said sense strand comprises
    (i) alternating 2'-fluoro modification
    (ii) at least one ligand; and
  (b) an antisense strand, wherein said antisense strand comprises
    (i) an alternating 2'-halogen modification; and
    (ii) a first 5' terminal antisense nucleotide, wherein said first 5' terminal antisense nucleotide is phosphorylated at its 5' carbon position.

R is $L^1$ or has the structure shown in formula (II)-(V):

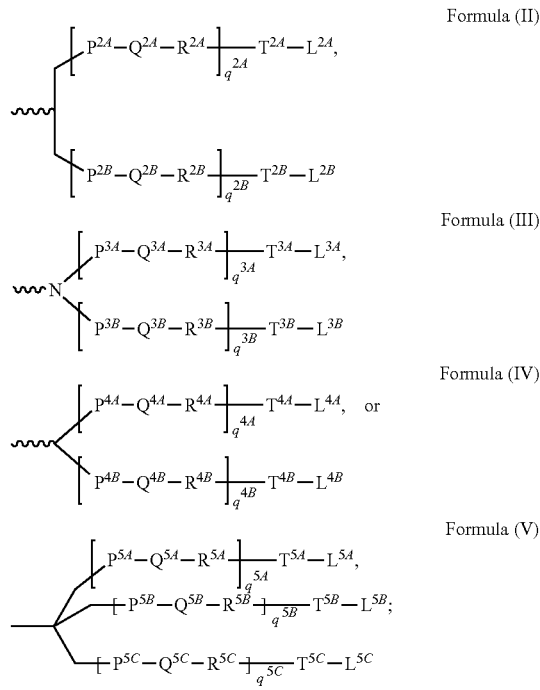

$q^{2A}$, $q^{2B}$, $q^{3A}$, $q^{3B}$, $q4^A$, $q^{4B}$, $q^{5A}$, $q^{5B}$ and $q^{5C}$ represent independently for each occurrence 0-20 and wherein the repeating unit can be the same or different;

Q and Q' are independently for each occurrence is absent, —$(P^7$-$Q^7$-$R^7)_g$-$T^7$- or -$T^7$-$Q^7$-$T^{7'}$-B-$T^{8'}$-$Q^8$-$T^8$;

$P^{2A}$, $P^{2B}$, $P^{3A}$, $P^{3B}$, $P4^A$, $P^{4B}$, $P^{5A}$, $P^{5B}$, $P^{5C}$, $P^7$, $T^{2A}$, $T^{2B}$, $T^{3A}$, $T^{3B}$, $T^{4A}$, $T^{4B}$, $T^{4A}$, $T^{5B}$, $T^{5C}$, $T^7$, $T^{7'}$, $T^8$ and $T^{8'}$ are each independently for each occurrence absent, CO, NH, O, S, OC(O), NHC(O), CH$_2$, CH$_2$NH or CH$_2$O;

B is —CH$_2$—N(B$^L$)—CH$_2$—;

B$^L$ is -$T^B$-$Q^B$-$T^{B'}$-$R^x$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$, $Q^7$, $Q^8$ and $Q^B$ are independently for each occurrence absent, alkylene, substituted alkylene and wherein one or more methylenes can be interrupted or terminated by one or more of O, S, S(O), SO$_2$, N(R$^N$), C(R')=C(R'), C≡C or C(O);

$T^B$ and $T^{B'}$ are each independently for each occurrence absent, CO, NH, O, S, OC(O), OC(O)O, NHC(O), NHC(O)NH, NHC(O)O, CH$_2$, CH$_2$NH or CH$_2$O;

R$^x$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid;

$R^1$, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^7$ are each independently for each occurrence absent, NH, O, S, CH$_2$, C(O)O, C(O)NH, NHCH(R$^a$)C(O), —C(O)—CH (R$^a$)—NH—, CO, CH=N—O,

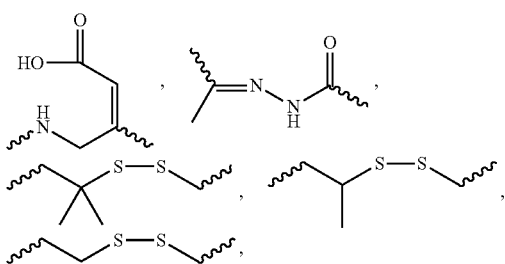

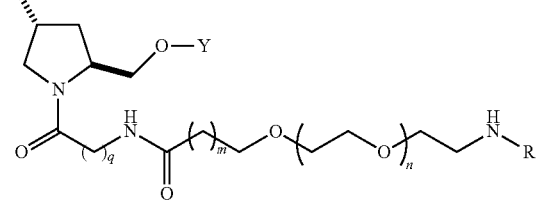

or heterocyclyl;

$L^1, L^{2A}, L^{2B}, L^{3A}, L^{3B}, L^{4A}, L^{4B}, L^{5A}, L^{5B}$ and $L^{5C}$ are each independently for each occurrence a carbohydrate, e.g., monosaccharide, disaccharide, trisaccharide, tetrasaccharide, oligosaccharide and polysaccharide;

R' and R" are each independently H, $C^1$-$C_6$ alkyl, OH, SH, or $N(RN)_2$;

$R^N$ is independently for each occurrence H, methyl, ethyl, propyl, isopropyl, butyl or benzyl;

$R^a$ is H or amino acid side chain;

Z', Z", Z''' and Z''' are each independently for each occurrence O or S;

p represent independently for each occurrence 0-20.

In some embodiments, the formula (I') has the structure

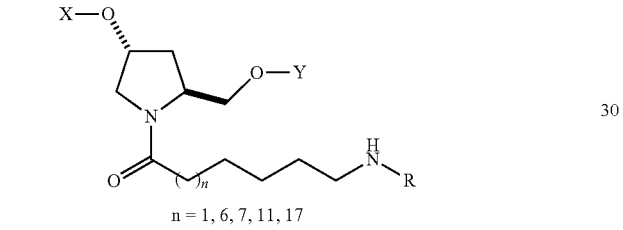

n = 1, 6, 7, 11, 17

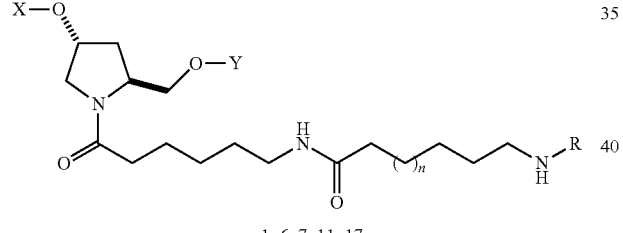

n = 1, 6, 7, 11, 17

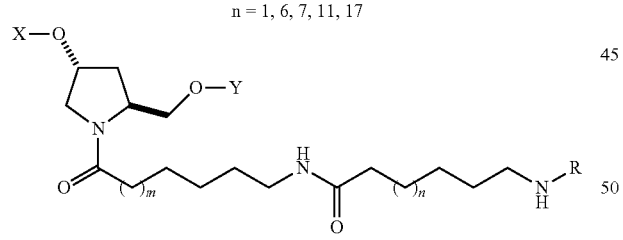

m = 1, 6, 7, 11, 17
n = 1, 6, 7, 11, 17

In some embodiments, the formula (I') has the structure

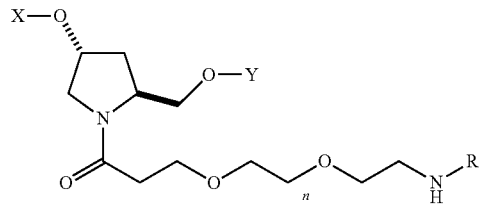

m = 0 or 1, n = 1, 2, 3, 4

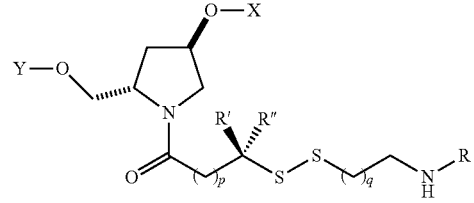

m = 0 or 1, n = 1, 2, 3, 4 and
p = 2, 3, 5, 9, 15

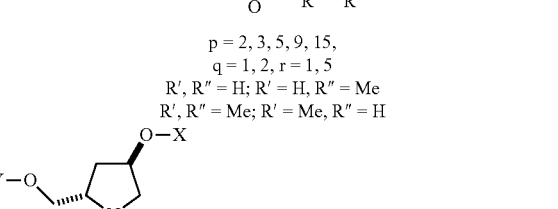

p = 1, 2; q = 1, 5
R', R" = H; R' = H, R" = Me
R', R" = Me; R' = Me, R" = H

In some embodiments, the formula (I') has the structure

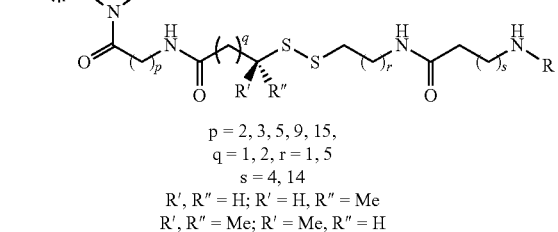

p = 2, 3, 5, 9, 15,
q = 1, 2, r = 1, 5
R', R" = H; R' = H, R" = Me
R', R" = Me; R' = Me, R" = H

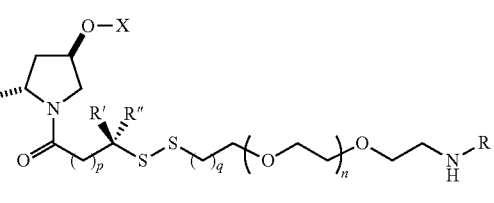

p = 2, 3, 5, 9, 15,
q = 1, 2, r = 1, 5
s = 4, 14
R', R" = H; R' = H, R" = Me
R', R" = Me; R' = Me, R" = H

In some embodiments, the formula (I') has the structure p = 1, 2; q = 1, 5 and n = 2, 3, 4, 5
R', R" = H; R' = H, R" = Me
R', R" = Me; R' = Me, R" = H

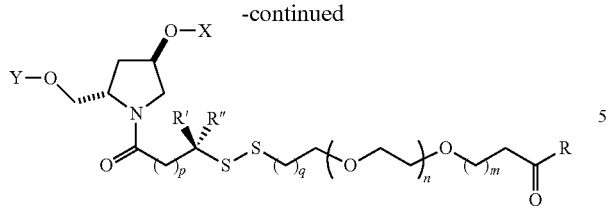
p = 1, 2; q = 1, 5 and n = 2, 3, 4, 5
m = 0 or 1
R', R" = H; R' = H, R" = Me
R', R" = Me; R' = Me, R" = H
In some embodiments, the formula (I') has the structure
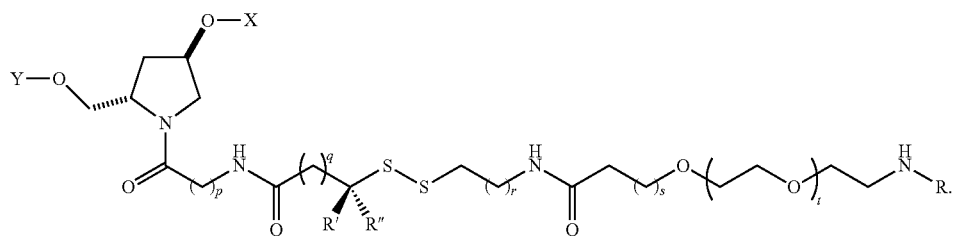
p = 2, 3, 5, 9, 15, q = 1, 2, r = 1, 5
s = 0 or 1 and t = 1, 2, 3 or 4
R', R" = H; R' = H, R" = Me
R', R" = Me; R' = Me, R" = H
In some embodiments, R is
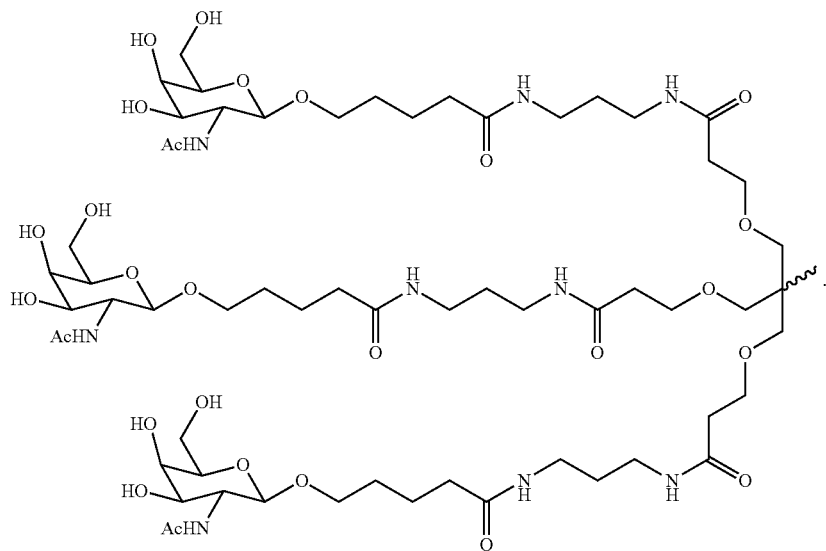 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, R is
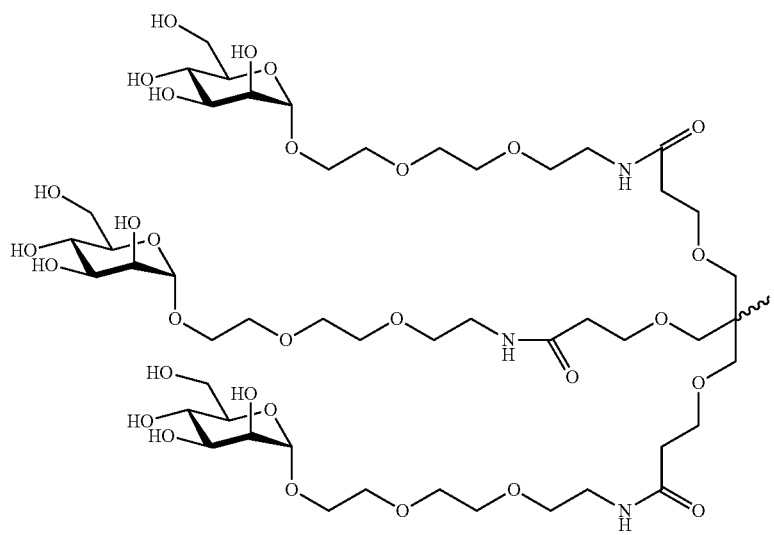
In some embodiments, R is
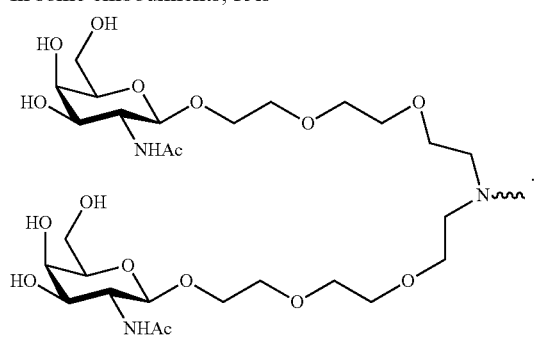
In some embodiments, R is
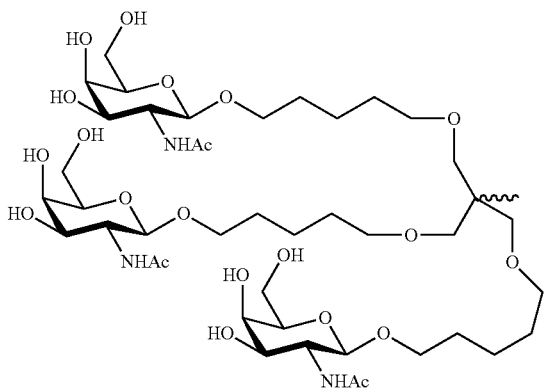
In some embodiments, R is
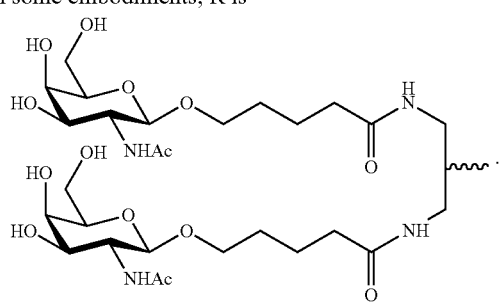
In some embodiments, R is
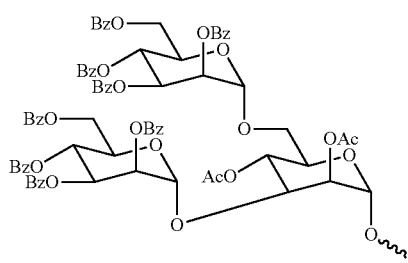

In some embodiments, R is
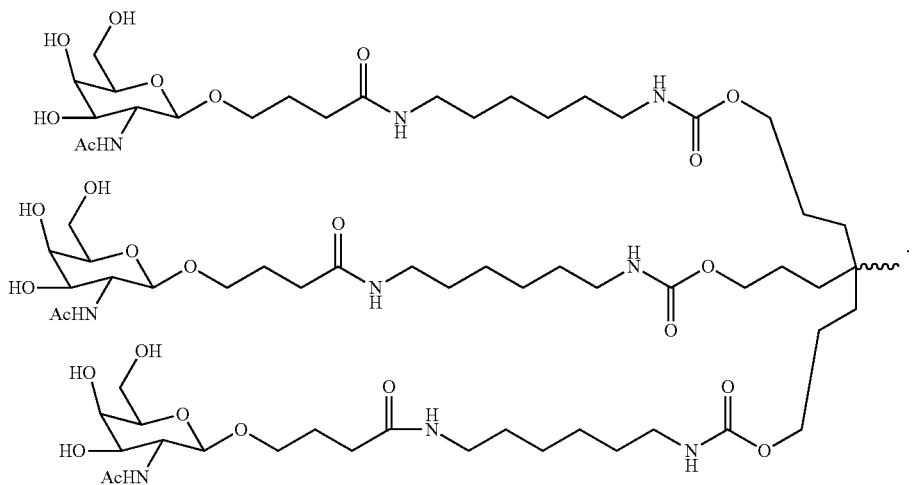 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]
In some embodiments, R is
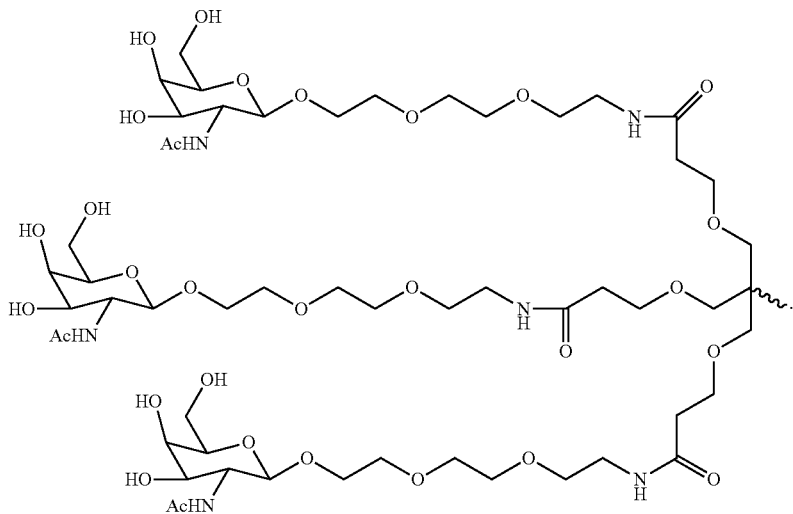 [SMILES: CC(=O)NC1C(OCCOCCOCCNC(=O)CCOCC(C)(COCCC(=O)NCCOCCOCCOC2OC(CO)C(O)C(O)C2NC(C)=O)COCCC(=O)NCCOCCOCCOC2OC(CO)C(O)C(O)C2NC(C)=O)OC(CO)C(O)C1O]
In some preferred embodiments, R is
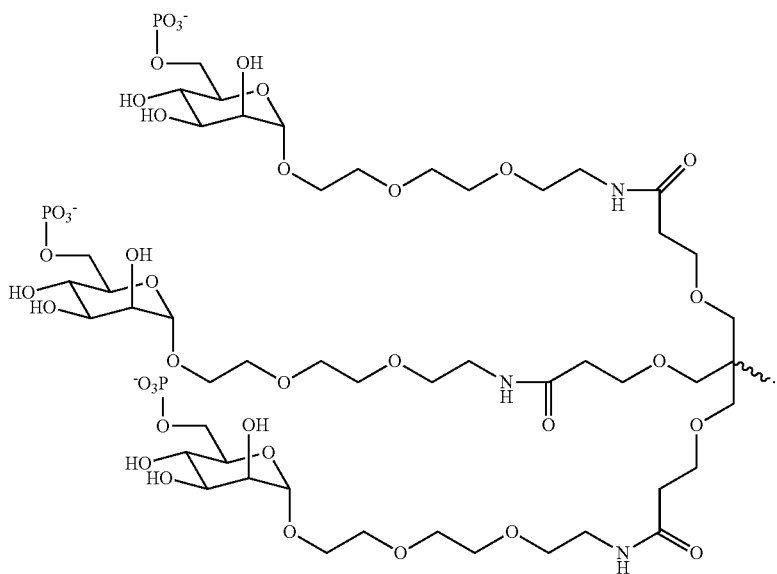

In some preferred embodiments, R is
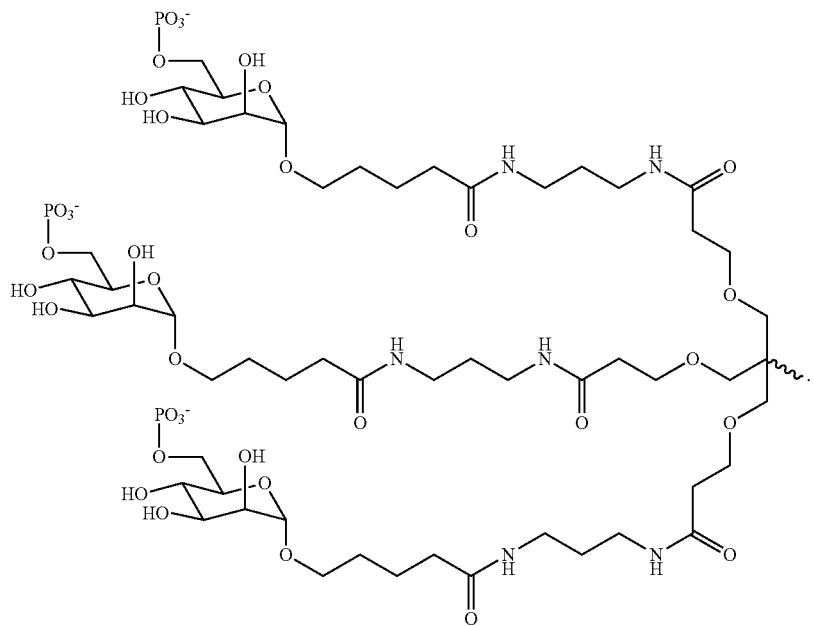
In some preferred embodiments, formula (I) has the structure
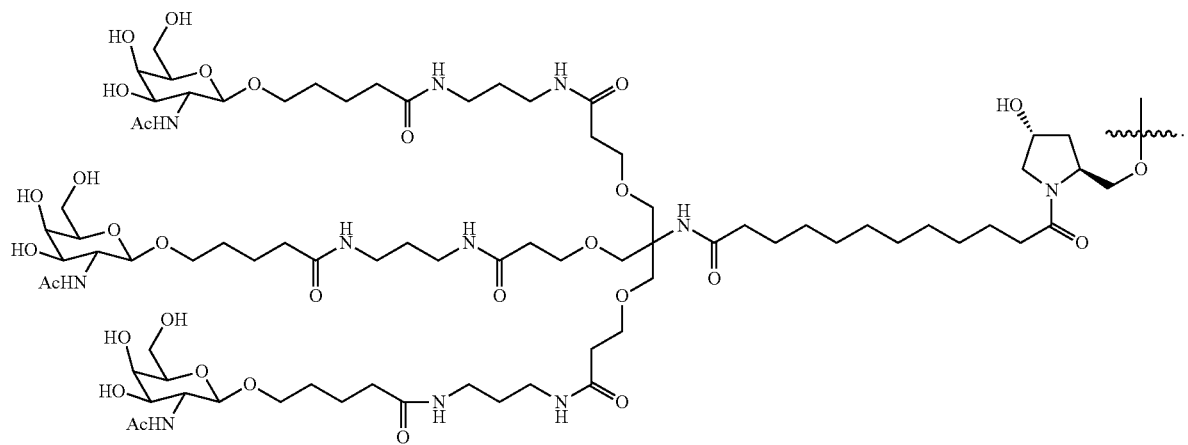 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]
In some embodiments R is
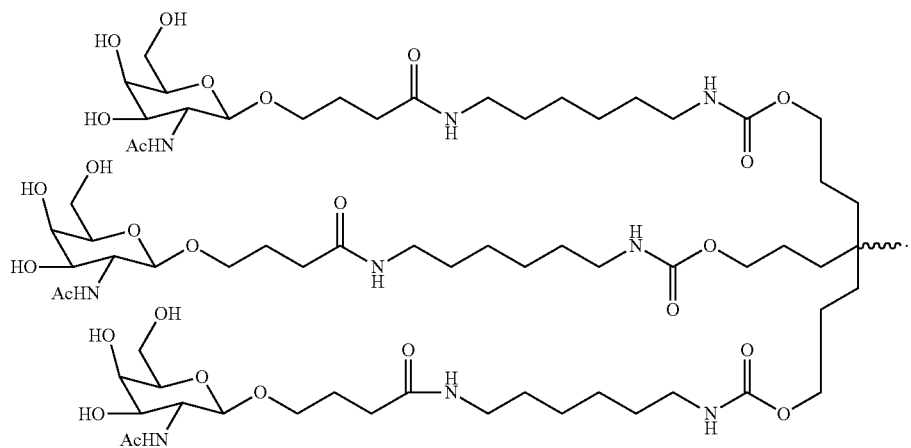 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]

In some embodiments monomer of formula (I) has the structure
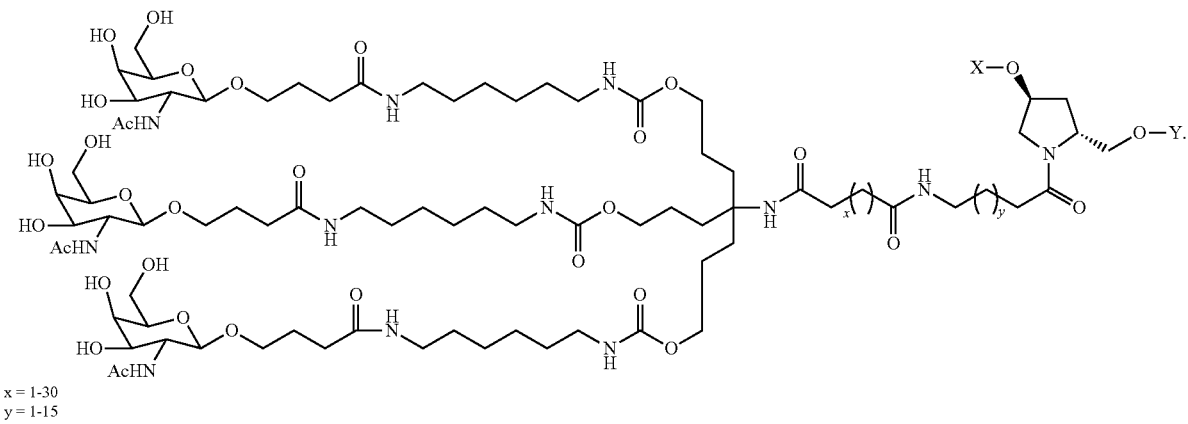
x = 1-30
y = 1-15
In some embodiments monomer of formula (I) has the structure
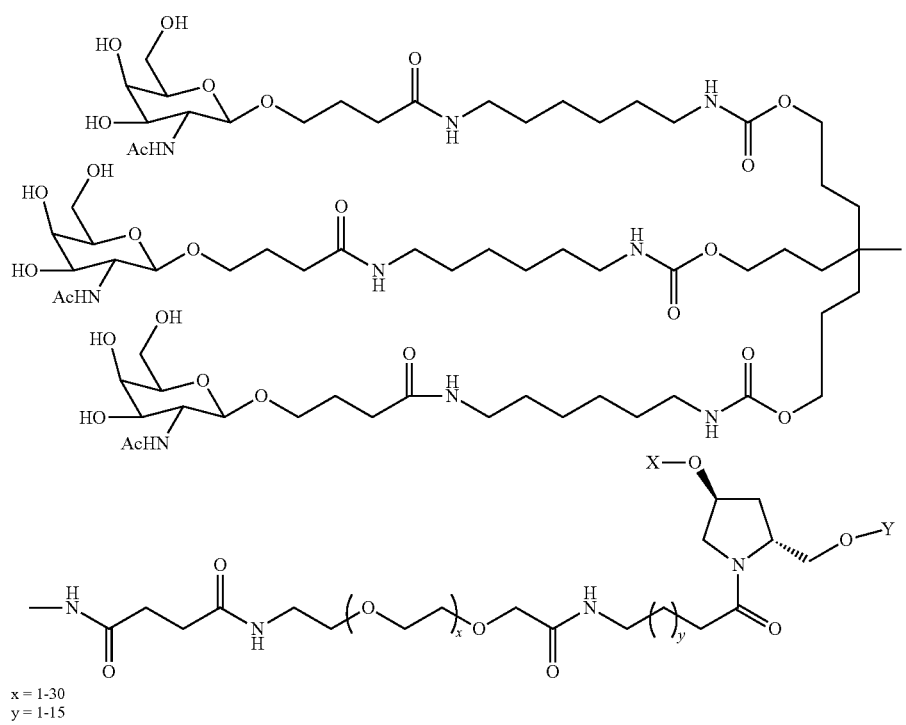
x = 1-30
y = 1-15
In some embodiments monomer of formula (I) has the structure
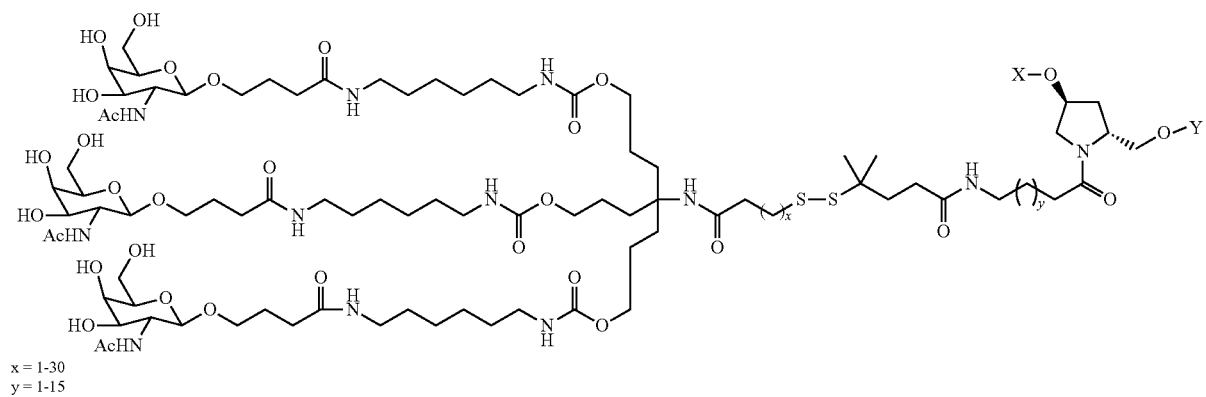
x = 1-30
y = 1-15

In some embodiments monomer of formula (I) has the structure
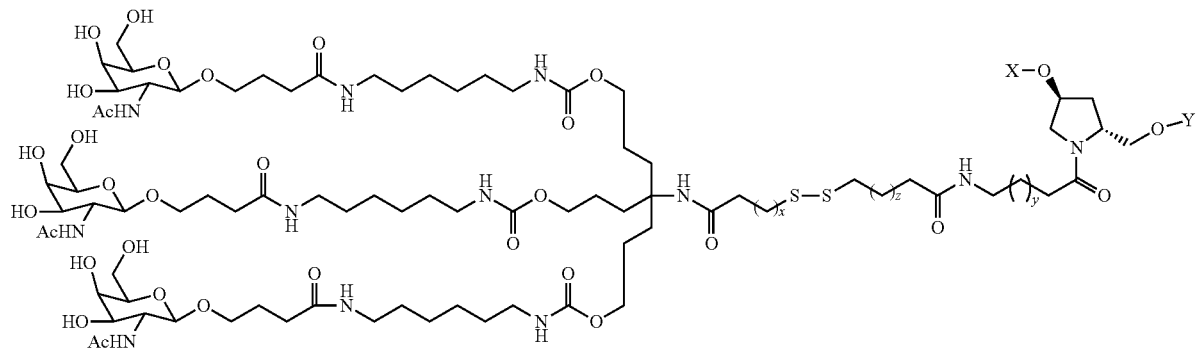
x = 0-30
y = 1-15
z = 1-20
In some embodiments monomer of formula (I) has the structure
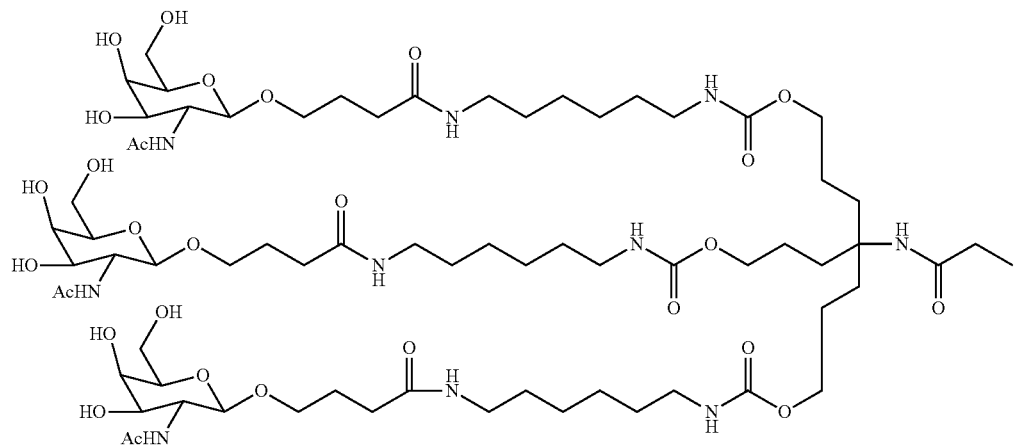
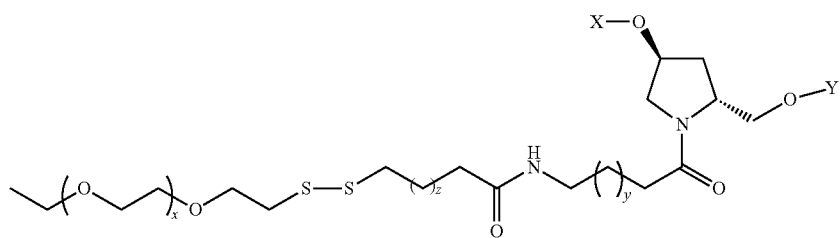
x = 1-30
y = 1-15
z = 1-20

In some embodiments monomer of formula (I) has the structure
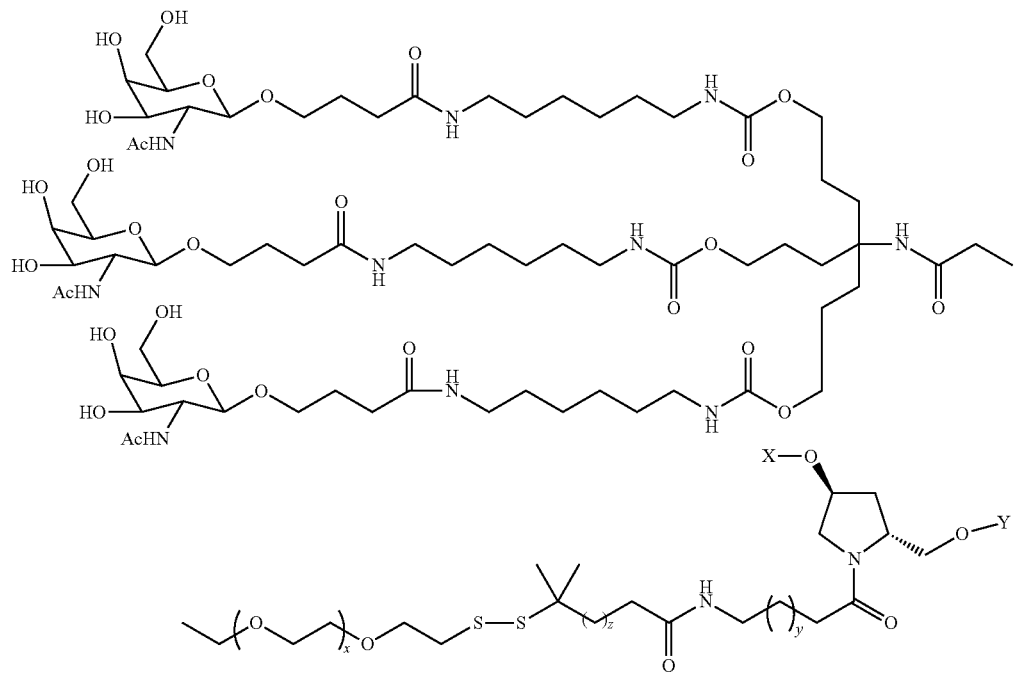
x = 1-30
y = 1-15
z = 1-20
In some embodiments, R is
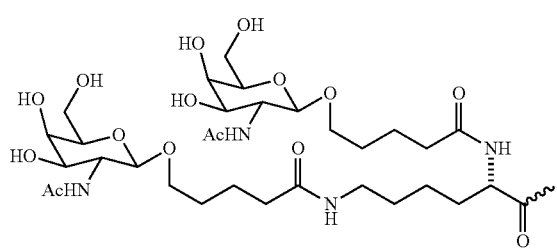
In some embodiments, R is
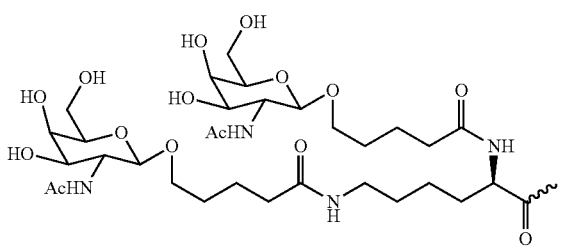
In some embodiments, R is
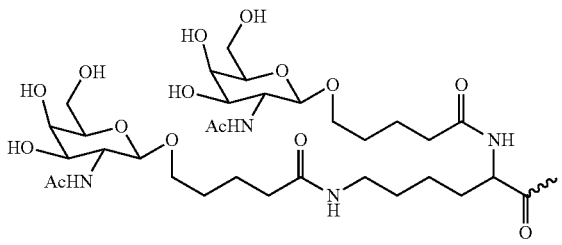
In some embodiments, R is
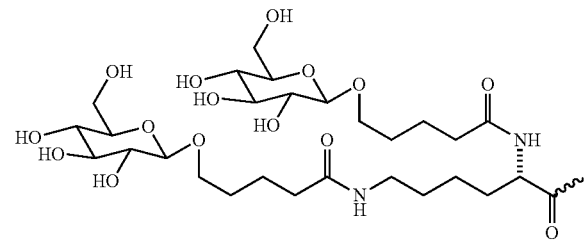
In some embodiments, R is
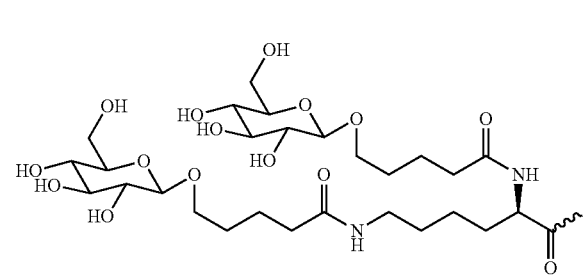
In some embodiments, R is
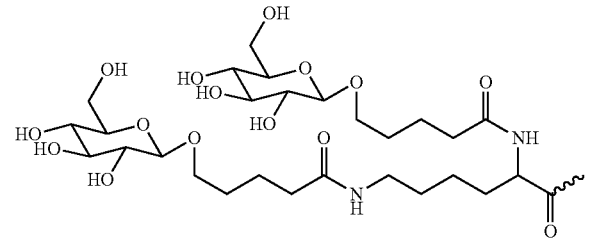

In some embodiments, R is
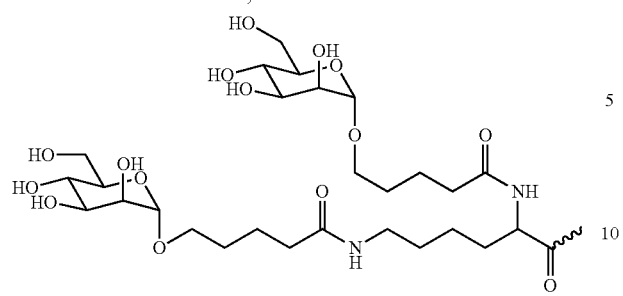
In some embodiments, R is
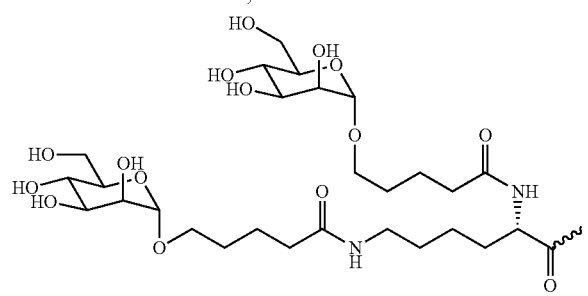
In some embodiments, R is
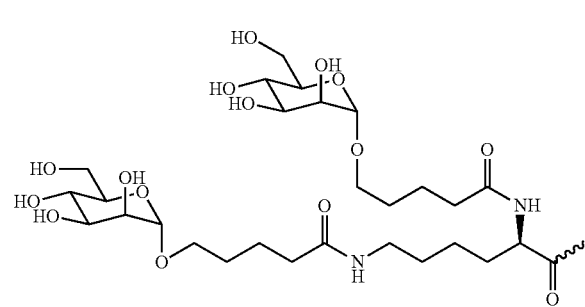
In some preferred embodiments, formula (I) has the structure
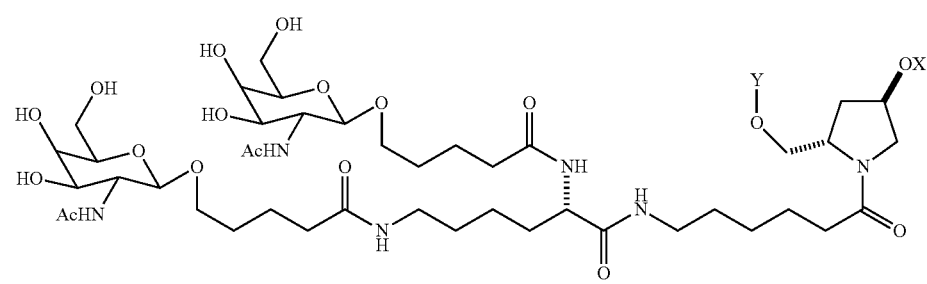
In some preferred embodiments, formula (I) has the structure
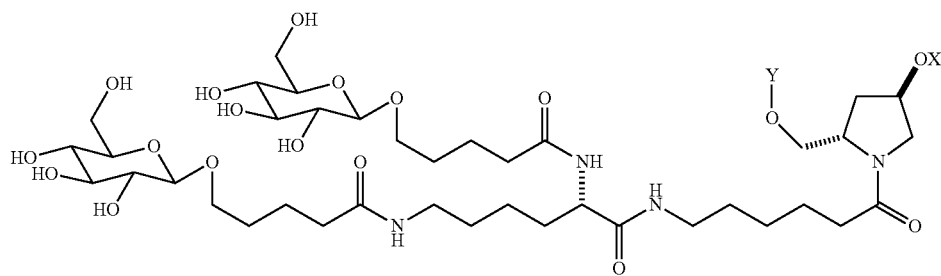
In some preferred embodiments, formula (I) has the structure
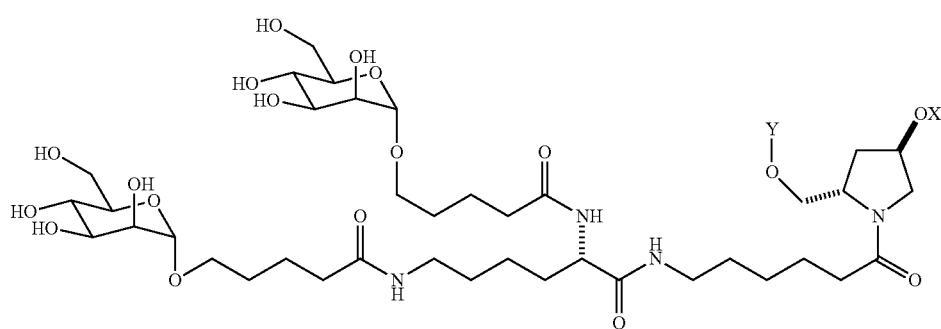

In some preferred embodiments, formula (I) has the structure

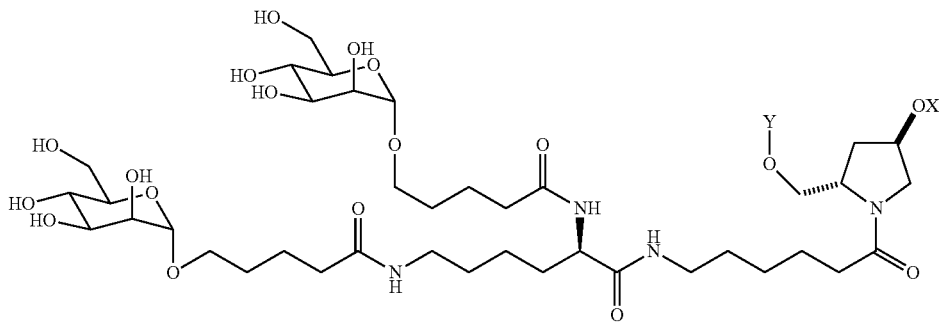

In some preferred embodiments, formula (I) has the structure

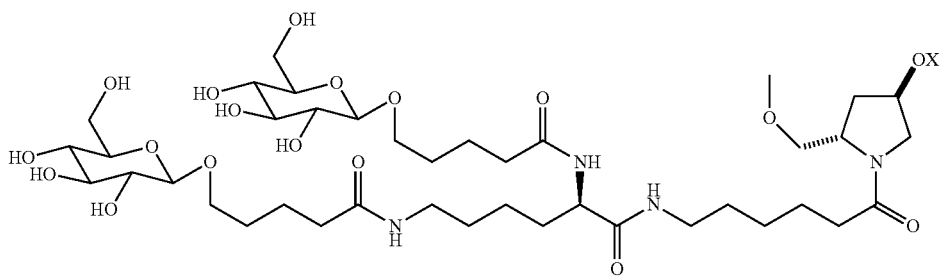

In some preferred embodiments, formula (I) has the structure

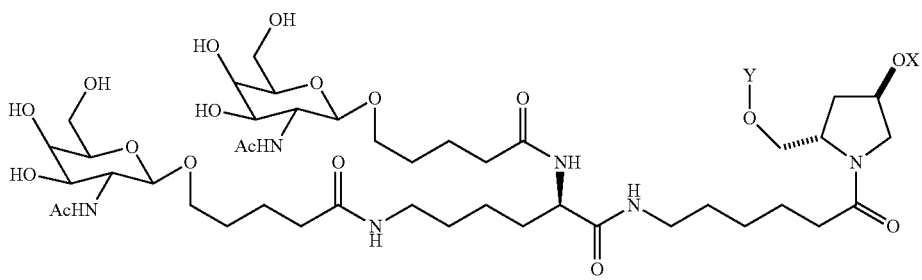

In some preferred embodiments both $L^{2A}$ and $L^{2B}$ are the same.

In some embodiments both $L^{2A}$ and $L^{2B}$ are different.

In some preferred embodiments both $L^{3A}$ and $L^{3B}$ are the same.

In some embodiments both $L^{3A}$ and $L^{3B}$ are different.

In some preferred embodiments both $L^{4A}$ and $L^{4B}$ are the same.

In some embodiments both $L^{4A}$ and $L^{4B}$ are different.

In some preferred embodiments all of $L^{5A}$, $L^{5B}$ and $L^{5C}$ are the same.

In some embodiments two of $L^{5A}$, $L^{5B}$ and $L^{5C}$ are the same.

In some embodiments $L^{5A}$ and $L^{5B}$ are the same.

In some embodiments $L^{5A}$ and $L^{5C}$ are the same.

In some embodiments $L^{5B}$ and $L^{5C}$ are the same.

In another aspect, the invention features, an iRNA duplex agent comprising at least one monomer of formula (I).

In some embodiments, the iRNA duplex agent will comprise 1, 2, 3, 4 or 5 monomers of formula (I), more preferably 1, 2 or 3 monomers of formula (I), more preferably 1 or 2 monomers of formula (I), even more preferably only one monomer of formula (I).

In some embodiments, all the monomers of formula (I) are on the same strand of a double stranded iRNA duplex agent.

In some embodiments, the monomers of formula (I) are on the separate strands of a double strand of an iRNA duplex agent.

In some embodiments, all monomers of formula (I) in an iRNA duplex agent are the same.

In some embodiments, the monomers of formula (I) in an iRNA duplex agent are all different.

In some embodiments, only some monomers of formula (I) in an iRNA duplex agent are the same.

In some embodiments, the monomers of formula (I) will be next to each other in the iRNA duplex agent.

In some embodiments, the monomers of formula (I) will not be next to each other in the iRNA duplex agent.

In some embodiments, the monomer of formula (I) will be on the 5'-end, 3'-end, at an internal position, both the 3'- and the 5'-end, both 5'-end and an internal position, both 3'-end and internal position, and at all three positions (5'-end, 3'-end and an internal position) of the iRNA duplex agent.

In some preferred embodiments, $R^x$ is cholesterol.

In some preferred embodiments, $R^x$ is lithocholic.

In some preferred embodiments, $R^x$ is oleyl lithocholic.

In some preferred embodiments, $R^x$ has the structure

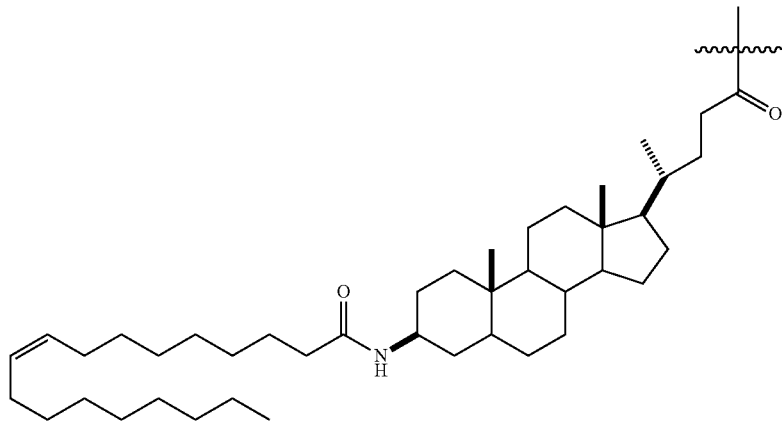

In some preferred embodiments $B^L$ has the structure

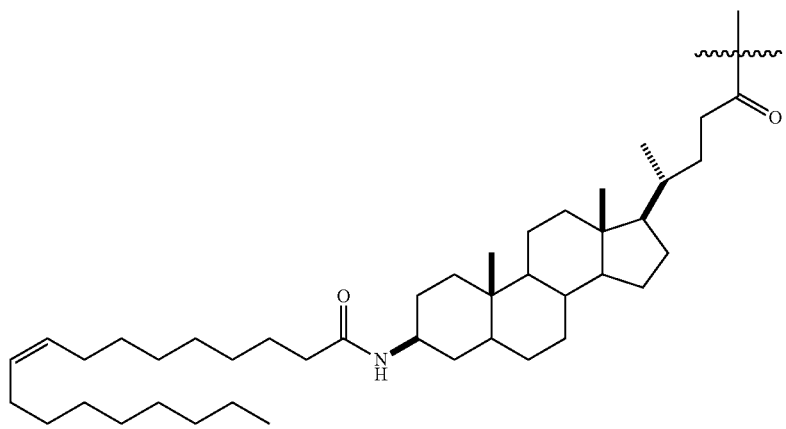

In some preferred embodiments, formula (I) has the structure

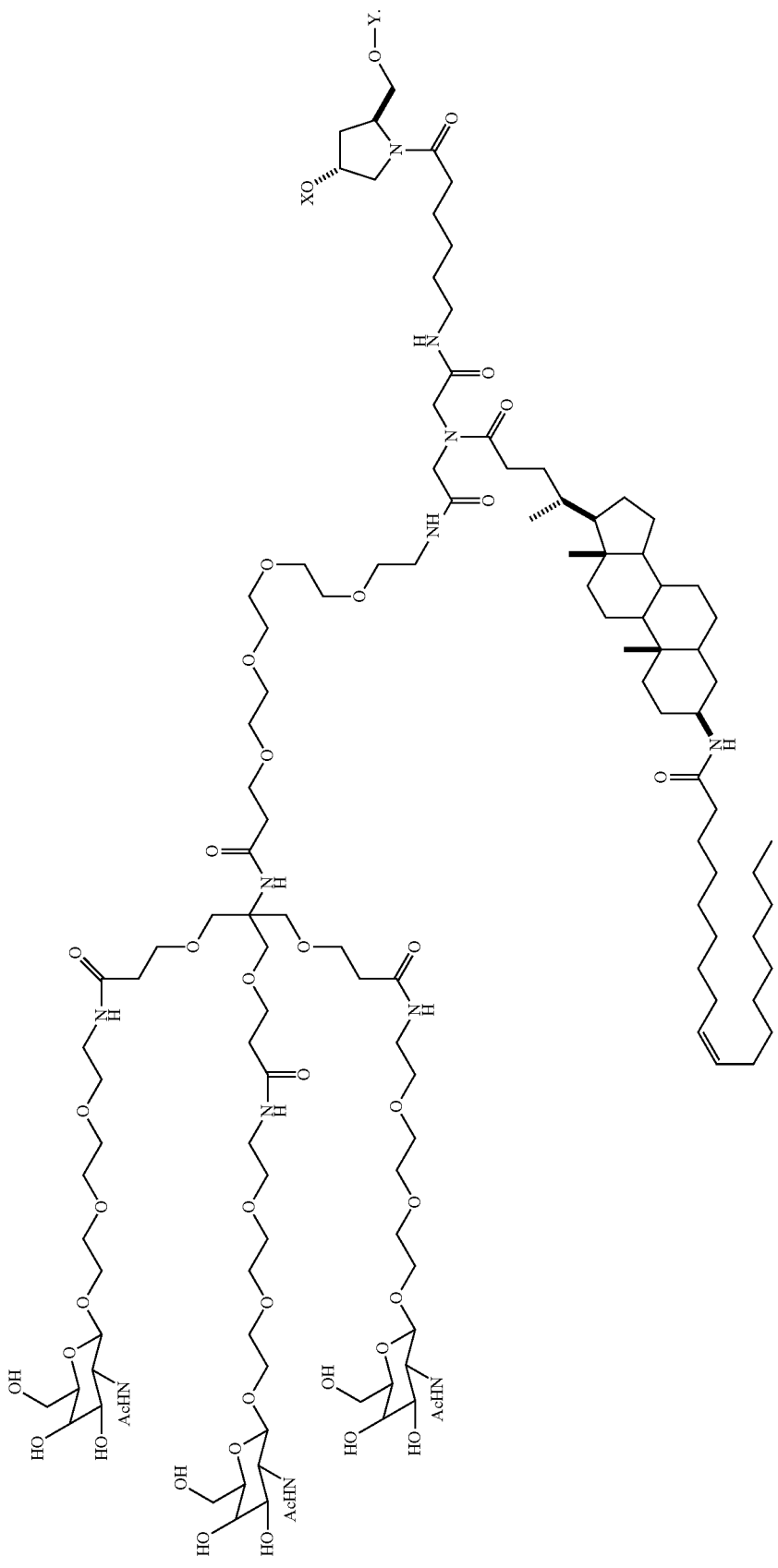

In some preferred embodiments, formula (I) has the structure

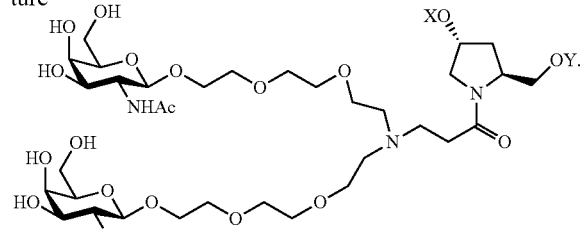

In some preferred embodiments, formula (I) has the structure

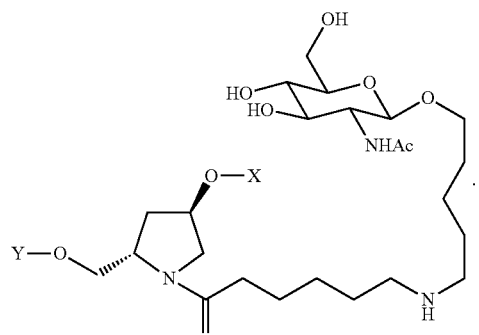

In some preferred embodiments, formula (I) has the structure

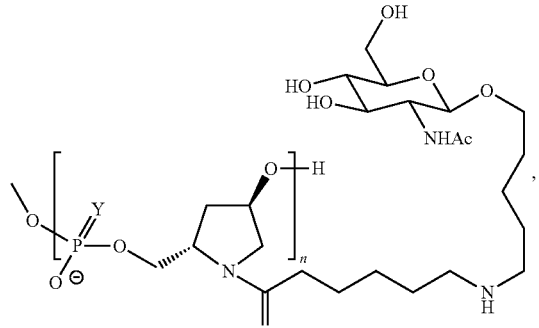

wherein Y is O or S and n is 3-6.

In some preferred embodiments, formula (I) has the structure

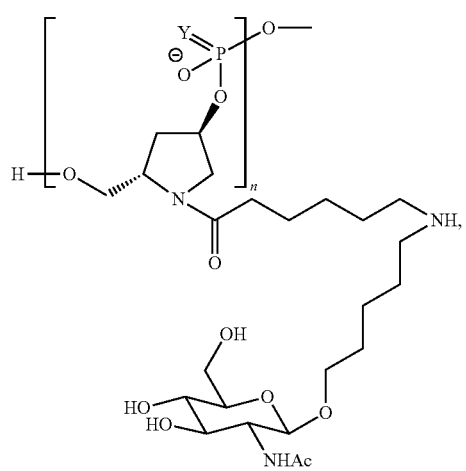

wherein Y is O or S and n is 3-6.

In some preferred embodiments, formula (I) has the structure

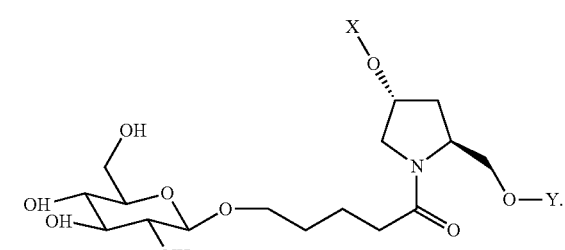

In some preferred embodiments, formula (I) has the structure

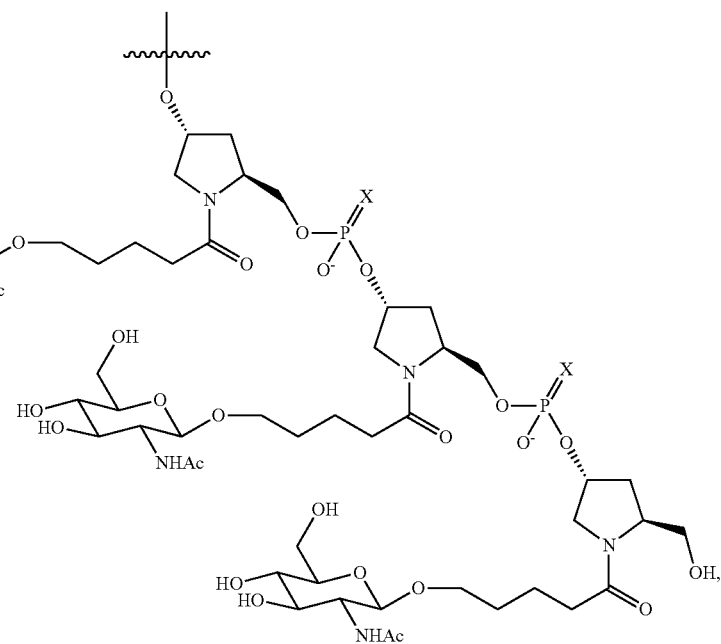

wherein X is O or S.

In some preferred embodiments, formula (I) has the structure
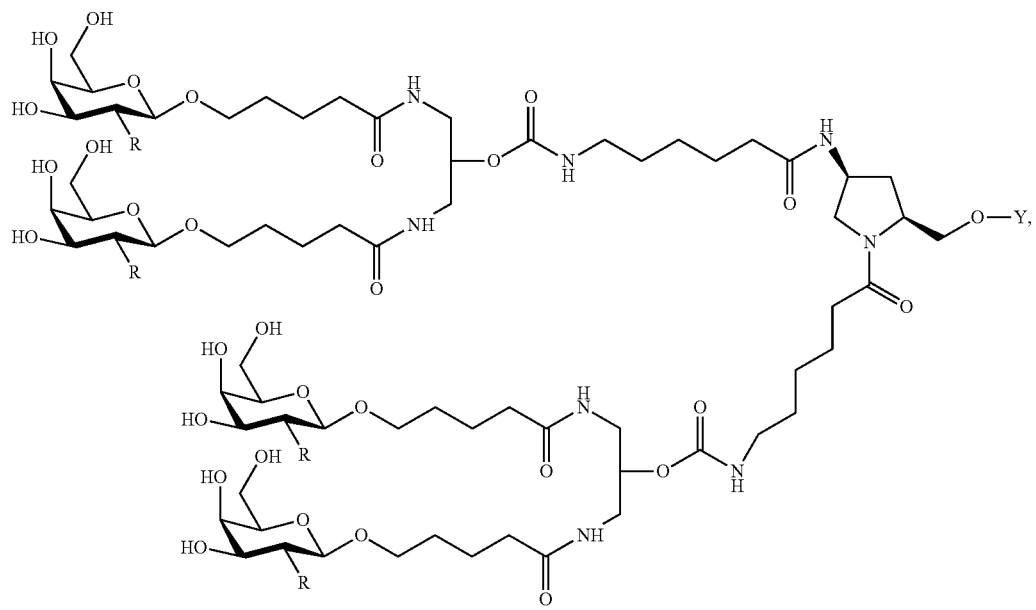
wherein R is OH or NHCOOH.
In some preferred embodiments, formula (I) has the structure
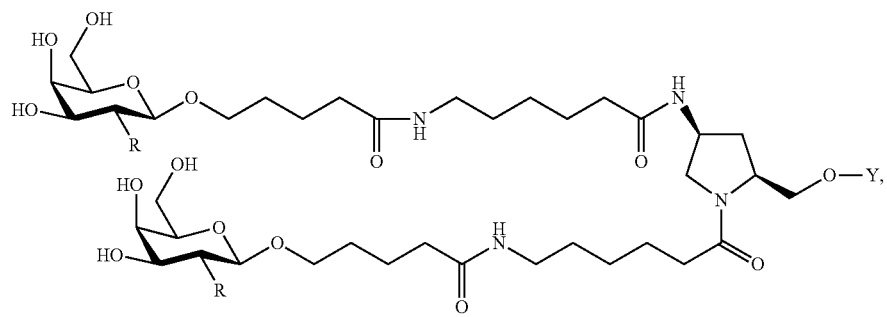
wherein R is OH or NHCOOH.
In some preferred embodiments, monomer of formula (I) is linked to the iRNA duplex agent through a linker of formula (VII)
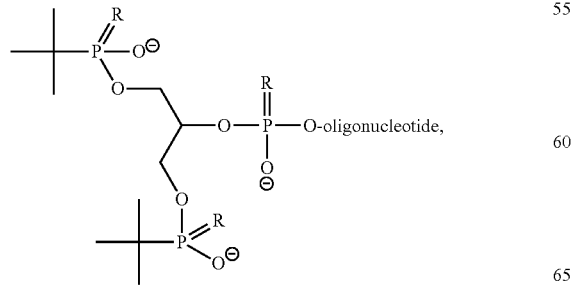
Formula (VII)
wherein R is O or S.

In some preferred embodiments, formula (I) has the structure
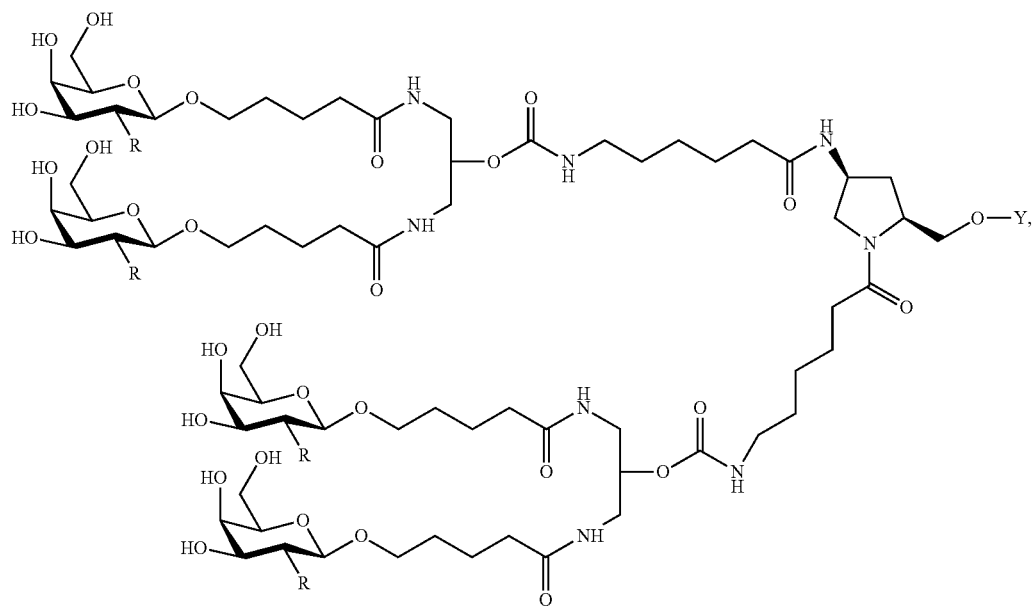
wherein R is OH or NHCOOH.
In some preferred embodiments, formula (I) has the structure
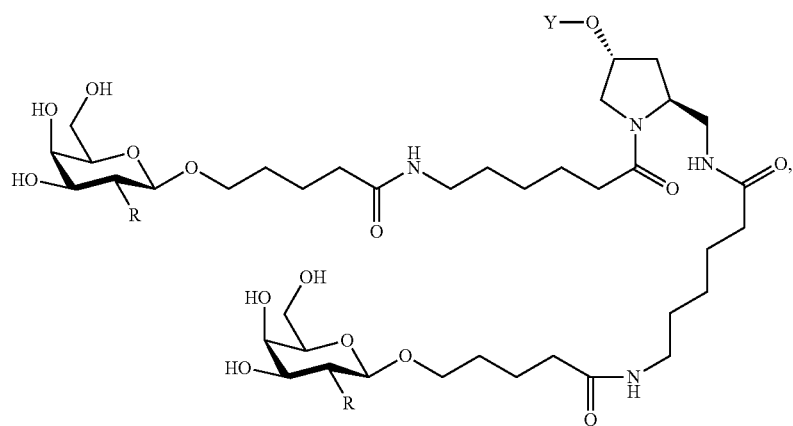
In some preferred embodiments, formula (I) has the structure
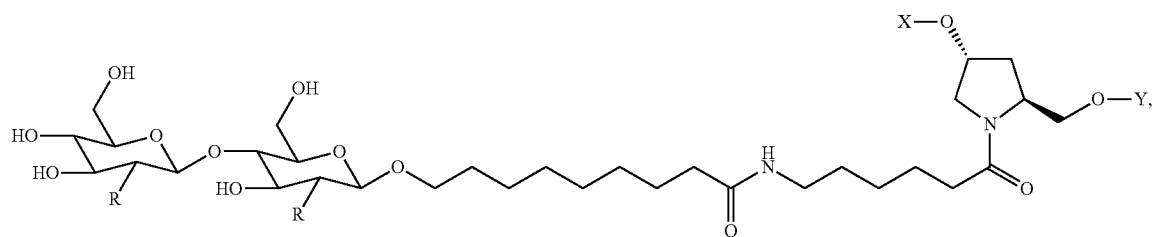
where in R is OH or NHCOOH.

In some preferred embodiments, formula (I) has the structure

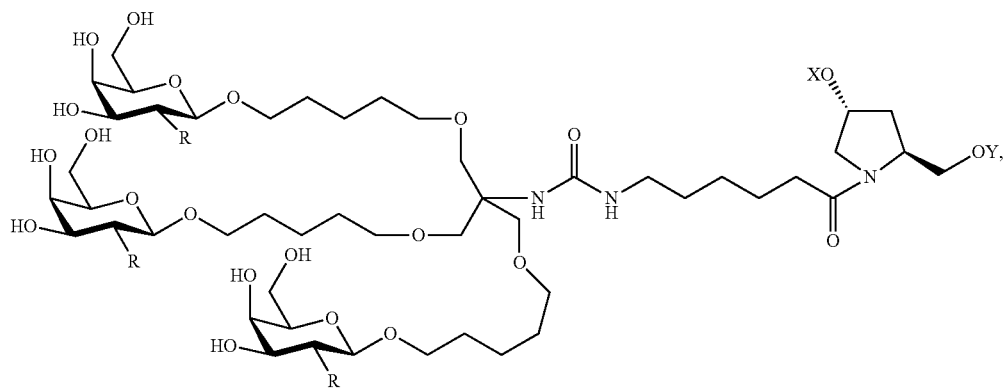

wherein R is OH or NHCOOH.

In some preferred embodiments, formula (I) has the structure

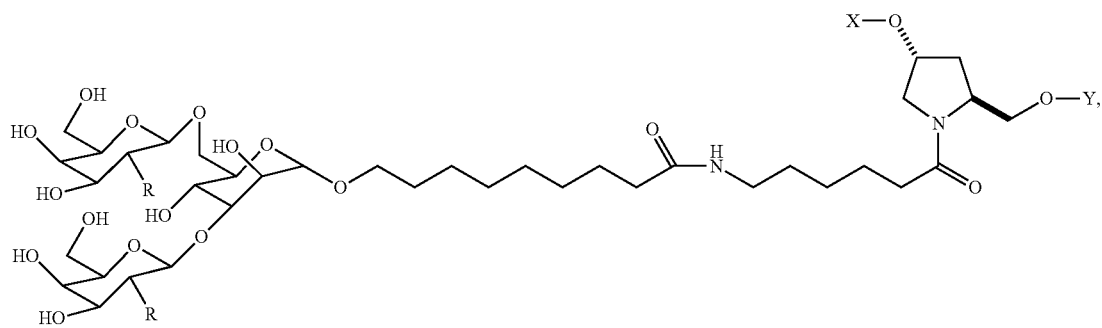

wherein R is OH or NHCOOH.

In some preferred embodiments, formula (I) has the structure

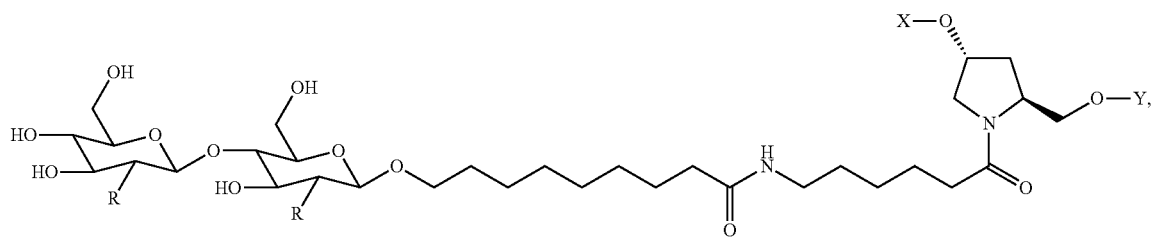

wherein R is OH or NHCOOH.

In some embodiments, the iRNA duplex agent will have a monomer with the structure shown in formula (VI) in addition to monomer of formula (I)

Formula (VI)

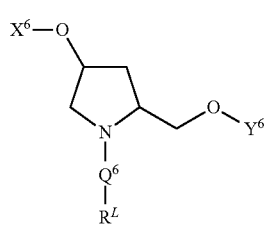

wherein $X^6$ and $Y^6$ are each independently H, OH, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O—$R^1$-Q'-$R^2$—OP(Z''')(Z'''')O-oligonucleotide, a nucleotide, or an oligonucleotide, —P(Z')(Z")-formula (I) or —P(Z')(Z")—; wherein the oligonucleotide comprises (a) a sense strand, wherein said sense strand comprises
 (i) alternating 2'-fluoro modification
 (ii) at least one ligand; and
(b) an antisense strand, wherein said antisense strand comprises
 (i) an alternating 2'-halogen modification; and
 (ii) a first 5' terminal antisense nucleotide, wherein said first 5' terminal antisense nucleotide is phosphorylated at its 5' carbon position.

$Q^6$ is absent or -($P^6$-$Q^6$-$R^6$)$_v$-$T^6$-;

$P^6$ and $T^6$ are each independently for each occurrence absent, CO, NH, O, S, OC(O), NHC(O), $CH_2$, $CH_2NH$ or $CH_2O$;

$Q^6$ is independently for each occurrence absent, substituted alkylene wherein one or more methylenes can be interrupted or terminated by one or more of O, S, S(O), $SO_2$, $N(R^N)$, $C(R')=C(R')$, $C\equiv C$ or C(O);

$R^6$ is independently for each occurrence absent, NH, O, S, $CH_2$, C(O)O, C(O)NH, $NHCH(R^a)C(O)$, —C(O)—CH$(R^a)$—NH—, CO, CH=N—O,

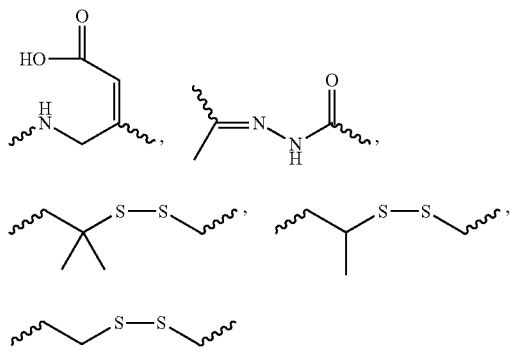

or heterocyclyl;

R' and R" are each independently H, $C_1$-$C_6$ alkyl OH, SH, $N(R^N)_2$;

$R^N$ is independently for each occurrence methyl, ethyl, propyl, isopropyl, butyl or benzyl;

$R^a$ is H or amino acid side chain;

Z', Z", Z'" and Z"" are each independently for each occurrence O or S;

v represent independently for each occurrence 0-20;

$R^L$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid.

In some embodiments, one or more, e.g., 1, 2, 3, 4 or 5, monomers of formula (VI) in addition to one or more, e.g. 1, 2, 3, 4, or 5, monomers of formula (I) are present in the iRNA duplex agent.

In some preferred embodiments only 1 monomer of formula (I) and 1 monomer of formula (VI) are present in the iRNA duplex agent.

In some embodiments, $R^L$ is cholesterol.

In some embodiments, $R^L$ is lithocholic.

In some embodiments, $R^L$ is oleyl lithocholic.

In some embodiments, monomer of formula (I) is covalently linked with the monomer of formula (VI).

In some preferred embodiments, monomer of formula (I) is linked with the monomer of formula (VI) through a phosphate linkage, e.g. a phosphodiester linkage, a phosphorothioate linkage, a phosphorodithioate linkage.

In some preferred embodiments, monomer of formula (I) is linked to the iRNA duplex agent through the monomer of formula (VI).

In some embodiments, monomer of formula (I) intervenes between the iRNA duplex agent and the monomer of formula (VI).

In some embodiments, monomer of formula (I) and monomer of formula (II) are directly linked to each other.

In some embodiments, monomer of formula (I) and monomer of formula (II) are not directly linked to each other.

In some embodiments, monomer of formula (I) and monomer of formula (VI) are on separate strands of a double stranded iRNA duplex agent.

In some embodiments, monomer of formula (I) and monomer of formula (VI) are on opposite terminal ends of the iRNA duplex agent.

In some embodiments, monomer of formula (I) and monomer of formula (VI) are on the same terminal end of the iRNA duplex agent.

In some embodiments, one of monomer of formula (I) or monomer of formula (VI) is at an internal position while the other is at a terminal position of an iRNA duplex agent.

In some embodiments, monomer of formula (I) and monomer of formula (VI) are both at an internal position of the iRNA duplex agent.

In some preferred embodiments, monomer of formula (VI) has the structure

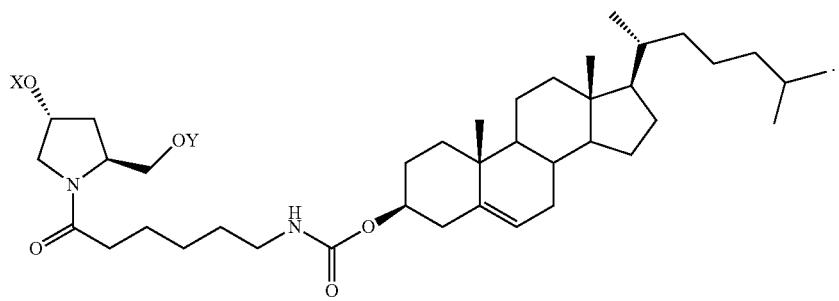

In some embodiments, the iRNA duplex agent of the invention is selected from the group consisting of:
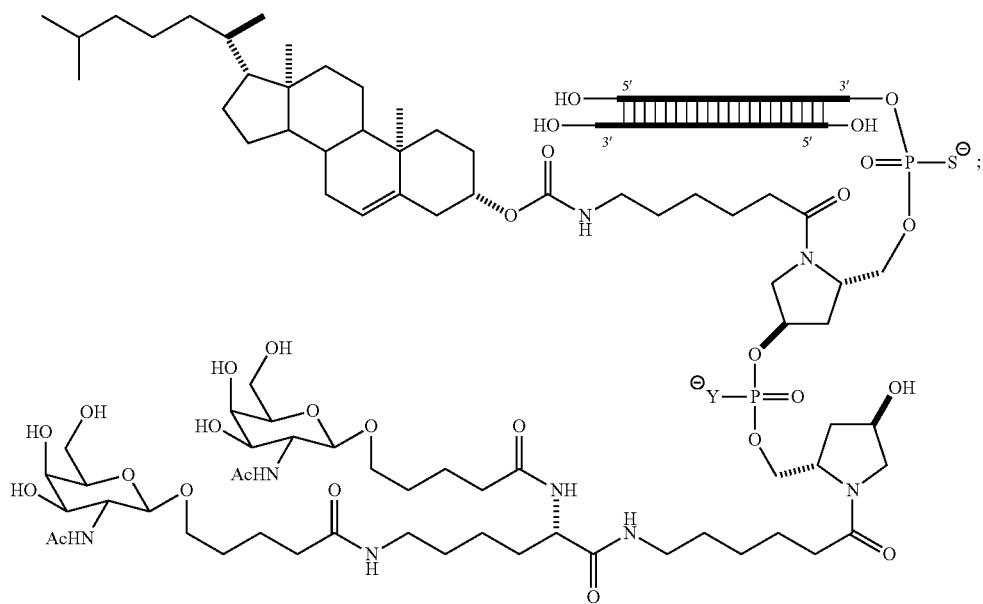
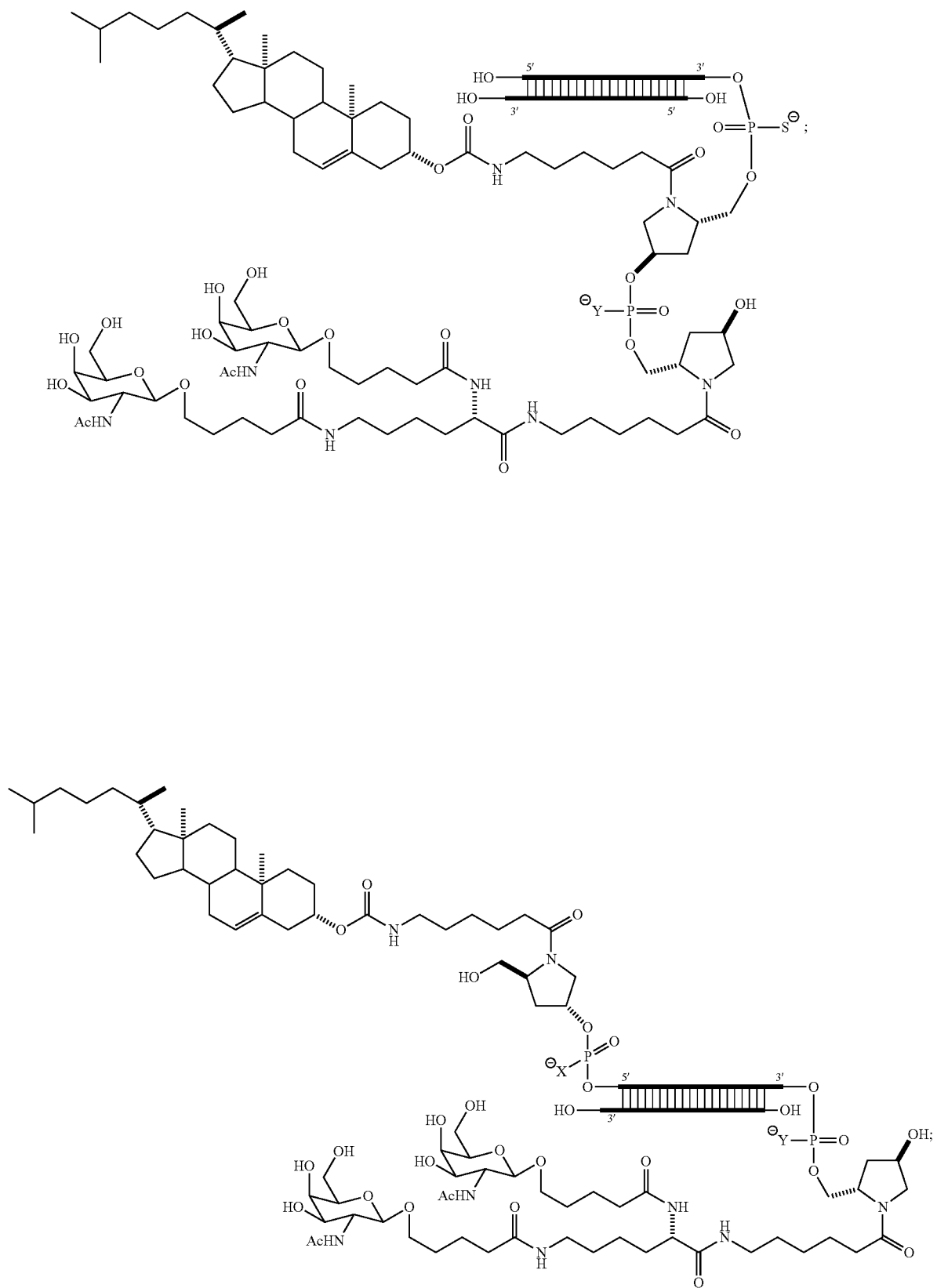

-continued
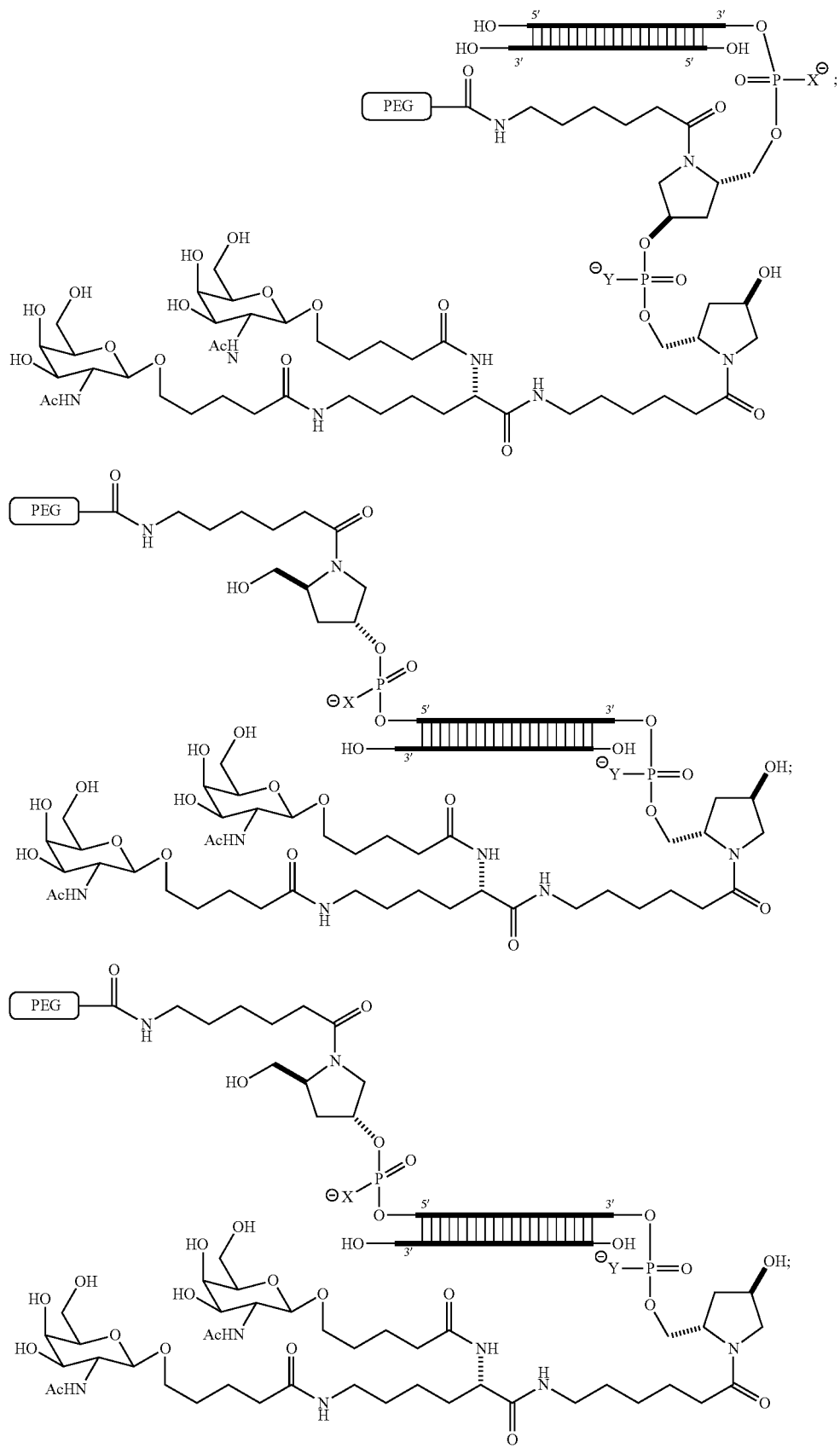

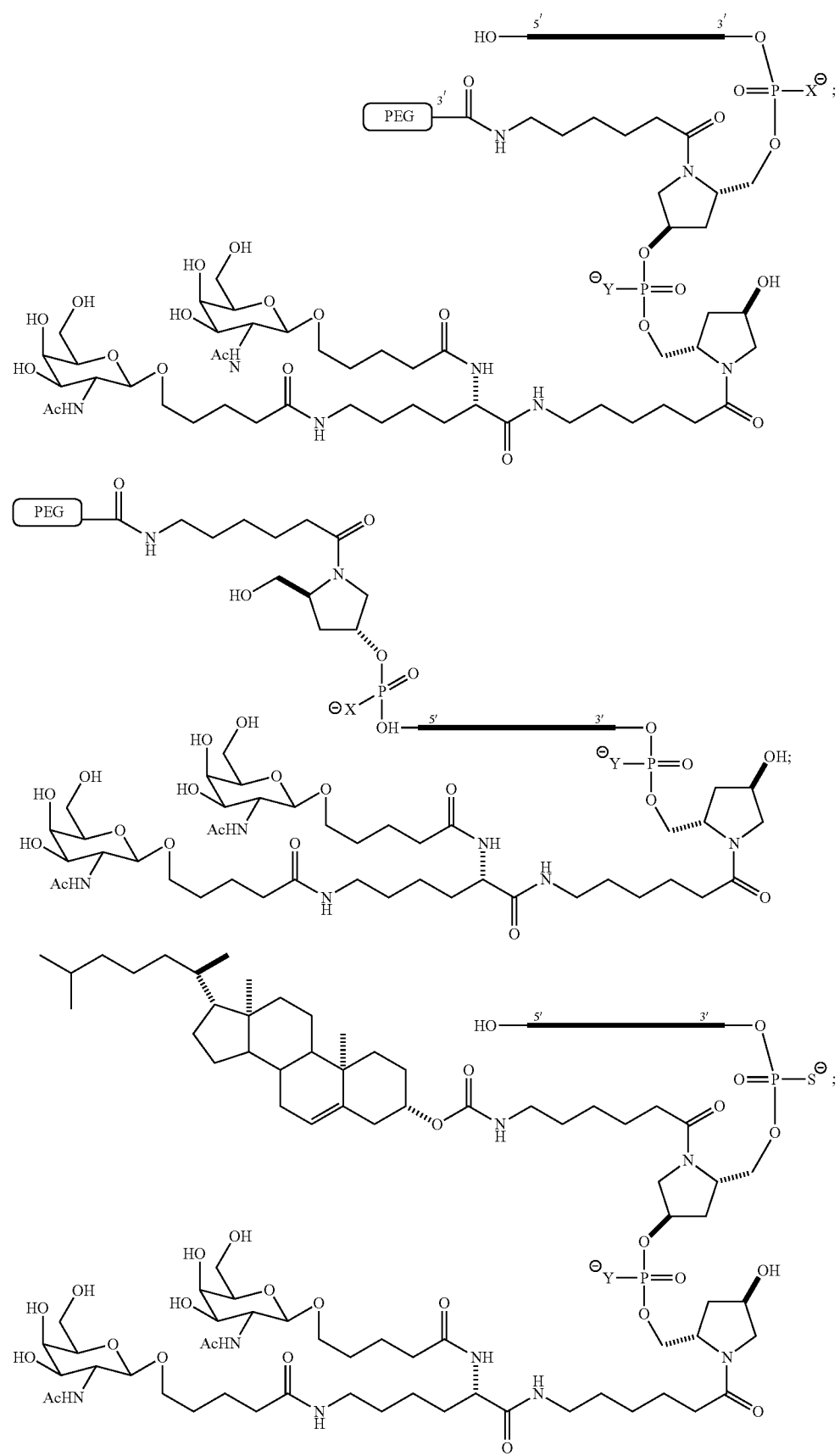

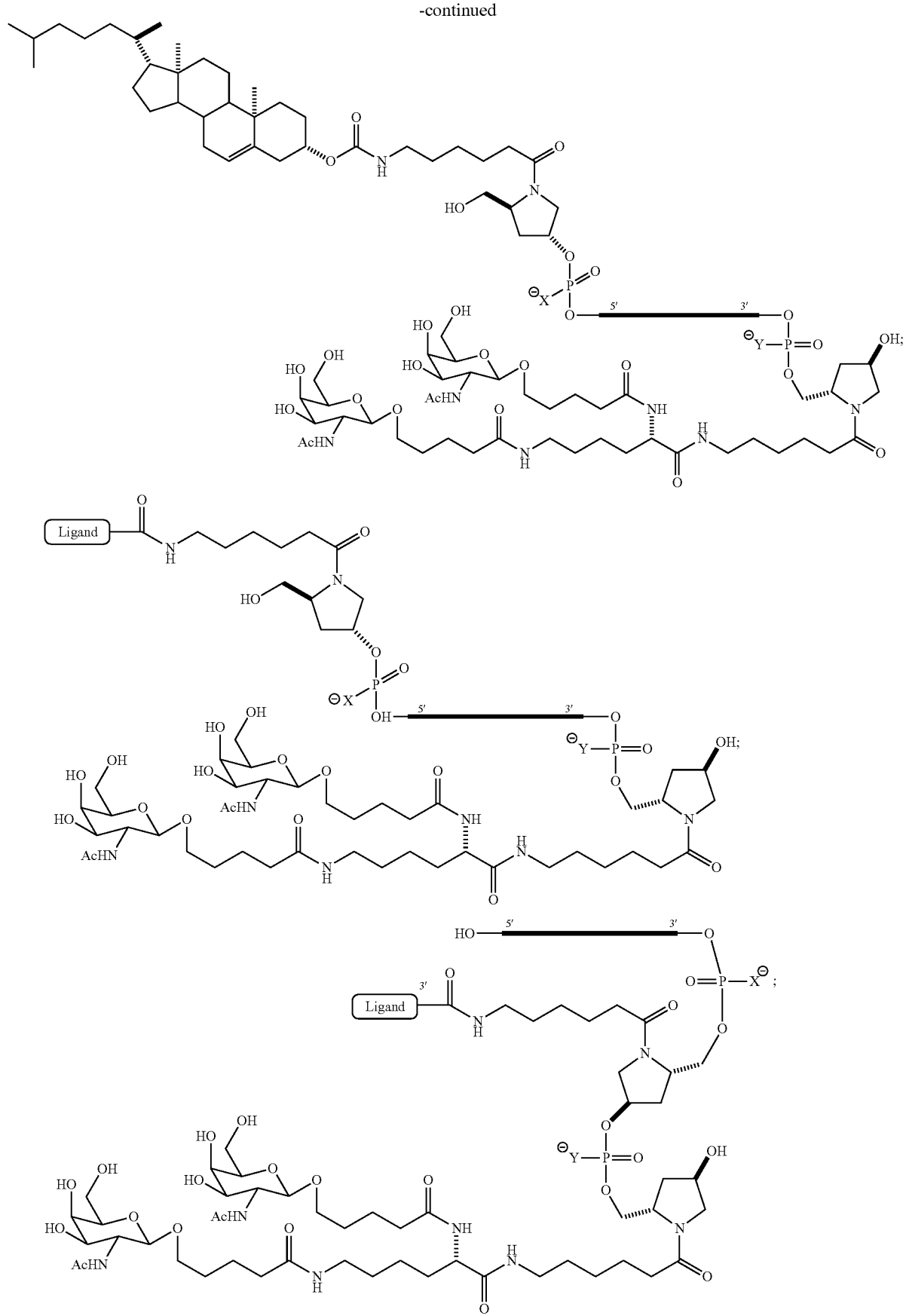

-continued

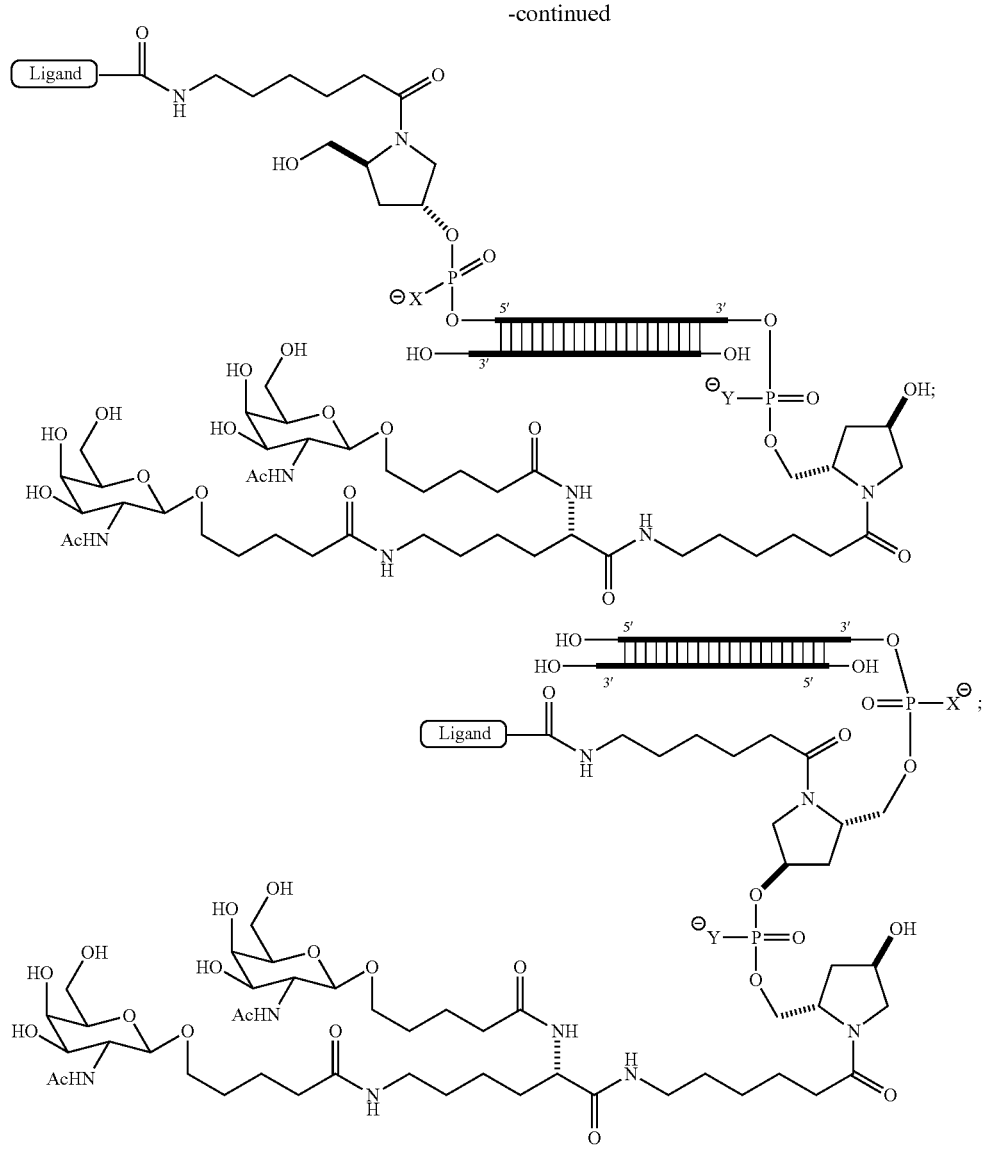

wherein the ligand is a PK modulator: X=O or S; Y=O or S; PEG stands for ω-OH, ω-amino, ω-methoxy, ω-SH, ω-propargyl, ω-azido and ω-ligand PEGS with MW between 200 and 100,000.

Endosomolytic Components

For macromolecular drugs and hydrophilic drug molecules, which cannot easily cross bilayer membranes, entrapment in endosomal/lysosomal compartments of the cell is thought to be the biggest hurdle for effective delivery to their site of action. In recent years, a number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. *Chem. Biol.* 11, 713-723.). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. *Polymers Adv. Technol.* 13, 992-999; Kakudo, Chaki, T., S. et al. (2004). Transferrin-Modified Liposomes Equipped with a pH-Sensitive Fusogenic Peptide: An Artificial Viral-like Delivery System. *Biochemistry* 436, 5618-5628; Yessine, M. A. and Leroux, J. C. (2004). Membrane-destabilizing polyanions: interaction with lipid bilayers and endosomal escape of biomacromolecules. *Adv. Drug Deliv. Rev.* 56, 999-1021; Oliveira, S., van Rooy, I. et al. (2007). Fusogenic peptides enhance endosomal escape improving siRNA-induced silencing of oncogenes. *Int. J. Pharm.* 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs. *Biochim. Biophys. Acta* 1559, 56-68).

In certain embodiments, the endosomolytic components of the present invention may be polyanionic peptides or peptidomimetics which show pH-dependent membrane activity and/or fusogenicity. A peptidomimetic may be a small protein-like chain designed to mimic a peptide. A peptidomimetic may arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Libraries of compounds may be screened for their differential membrane activity at endosomal pH versus neutral pH using a hemolysis assay. Promising candidates isolated by this method may be used as components of the modular compositions of the invention. A method for identifying an endosomolytic component for use in the compositions and methods of the present invention may comprise: providing a library of compounds; contacting blood cells with the members of the library, wherein the pH of the medium in which the contact occurs is controlled; determining whether the compounds induce differential lysis of blood cells at a low pH (e.g., about pH 5-6) versus neutral pH (e.g., about pH 7-8).

Exemplary endosomolytic components include the GALA peptide (Subbarao et al., Biochemistry, 1987, 26: 2964-2972), the EALA peptide (SEQ ID NO: 1) (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of endosomolytic components include $H_2N$ -(AALEALAEALEALAEALE-ALAEAAAAGGC)-$CO_2H$ (SEQ ID NO: 2); $H_2N$ -(AALAEALAEALAEALAEALAEALAAAAGGC)-$CO_2H$ (SEQ ID NO: 3); and $H_2N$ -(ALEALAEALE-ALAEA)-$CONH_2$ (SEQ ID NO: 4).

In certain embodiments, more than one endosomolytic component may be incorporated into the iRNA duplex agent of the invention. In some embodiments, this will entail incorporating more than one of the same endosomolytic component into the iRNA duplex agent in addition to the monomers of formula (I). In other embodiments, this will entail incorporating two or more different endosomolytic components into iRNA duplex agent in addition to the monomers of formula (I).

These endosomolytic components may mediate endosomal escape by, for example, changing conformation at endosomal pH. In certain embodiments, the endosomolytic components may exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH ~7.4).

Fusogenic activity is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

In addition to the hemolysis assay described herein, suitable endosomolytic components can be tested and identified by a skilled artisan using other methods. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an iRNA duplex agent described herein is constructed using one or more test or putative fusogenic agents. The iRNA duplex agent can be labeled for easy visualization. The ability of the endosomolytic component to promote endosomal escape, once the iRNA agent is taken up by the cell, can be evaluated, e.g., by preparation of an endosome preparation, or by microscopy techniques, which enable visualization of the labeled iRNA duplex agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition.

A two-step assay can also be performed, wherein a first assay evaluates the ability of a test compound alone to respond to changes in pH, and a second assay evaluates the ability of a modular composition that includes the test compound to respond to changes in pH.

Peptides

Peptides suitable for use with the present invention can be a natural peptide, e.g. tat or antennopedia peptide, a synthetic peptide or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to the oligonucleotide can affect pharmacokinetic distribution of the oligonucleotide, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 1, for example).

TABLE 1

Exemplary Cell Permeation Peptides

| Cell Permeation Peptide | Amino acid Sequence | Reference |
|---|---|---|
| Penetratin | RQIKIWFQNRRMKWKK | Derossi et al., J. Biol. Chem. 269:10444, 1994 |
| Tat fragment (48-60) | GRKKRRQRRRPPQC | Vives el al., J. Biol. Chem., 272:16010, 1997 |
| Signal Sequence-based peptide | GALFLGWLGAAGSTMGAWSQPKKKRKV | Chaloin et al., Biochem. Biophys. Res. Commun., 243:601, 1998 |
| PVEC | LLIILRRRIRKQAHAHSK | Elmquist et al., Exp. Cell Res., 269:237, 2001 |
| Transportan | GWTLNSAGYLLKINLKALAALAKKIL | Pooga et al., FASEB J., 12:67, 1998 |
| Amphiphilic model peptide | KLALKLALKALKAALKLA | Oehlke et al., Mol. Ther., 2:339, 2000 |
| $Arg_9$ | RRRRRRRRR | Mitchell et al., J. Pept. Res., 56:318, 2000 |
| Bacterial cell wall permeating | KFFKFFKFFK | |
| LL-37 | LLGDFFRKSKEKIGKEFKRIVQRIKDF LRNLVPRTES | |
| Cecropin P1 | SWLSKTAKKLENSAKKRISEGIAIAIQ GGPR | |
| α-defensin | ACYCRIPACIAGERRYGTCIYQGRLW AFCC | |
| b-defensin | DHYNCVSSGGQCLYSACPIFTKIQGTC YRGKAKCCK | |
| Bactenecin | RKCRIVVIRVCR | |
| PR-39 | RRRPRPPYLPRPRPPPFFPPRLPPRIPPG FPPRFPPRFPGKR-NH2 | |
| Indolicidin | ILPWKWPWWPWRR-NH2 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 20). A RFGF analogue (e.g., amino acid sequence AALLPVLLAAP (SEQ ID NO: 21)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 22)) and the Drosophila Antennapedia protein (RQIKIWFQNRRMKWKK (SEQ ID NO: 5)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to the lipid is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting to tumors of a variety of other tissues, including the lung, kidney, spleen, or liver (Aoki et al., Cancer Gene Therapy 8:783-787, 2001). Preferably, the RGD peptide will facilitate targeting of the lipid particle to the kidney. The RGD peptide can be linear or cyclic, and can be modified, e.g., glycosylated or methylated to facilitate targeting to specific tissues. For example, a glycosylated RGD peptide can target a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

iRNA Duplex Agents

The iRNA duplex agent should include a region of sufficient homology to the target gene, and be of sufficient length in terms of nucleotides, such that the iRNA duplex agent, or a fragment thereof, can mediate downregulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA duplex agent is or includes a region which is at least partially, and in some embodiments fully, complementary to the target RNA. It is not necessary that there be perfect complementarity between the iRNA duplex agent and the target, but the correspondence must be sufficient to enable the iRNA duplex agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired some embodiments can include, particularly in the antisense strand, one or more, or for example, 6, 5, 4, 3, 2, or fewer mismatches (with respect to the target RNA). The mismatches, particularly in the antisense strand, are most tolerated in the terminal regions and if present may be in a terminal region or regions, e.g., within 6, 5, 4, or 3 nucleotides of the 5' and/or 3' termini. The sense strand need only be sufficiently complementary with the antisense strand to maintain the over all double stranded character of the molecule.

As discussed elsewhere herein, and in the material incorporated by reference in its entirety, an iRNA duplex agent will often be modified or include nucleoside surrogates. Single stranded regions of an iRNA duplex agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-termini of an iRNA duplex agent, e.g., against exonucleases, or to favor the antisense siRNA agent to enter into RISC are also envisioned. Modifications can include C3 (or C6, C7, C12) amino linkers, thiol linkers, carboxyl linkers, non-nucleotide spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

iRNA duplex agents include: molecules that are long enough to trigger the interferon response (which can be cleaved by Dicer (Bernstein et al. 2001. Nature, 409:363-366) and enter a RISC(RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA duplex agents herein. "siRNA agent or shorter iRNA duplex agent" as used herein, refers to an iRNA duplex agent, e.g., a double stranded RNA agent or single strand agent, that is sufficiently short that it does not induce a deleterious interferon response in a human cell, e.g., it has a duplexed region of less than 60, 50, 40, or 30 nucleotide pairs. The siRNA agent, or a cleavage product thereof, can down regulate a target gene, e.g., by inducing RNAi with respect to a target RNA, wherein the target may comprise an endogenous or pathogen target RNA.

Each strand of an siRNA agent can be equal to or less than 30, 25, 24, 23, 22, 21, or nucleotides in length. The strand may be at least 19 nucleotides in length. For example, each strand can be between 21 and 25 nucleotides in length, siRNA agents may have a duplex region of 17, 18, 19, 29, 21, 22, 23, 24, or 25 nucleotide pairs, and one or more overhangs, or one or two 3' overhangs, of 2-3 nucleotides.

In one embodiment, the iRNA duplex agent is a hairpin. A hair; in iRNA duplex agents will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 12-30, 17 to 23, 19 to 23, and 19 to 21 nucleotides pairs in length. The hairpin may have a single strand overhang or terminal unpaired region, in some embodiments at the 3', and in certain embodiments on the antisense side of the hairpin. In some embodiments, the overhangs are 2-3 nucleotides in length.

The antisense strand of a double stranded iRNA duplex agent may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The sense strand of a double stranded iRNA duplex agent may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded iRNA duplex agent may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 12-30, 17 to 23, 19 to 23, and 19 to 21 nucleotides pairs in length.

In many embodiments, the ds iRNA duplex agent is sufficiently large that it can be cleaved by an endogenous molecule, e.g., by Dicer, to produce smaller ds iRNA duplex agents, e.g., siRNAs agents It may be desirable to modify one or both of the antisense and sense strands of a double strand iRNA duplex agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active siRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional siRNA 5'-end. Antisense strand modifications include 5' phosphorylation as well as any of the other 5' modifications discussed herein, particularly the 5' modifications discussed above in the section on single stranded iRNA molecules.

The sense and antisense strands may be chosen such that the ds iRNA duplex agent includes a single strand or unpaired region at one or both ends of the molecule. Thus, a ds iRNA duplex agent may contain sense and antisense strands, paired to contain an overhang, e.g., one or two 5' or 3' overhangs, or a 3' overhang of 2-3 nucleotides. Many embodiments will have a 3' overhang. Certain siRNA agents will have single-stranded overhangs, in some embodiments 3' overhangs, of 1 or 2 or 3 nucleotides in length at each end. The overhangs can be the result of one strand being longer than the other, or the result of two strands of the same length being staggered. 5' ends may be phosphorylated.

In some embodiments, the length for the duplexed region is between 15 and 30, or 18, 19, 20, 21, 22, and 23 nucleotides in length, e.g., in the siRNA agent range discussed above. siRNA agents can resemble in length and structure the natural Dicer processed products from long dsiRNAs. Embodiments in which the two strands of the siRNA agent are linked, e.g., covalently linked are also included. Hairpin, or other single strand structures which provide the required double stranded region, and a 3' overhang are also within the invention.

The isolated iRNA duplex agents described herein, including ds iRNA duplex agents and siRNA agents can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In one embodiment, an iRNA duplex agent is "sufficiently complementary" to a target RNA, e.g., a target mRNA, such that the iRNA duplex agent silences production of protein encoded by the target mRNA. In another embodiment, the iRNA duplex agent is "exactly complementary" to a target RNA, e.g., the target RNA and the iRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the iRNA duplex agent specifically discriminates a single-nucleotide difference. In this case, the iRNA duplex agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

RNA agents discussed herein include unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The art has often referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA refers to a molecule in which one or more of the components of the nucleic acid, namely sugars, bases, and phosphate moieties, are different from that which occur in nature, for example, different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. In many embodiments of the invention a double stranded iRNA duplex agent, e.g., a partially double stranded iRNA duplex agent, is envisioned. Thus, it is understood that that double stranded structures (e.g., where two separate molecules are contacted to form the double stranded region or where the double stranded region is formed by intramolecular pairing (e.g., a hairpin structure)) made of the single stranded structures described below are within the invention. Lengths are described elsewhere herein.

As nucleic acids are polymers of subunits, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many cases it will not. By way of example, a modification may only occur at a 3' or 5' terminal position, may only occur in a terminal regions, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In some embodiments it is possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

FORMULA (VII)

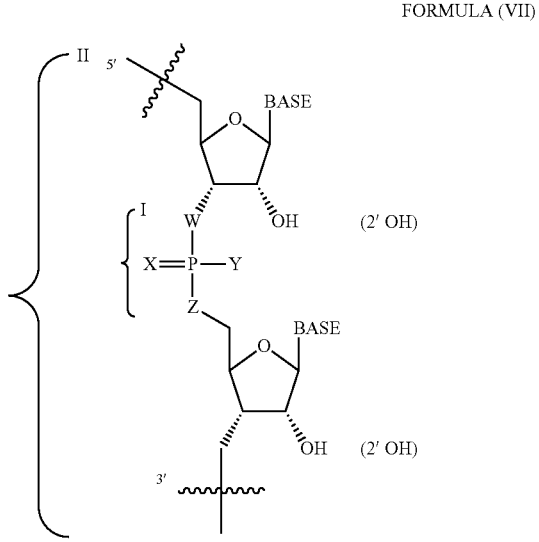

The scaffold presented above in Formula VII represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula VII represents a naturally occurring unmodified oligoribonucleotide.

Unmodified oligoribonucleotides may be less than optimal in some applications, e.g., unmodified oligoribonucleotides can be prone to degradation by e.g., cellular nucleases.

Nucleases can hydrolyze nucleic acid phosphodiester bonds. However, chemical modifications to one or more of the above RNA components can confer improved properties, and, e.g., can render oligoribonucleotides more stable to nucleases.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e., Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g., phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is possible.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is possible.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substitutents of certain embodiments include 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNA's can also include "abasic" sugars, which lack a nucleobase at C—1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

Candidate modifications can be evaluated as described below.

Replacement of the Phosphate Group

The phosphate group can be replaced by non-phosphorus containing connectors (cf Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g., nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. In certain embodiments, PNA surrogates may be used.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA duplex agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)litho-cholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in certain embodiments iRNA duplex agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');
5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)2(O)P-5'-CH2-), 5'-alkyletherphosphonates (R=alkylether=methoxymethyl (MeOCH2-), ethoxymethyl, etc., e.g., RP(OH)(O)—O-5'-).

Terminal modifications can also be useful for increasing resistance to degradation.

Terminal modifications can also be useful for monitoring distribution, and in such cases the groups to be added may include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Candidate modifications can be evaluated as described below.
The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are not used for promoting stability, but they can be useful for other reasons, e.g., some, e.g., 2,6-diaminopurine and 2 amino purine, are fluorescent. Modified bases can reduce target specificity. This may be taken into consideration in the design of iRNA duplex agents.

Candidate modifications can be evaluated as described below.
Evaluation of Candidate RNAs One can evaluate a candidate RNA agent, e.g., a modified RNA, for a selected property by exposing the agent or modified molecule and a control molecule to the appropriate conditions and evaluating for the presence of the selected property. For example, resistance to a degradent can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dsiRNA agents.

In an alternative functional assay, a candidate dsiRNA agent homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dsiRNA agent would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added and/or cells in which a non-modified RNA is added.

DEFINITIONS

The term "halo" refers to any radical of fluorine, chlorine, bromine or iodine. The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituted" refers to the replacement of one or more hydrogen radicals in a given structure with the radical of a specified substituent including, but not limited to:

halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Palindromes

The iRNA duplex agents of the invention can target more than one RNA region. For example, an iRNA duplex agent can include a first and second sequence that are sufficiently complementary to each other to hybridize. The first sequence can be complementary to a first target RNA region and the second sequence can be complementary to a second target RNA region. The first and second sequences of the iRNA duplex agent can be on different RNA strands, and the mismatch between the first and second sequences can be less than 50%, 40%, 30%, 20%, 10%, 5%, or 1%. The first and second sequences of the iRNA duplex agent are on the same RNA strand, and in a related embodiment more than 50%, 60%, 70%, 80%, 90%, 95%, or 1% of the iRNA duplex agent can be in bimolecular form. The first and second sequences of the iRNA duplex agent can be fully complementary to each other.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The compositions of the invention can include mixtures of iRNA duplex agent molecules. For example, one iRNA duplex agent can contain a first sequence and a second sequence sufficiently complementary to each other to hybridize, and in addition the first sequence is complementary to a first target RNA region and the second sequence is complementary to a second target RNA region. The mixture can also include at least one additional iRNA duplex agent variety that includes a third sequence and a fourth sequence sufficiently complementary to each other to hybridize, and where the third sequence is complementary to a third target RNA region and the fourth sequence is complementary to a fourth target RNA region. In addition, the first or second sequence can be sufficiently complementary to the third or fourth sequence to be capable of hybridizing to each other. The first and second sequences can be on the same or different RNA strands, and the third and fourth sequences can be on the same or different RNA strands.

The target RNA regions can be variant sequences of a viral or human RNA, and in certain embodiments, at least two of the target RNA regions can be on variant transcripts of an oncogene or tumor suppressor gene. The target RNA regions can correspond to genetic hot-spots.

Methods of making an iRNA duplex agent composition can include obtaining or providing information about a region of an RNA of a target gene (e.g., a viral or human gene, or an oncogene or tumor suppressor, e.g., p53), where the region has high variability or mutational frequency (e.g., in humans). In addition, information about a plurality of RNA targets within the region can be obtained or provided, where each RNA target corresponds to a different variant or mutant of the gene (e.g., a region including the codon encoding p53 248Q and/or p53 249S). The iRNA duplex agent can be constructed such that a first sequence is complementary to a first of the plurality of variant RNA targets (e.g., encoding 249Q) and a second sequence is complementary to a second of the plurality of variant RNA targets (e.g., encoding 249S), and the first and second sequences can be sufficiently complementary to hybridize.

Sequence analysis, e.g., to identify common mutants in the target gene, can be used to identify a region of the target gene that has high variability or mutational frequency. A region of the target gene having high variability or mutational frequency can be identified by obtaining or providing genotype information about the target gene from a population.

Expression of a target gene can be modulated, e.g., downregulated or silenced, by providing an iRNA duplex agent that has a first sequence and a second sequence sufficiently complementary to each other to hybridize. In addition, the first sequence can be complementary to a first target RNA region and the second sequence can be complementary to a second target RNA region.

An iRNA duplex agent can include a first sequence complementary to a first variant RNA target region and a second sequence complementary to a second variant RNA target region. The first and second variant RNA target regions can correspond to first and second variants or mutants of a target gene, e.g., viral gene, tumor suppressor or oncogene. The first and second variant target RNA regions can include allelic variants, mutations (e.g., point mutations), or polymorphisms of the target gene. The first and second variant RNA target regions can correspond to genetic hot-spots.

A plurality of iRNA duplex agents (e.g., a panel or bank) can be provided.

OTHER EMBODIMENTS

In yet another embodiment, iRNAs agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a iRNA duplex agent and one that produces a transcript that includes the bottom strand of a iRNA duplex agent. When the templates are transcribed, the iRNA duplex agent is produced, and processed into siRNA agent fragments that mediate gene silencing.

Physiological Effects

The iRNA duplex agents described herein can be designed such that determining therapeutic toxicity is made easier by the complementarity of the iRNA duplex agent with both a human and a non-human animal sequence. By these methods, an iRNA duplex agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, Pan paniscus, Pan troglodytes, Macaca mulatto, or Cynomolgus monkey. The sequence of the iRNA duplex agent could be complementary to sequences within homologous genes, e.g., oncogenes or tumor suppressor genes, of the non-human mammal and the human. By determining the toxicity of the iRNA duplex agent in the non-human mammal, one can extrapolate the toxicity of the iRNA duplex agent in a human. For a more strenuous toxicity test, the iRNA duplex agent can be complementary to a human and more than one, e.g., two or three or more, non-human animals.

The methods described herein can be used to correlate any physiological effect of an iRNA duplex agent on a human, e.g., any unwanted effect, such as a toxic effect, or any positive, or desired effect.

A iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

Routes of Delivery

A composition that includes a iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering an iRNA duplex agent, e.g., a siRNA agent, to a subject (e.g., a human subject). The method includes administering a unit dose of the iRNA duplex agent, e.g., a siRNA agent, e.g., double stranded siRNA agent that (a) the double-stranded part is 19-25 nucleotides (nt) long, for example, 21-23 nt, (b) is complementary to a target RNA (e.g., an endogenous or pathogen target RNA), and, optionally, (c) includes at least one 3' overhang 1-5 nucleotide long. In one embodiment, the unit dose is less than 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous or intramuscular), an inhaled dose, or a topical application. In some embodiments dosages may be less than 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than an iRNA duplex agent, e.g., other than a siRNA agent. In another embodiment, the subject has atherosclerosis and the effective dose of an iRNA duplex agent, e.g., a siRNA agent, is administered in combination with, e.g., after surgical intervention, e.g., angioplasty.

In one embodiment, a subject is administered an initial dose and one or more maintenance doses of an iRNA duplex agent, e.g., a siRNA agent, (e.g., a precursor, e.g., a larger iRNA duplex agent which can be processed into a siRNA agent, or a DNA which encodes an iRNA duplex agent, e.g., a siRNA agent, or precursor thereof). The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are, for example, administered no more than once every 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the composition includes a plurality of iRNA duplex agent species. In another embodiment, the iRNA duplex agent species has sequences that are non-overlapping and non-adjacent to another species with respect to a naturally occurring target sequence. In another embodiment, the plurality of iRNA duplex agent species is specific for different naturally occurring target genes. In another embodiment, the iRNA duplex agent is allele specific.

The inventors have discovered that iRNA duplex agents described herein can be administered to mammals, particularly large mammals such as nonhuman primates or humans in a number of ways.

In one embodiment, the administration of the iRNA duplex agent, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of iRNA duplex agents described herein.

Accordingly, an iRNA duplex agent, e.g., a siRNA agent, (e.g., a precursor, e.g., a larger iRNA duplex agent which can be processed into a siRNA agent, or a DNA which encodes a an iRNA duplex agent, e.g., a siRNA agent, or precursor thereof) described herein, e.g., a therapeutically effective amount of a iRNA duplex agent described herein, e.g., a iRNA duplex agent having a double stranded region of less than 40, and, for example, less than 30 nucleotides and having one or two 1-3 nucleotide single strand 3' overhangs can be administered rectally, e.g., introduced through the rectum into the lower or upper colon. This approach is particularly useful in the treatment of, inflammatory disorders, disorders characterized by unwanted cell proliferation, e.g., polyps, or colon cancer.

In one aspect the invention provides a method of modulating the expression of a target gene in a cell, comprising providing to said cell an iRNA duplex agent of this invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21 (WAF1/CIP1) gene, mutations in the p27 (KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

The invention is further illustrated by the following examples, which should not be construed as further limiting. The contents of all references, pending patent applications and published patents, cited throughout this application are hereby expressly incorporated by reference.

EXAMPLES

Example 1

Synthesis of Carbohydrate Conjugate Building Blocks 110 and 112

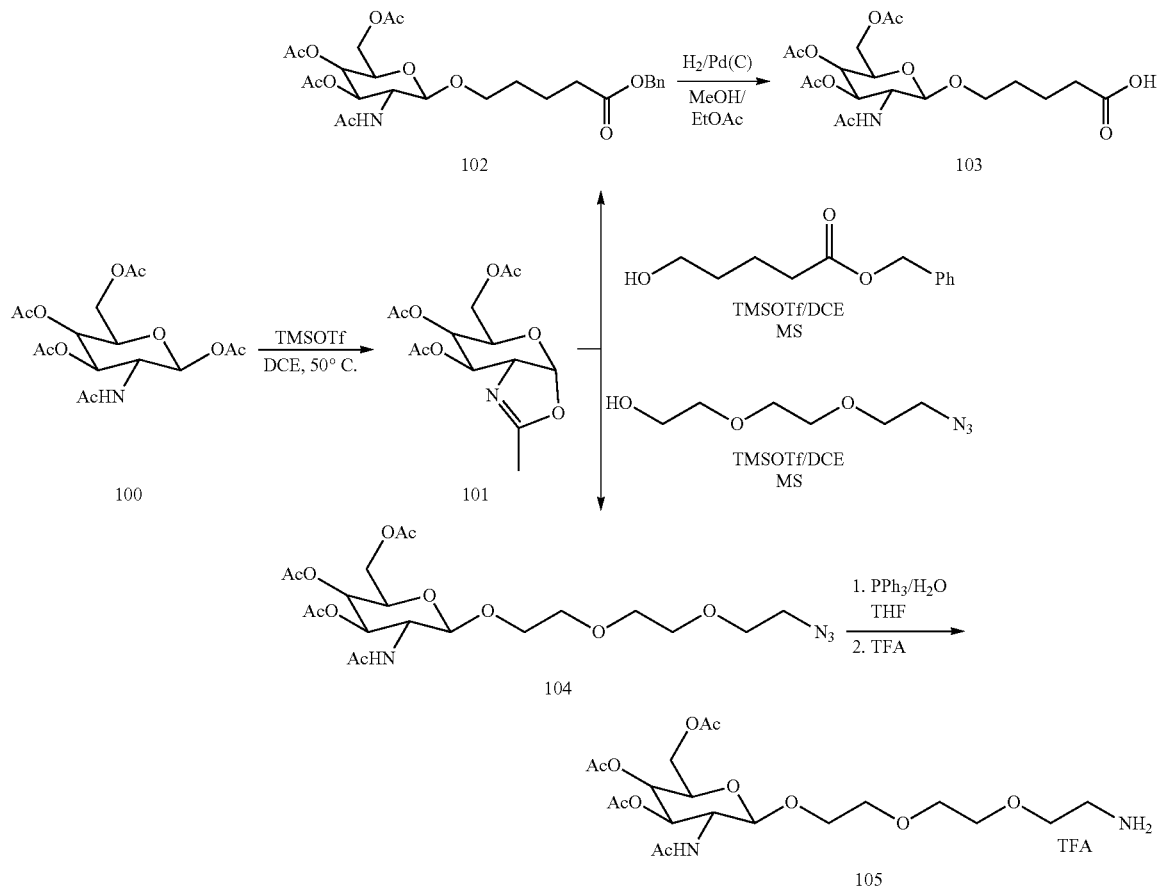

Preparation of 101: Galactosamine pentaacetate 100 (52.00 g, 133.63 mmol) was taken in dichloroethane (300 mL) at ambient temperature. TMSOTf (44.55 g, 200.44 mmol) was added that and the mixture stirred at 50 C for 90 minutes in a water bath, heating stopped and the mixture stirred overnight at room temperature. It was poured in to an ice cold sodium bicarbonate solution; extracted with dichloromethane, washed with water and dried over sodium sulfate. Solvents were removed the residue dried under high vacuum overnight to get the compound as dark gum (44.50 g, quantitative). It was used for next reaction with out any further purification. $^1$H NMR and MALDI confirmed the product formation. MS: Calculated for $C_{14}H_{19}NO_8$, 329.11. Found 352.1 (M+Na).

Preparation of 102: Compound 101 (43.70 g, 133.56 mmol) and the benzyl ester (41.71 g, 200.34 mmol) were dissolved in dichloroethane (300 mL), molecular sieves (50 g) was added to that and stirred for 30 minutes. TMSOTf (14.50 g, 66.78 mmol) was added to that and the mixture stirred for overnight at room temperature. It was poured in to an ice cold solution of sodium bicarbonate and extracted with dichloromethane, washed with water and dried over sodium sulfate. Solvents were removed and the residue purified by chromatography (gradient elution: 20-100% ethylacetate/hexanes) to get the required compound as light brown gummy liquid (60.50 g, 86%). 1HNMR, $^{13}$CNMR MS: Calculated for $C_{26}H_{35}NO_{11}$, 537.22. Found 560.21 (M+Na).

Preparation 103: Compound 102 (60.00 g, 111.68 mmol) was dissolved in a mixture of Methanol/ethylacetate and degassed with argon. Pd/C (6.00 g, 10 wt % Degussa, wet type) was added and hydrogenated under balloon pressure overnight. Filtered through a small pad of celite; washed with methanol and dried under high vacuum overnight to get the product (48.85 g, 98%). 1HNMR, $^{13}$CNMR MS: Calculated for $C_{19}H_{29}NO_{11}$, 447.17. Found 469.9 (M+Na).

Preparation of 104: Compound 101 (42.30 g, 128.43 mmol) and the azido ethanol (26 g, 192.45 mmol) were dissolved in dichloroethane (300 mL), molecular sieves (50 g) were added to that and stirred for 30 minutes. TMSOTf (14.29 g, 64.21 mmol) was added to that and the mixture stirred for overnight at room temperature. It was poured in to an ice cold solution of sodium bicarbonate and extracted with dichloromethane, washed with water and dried over sodium sulfate. Solvents were removed and the residue purified by chromatography (gradient elution: 20-100% ethyl acetate/hexanes, followed by 5-10% Methanol/ethylacetate) to get the required compound as light brown gummy liquid (59.23 g, 91.00%). 1HNMR, $^{13}$CNMR MS: Calculated for $C_{20}H_{32}N_4O_{11}$, 504.21. Found 527.1 (M+Na).

Preparation of 105: Compound 104 (9.33 g, 18.50 mmol) was dissolved in THF (100 mL) to that $PPh_3$ (5.97 g, 22.2 mmol) was added and the mixture stirred for 48 h. TLC checked to see complete disappearance of starting material. Water (1 mL, 55 mmol) and stirred for another 24 h. TFA (2.85 mL, 23.12 mmol) and toluene (40 mL) were added and the solvents were removed under reduced pressure. The residue was co-evaporated with toluene (2×40 mL) two times and dried under high vacuum. It was used for the next reaction in the same day. MS: Calculated for $C_{20}H_{34}N_2O_{11}$, 478.22. Found 500.8 (M+Na).

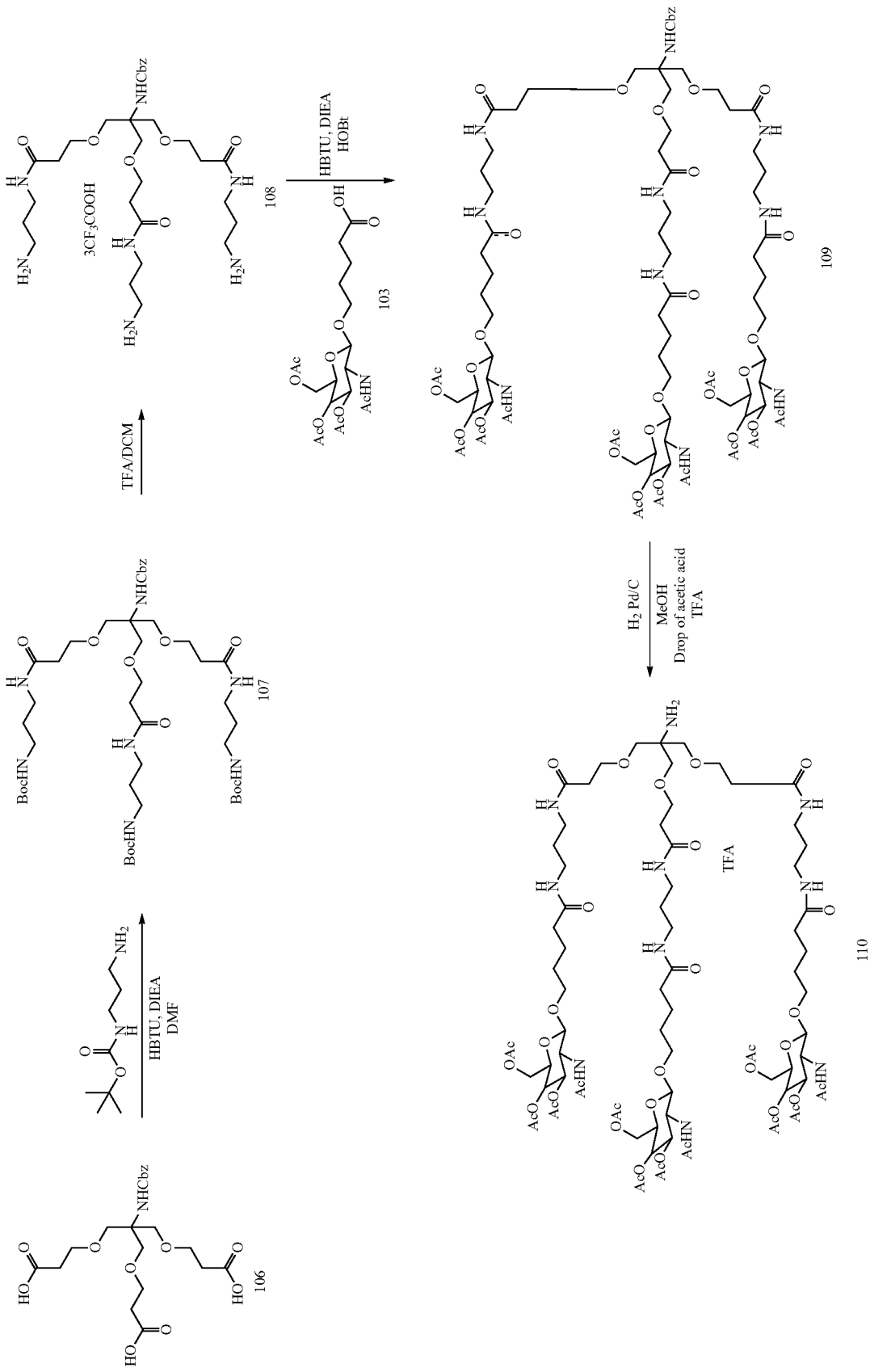

Preparation of 107: Compound 106 (JOC 2002) (6.94 g, 14.73 mmol) and monoboc propyl amine (10.26 g, 58.89 mmol) were dissolved in DMF (100 mL), to that HBTU (17.26 g, 45.50 mmol) and DIEA (15.36 mL, 88.14 mmol) were added and stirred overnight. Reaction mixture was poured in to ice-water mixture and extracted with dichloromethane, washed with sodium bicarbonate solution, brine and dried over sodium sulfate. Solvents were removed and the residue was purified by chromatography (Ethyl acetate, followed by 2-10% MeOH/DCM) to get the product as white fluffy solid (10.49 g, 76%). MS: Calculated for $C_{45}H_{77}N_7O_{14}$, 939.55. Found 940.53 (M+H).

Preparation of 108: Compound 107 (2.40 g, 2.56 mmol) was dissolved in dichloromethane (10 mL), to that a mixture of TFA/DCM (1:4, 10 mL) was added and stirred for 30 minutes. Reaction was monitored by mass spectra. 100 mL of toluene was added and removed the solvent under reduced pressure. The residue was co-evaporated two times with toluene (2×100 mL) and dried under high vacuum to get the compound as its TFA salt (white gum, 2.47 g, 99%). It was used for the next reaction with out any further purification. MS: Calculated for $C_{30}H_{53}N_7O_8$, 639.40. Found 640.45 (M+H).

Preparation of 109: GalNAc acid 103 (4.00 g, 8.99 mmol) was dissolved in DMF (50 mL); HBTU (3.75 g, 9.88 mmol), HOBt (1.34 g, 9.88 mmol) and DIEA (5 mL, 3.2 eq) was added to that and stirred for 3-4 minutes. A solution of 108 (2.47 g, 2.50 mmol) in DMF was added to that and stirred the reaction mixture overnight. TLC was checked, solvents were removed under reduced pressure. The residue was dissolved in dichloromethane, washed with sodium bicarbonate solution (50 mL), water (100 mL) and dried over sodium sulfate. Solvents were removed and the residue was purified by chromatography (ethyl acetate, followed by gradient elution 5-15% MeOH/DCM) to get the product 109 as a white solid (4.20 g, 87%). MS: Calculated for $C_{87}H_{134}N_{10}O3_8$, 1926.89. Found 1949.5 (M+Na).

Preparation of 110: GalNAc derivative 109 (7.50 g, 4.18 mmol) was taken in methanol (50 mL) degassed with argon. Pd/C (0.800 g, 10 wt % Degussa type wet) and couple of drops of acetic acid were added; the mixture was hydrogenated under balloon pressure overnight. Reaction mixture was filtered through a small pad of celite, washed with methanol. TFA (0.465 mL, 5.22 mmol) was added and removed the solvent under reduced pressure. The residue was co-evaporated with toluene (2 times) and dried under high vacuum overnight to get the compound as TFA salt (pale yellow solid, 7.30 g, 99%). MS: Calculated for $C_{79}H_{128}N_{10}O_{36}$, 1792.85. Found 1815.9 (M+Na).

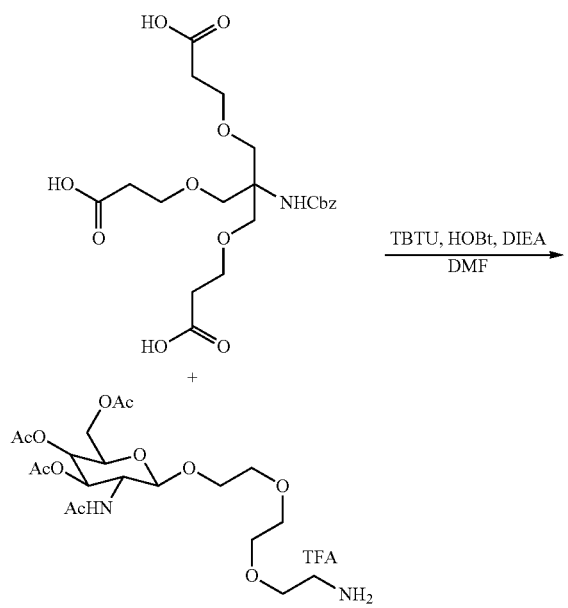

105

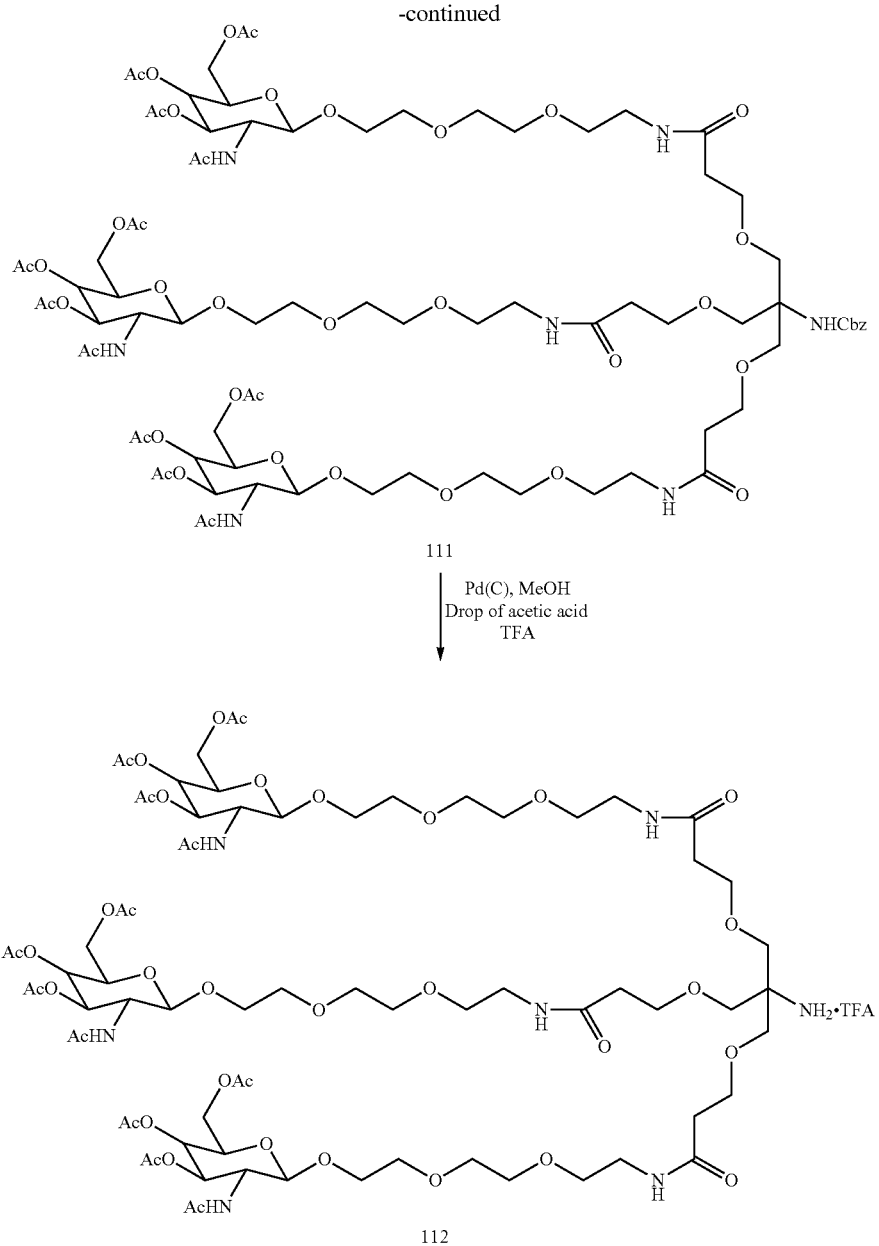

111

Pd(C), MeOH
Drop of acetic acid
TFA

112

Preparation of 111: The tricarboxylic acid 106 (2.17 g, 4.625 mmol) and amine (18.50 mmol, crude from previous reaction) was dissolved in DMF (100 mL). To that TBTU (5.34 g, 16.63 mmol), HOBt (2.24 g, 16.59 mmol) and DIEA (5.64 mL, 32.36 mmol) was added and stirred the reaction mixture for 24 h. After stirring 24 hrs an additional amount of DIEA (4 mL) was added continued stirring. After 48 hrs solvents were removed under reduced pressure, the residue was dissolved in dichloromethane, washed with 1M phosphoric acid solution, sodium bicarbonate solution, water and dried over sodium sulfate. Solvents were removed and the residue was purified by chromatography (ethyl acetate, followed by 3-15% MeOH/DCM) to get the required compound III as a white solid (5.80 g, 68%) MS: Calculated for $C_{81}H_{125}N_7O_{41}$, 1851.79. Found 1874.20 (M+Na).

Preparation of 112: GalNAc derivative 111 (5.75 g, 3.09 mmol) was taken in methanol (100 mL) degassed with argon. Pd/C (0.600 g, 10 wt % Degussa type wet) and couple of drops of acetic acid were added; the mixture was hydrogenated under balloon pressure for 36 hrs. Reaction mixture was filtered through a small pad of celite, washed with methanol. TFA (0.354 mL, 1.25 eq) and toluene (30 mL) was added and removed the solvent under reduced pressure. The residue was co-evaporated with toluene (2 times) and dried under high vacuum overnight to get the compound as TFA salt (5.70 g, crude). MS: Calculated for $C_{81}H_{125}N_7O_{41}$, 1717.75. Found 1740.5 (M+Na).

Example 2
Synthesis of Carbohydrate Conjugate 118
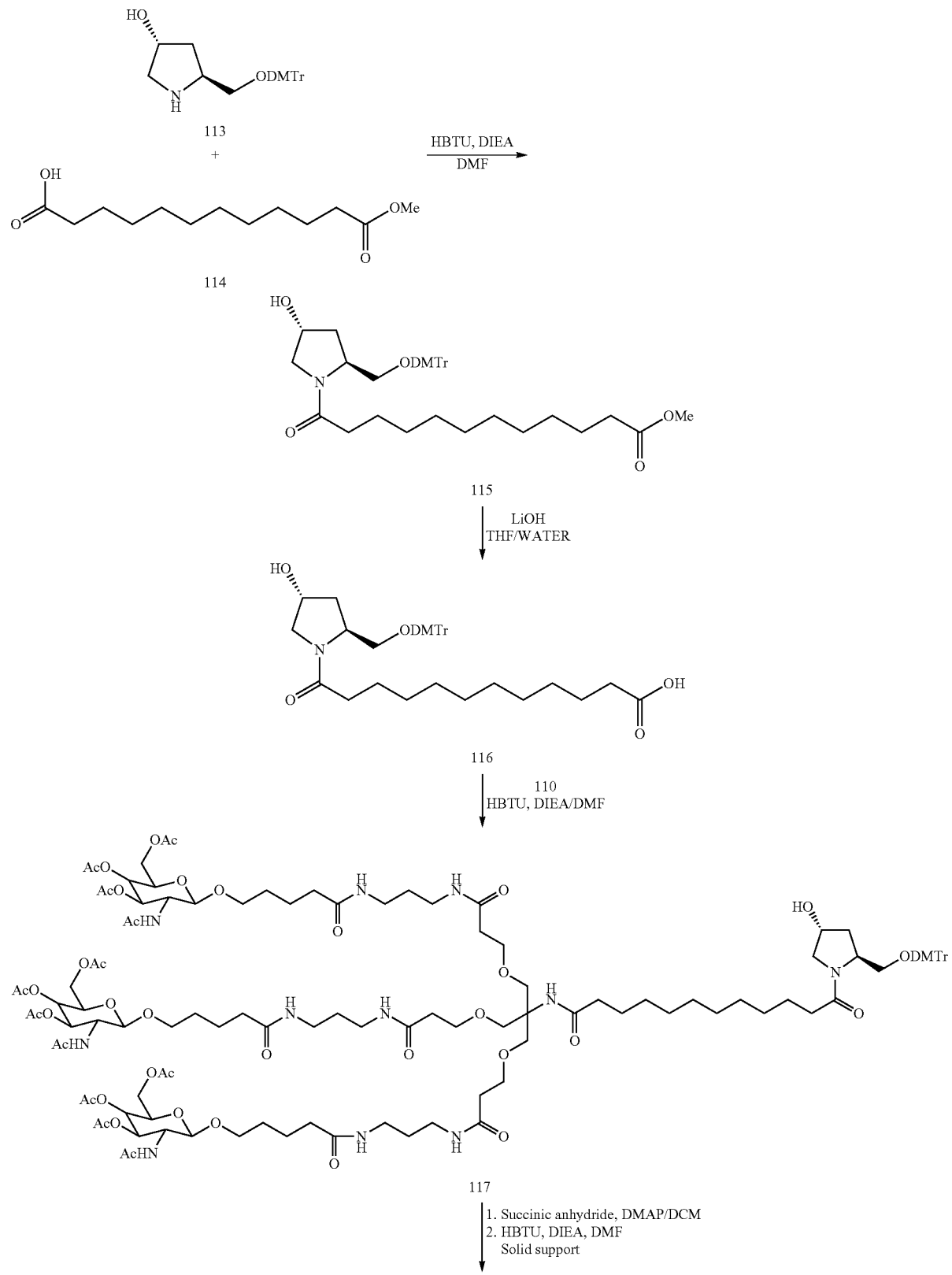

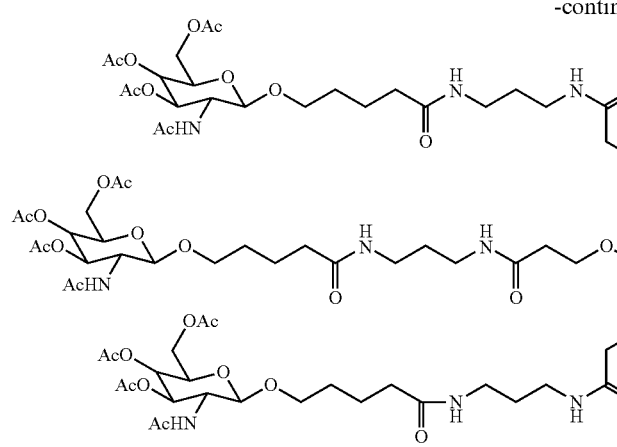
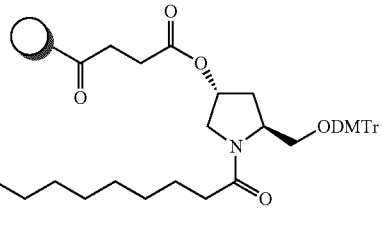

118

Preparation of 115: Hydroxy proline amine (3.00 g, 7.15 mmol) and Dodecanedioic acid mono methyl ester (1.748 g, 7.15 mmol) were taken together in DMF (50 mL). To that HBTU (3.25 g, 8.56 mmol) and DIEA (3.7 mL, 21.24 mmol) were added and stirred the reaction over night. The reaction mixture was poured in to ice water mixture and extracted with DCM. Washed with bicarbonate solution, water, brine and dried over sodium sulfate. Solvent was removed and the residue was purified by chromatography (eluted with 50% ethyl acetate/hexane, ethyl acetate, followed by 5% MeOH/DCM) to get the required compound 115 as white solid (4.30 g, 93%). MS: Calculated for $C_{39}H_{51}NO_7$, 645.37. Found 646.35 (M+H).

Preparation of 116: Compound 115 (4.25 g, 6.58 mmol) was dissolved in a mixture of THF/DCM/Water (50 mL, 2:1:1). LiOH (1.90 g, 45.2 mmol) was added and the mixture stirred overnight. TLC checked, acetic acid was added to neutralize the reaction mixture. Solvent was removed and the residue extracted with DCM. TEA (excess) added to the DCM solution and filtered the solution through a small pad of silica gel to get the required product 116 as its TEA salt (4.15 g, 86%). MS: Calculated for $C_{38}H_{49}NO_7$, 631.35. Found 630.34 (M–H).

Preparation of 117: Compound 116 (1.30 g, 2.06 mmol) and HBTU (0.821 g, 1.05 eq.) were taken together in DMF (30 mL). To that DIEA (1.07 ml, 3 eq) was added and stirred the reaction mixture for 3-4 minutes. A solution of amine 110 (3.00 g, 1.58 mmol) was added followed by 1 eq. DIEA. The reaction mixture stirred overnight at room temperature. Solvents were removed under reduced pressure. The residue dissolved in DCM, washed with bicarbonate and water. DCM layer was dried over sodium sulfate and removed the solvents. The residue was purified by chromatography (eluted first with ethyl acetate, followed by 5-20% MeOH/DCM) to get the product 117 as white solid (3.35 g, 88%). MS: Calculated for $C_{117}H_{175}N_{11}O_{42}$, 2406.19. Found 2429.10 (M+Na).

Preparation of Solid Support 118: Compound 117 (3.30 g, 1.37 mol), succinic anhydride (0.274 g, 2 eq) and DMAP (0.501 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid (3.81 g) as its TEA salt. MS: Calculated for $C_{121}H_{179}N_{11}O_{45}$, 2506.21. Found 2529.20 (M+Na). Succinate (2.20 g, 0.877 mmol) and HBTU (0.334 g, 0.877 mmol) were dissolved in DMF (100 mL). To that DIEA (0.457 mL, 2.62 mmol) was added and swirl the reaction for 3-4 minutes. Polystyrene support (12.30 g) was added to that and shaken the mixture for 24 hrs. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 118 (13.10 g, 50.5 mol/g loading).

Example 3

Synthesis of Carbohydrate Conjugate 122

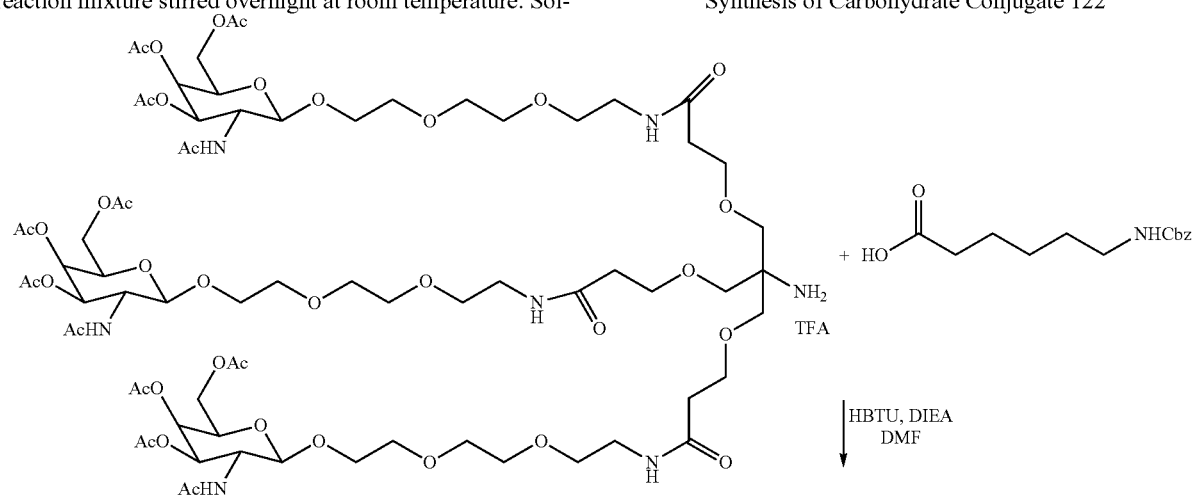

112

-continued

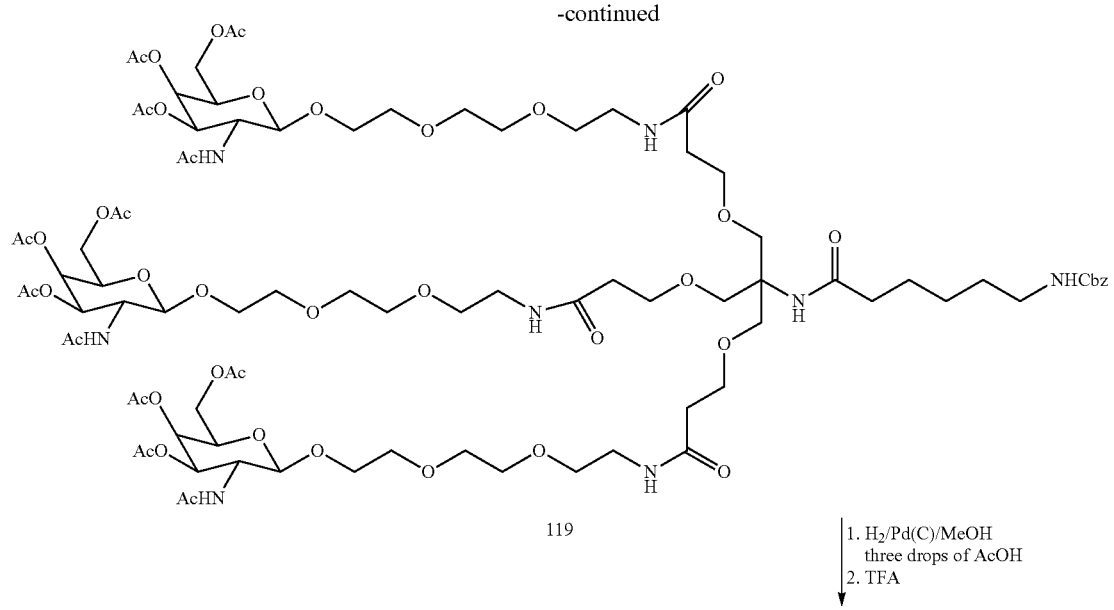

119

1. H₂/Pd(C)/MeOH
   three drops of AcOH
2. TFA

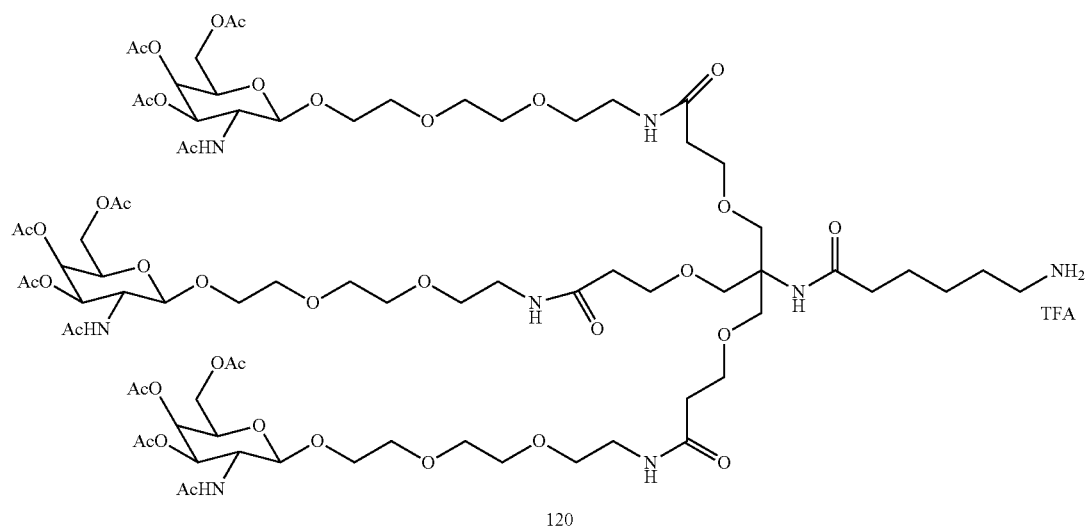

120

Preparation of 119: Z-amino caproic acid (2.19 g, 8.25 mmol) was dissolved in DMF (50 mL). To that HBTU (3.13 g, 8.25 mmol) and DIEA (7.19 mL, 5.00 eq.) was added and stirred the mixture for few minutes. GalNAc amine 112 (10.10 g, 5.52 mmol) was dissolved in 50 ml of DMF was added to that and stirred for 48 hrs. TLC and MALDI were checked for product formation. Solvents were removed and the residue was dissolved in DCM, washed with NaHCO₃ solution and water. Dried over sodium sulfate and removed the solvents under reduced pressure. Residue was purified by chromatography (eluted with ethyl acetate, followed by gradient elution of 5-15% MeOH/DCM) to get the required compound 119 as off white solid (6.20 g, 57%). MS: Calculated for $C_{87}H_{136}N_8O_{42}$, 1964.88. Found 1987.75 (M+Na).

Preparation of 120: Compound 119 (6.100 g, 3.10 mmol) was dissolved in Methanol (50 mL), to that 1 mL of acetic acid was added. Degassed the reaction mixture, Pd/C (0.700 g, 10 wt % Degussa wet type) was added to that and hydrogenated under balloon pressure for 36 hrs. Reaction mixture was filtered through a small pad of celite, washed with MeOH. To that 1.25 eq of TFA and toluene (50 mL) were added and removed solvents under reduced pressure. The residue was co-evaporated with toluene two times and dried under high vacuum overnight night to get the required compound as an off white solid (6.10 g, quantitative). This compound used as such for the next reaction with out any further purification. MS: Calculated for $C_{79}H_{130}N_8O_{40}$, 1830.84. Found 1853.81 (M+Na).

101
102
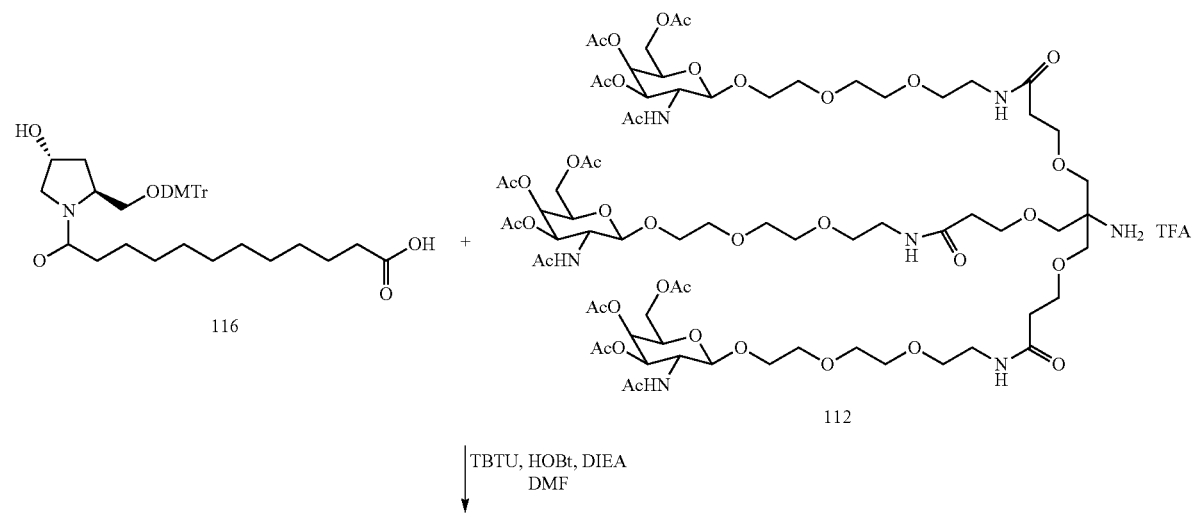
↓ TBTU, HOBt, DIEA
    DMF
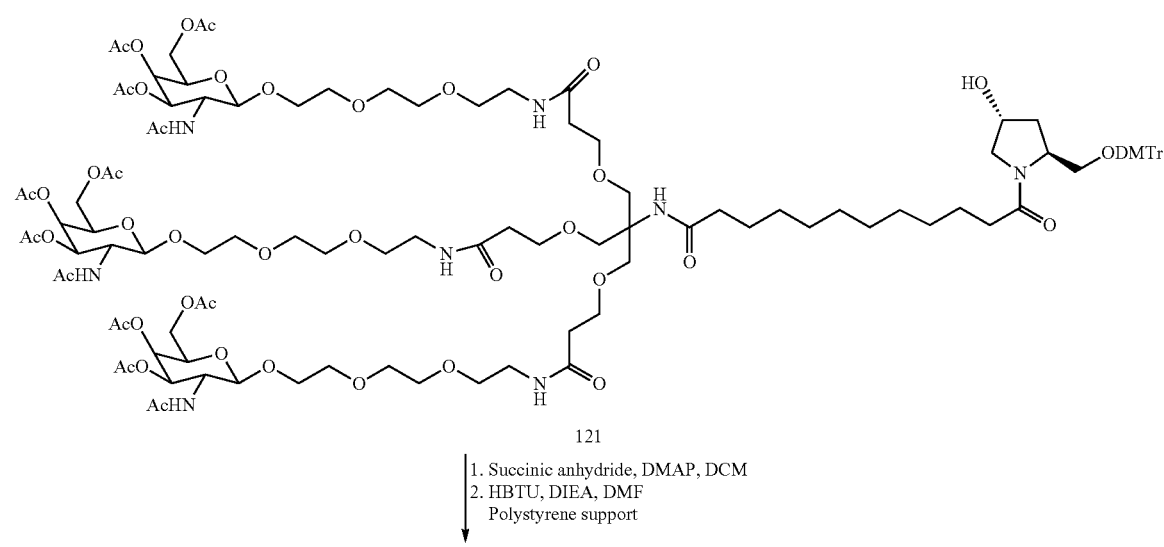
1. Succinic anhydride, DMAP, DCM
2. HBTU, DIEA, DMF
   Polystyrene support
↓
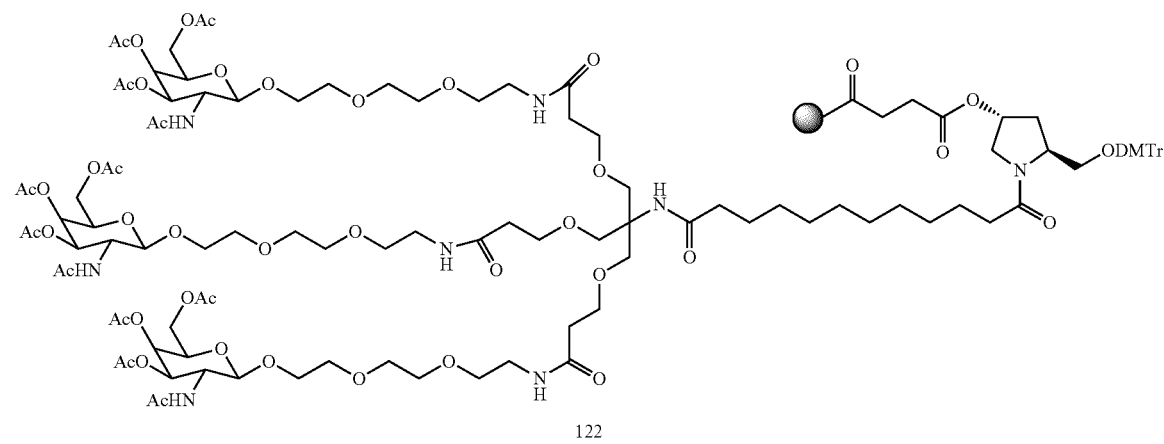

Preparation of 121: Compound 116 (5.06 g, 6.90 mmol), GalNAc amine 112 (10.55 g, 5.756 mmol) TBTU (2.44 g, 1.1 eq.) and HOBt (1.025 g, 1.1 eq) were taken together in DMF (100 mL). To that DIEA (6 mL ml, 34.51 mmol) was added and stirred the reaction mixture for 48 hrs. Reaction was monitored by TCL as well as MALDI. Solvents were removed under reduced pressure. The residue dissolved in DCM, washed with bicarbonate and water. DCM layer was dried over sodium sulfate and removed the solvents. The residue was purified by chromatography (eluted first with ethyl acetate, followed by 3-10% MeOH/DCM) to get the product 121 as off white solid (10.50 g, 79%). MS: Calculated for $C_{111}H_{166}N_8O_{45}$, 2331.09. Found 2354.03 (M+Na).

Preparation of 122: Compound 121 (2.00 g, 0.857 mmol), succinic anhydride (0.186 g, 2 eq), DMAP (0.314 g, 3 eq.) are taken together in DCM and stir overnight. Solvent is removed and the residue filter through a small pad of silica gel to get the succinate as its TEA salt. Succinate (2.00 g, 0.857 mmol) and HBTU (0.325 g, 0.857 mmol) are dissolved in DMF (100 mL). To that DIEA (0.450 mL, 2.57 mmol) is added and swirl the reaction for 3-4 minutes. Polystyrene support (10.00 g) is added to that and shaken the mixture for 24 hrs. Filter through a frit and washed with DCM, 10% MeOH/DCM, DCM and ether, it is capped with acetic anhydride to get the solid support 122.

Example 4

Synthesis of Carbohydrate Conjugate 128

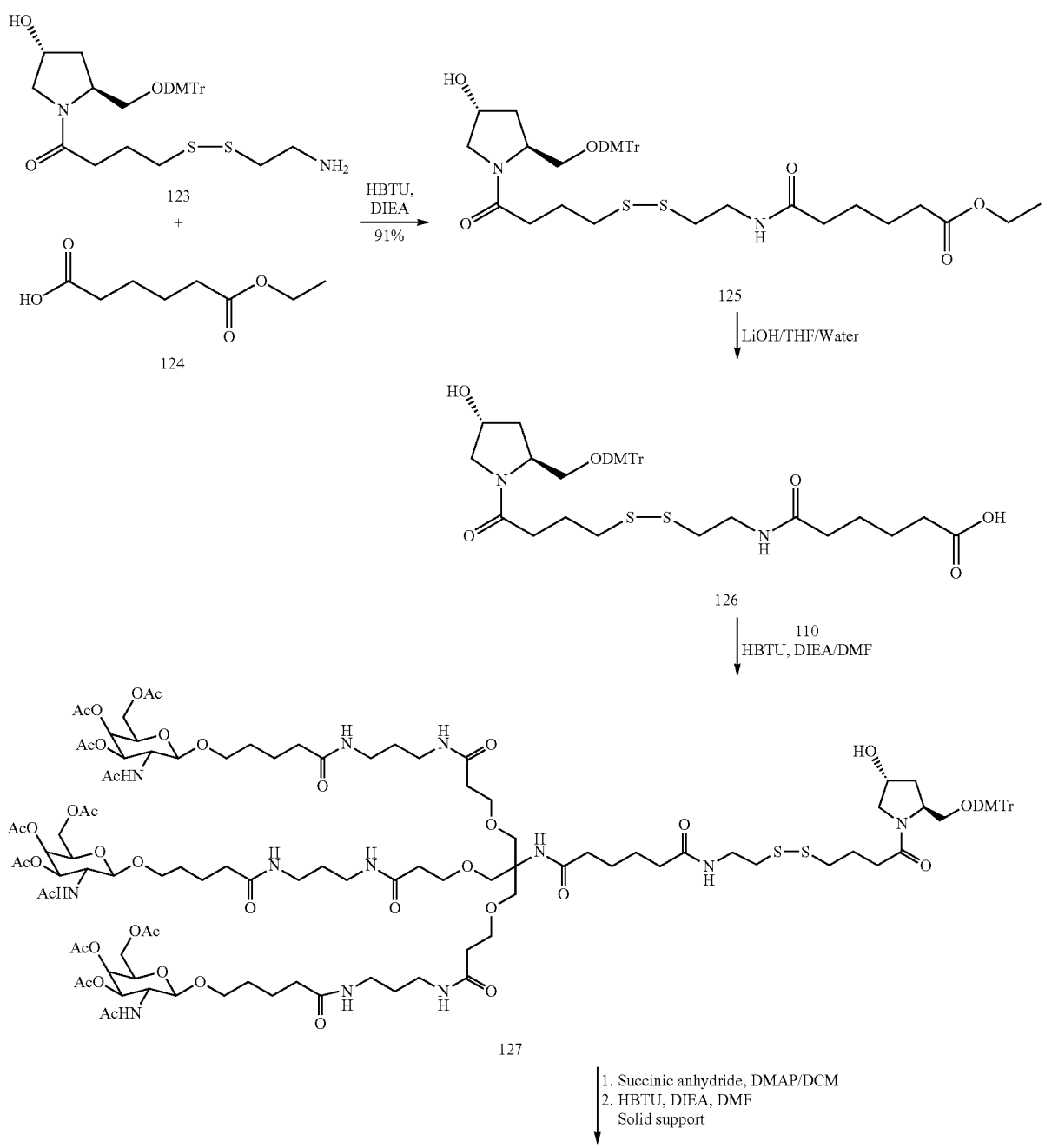

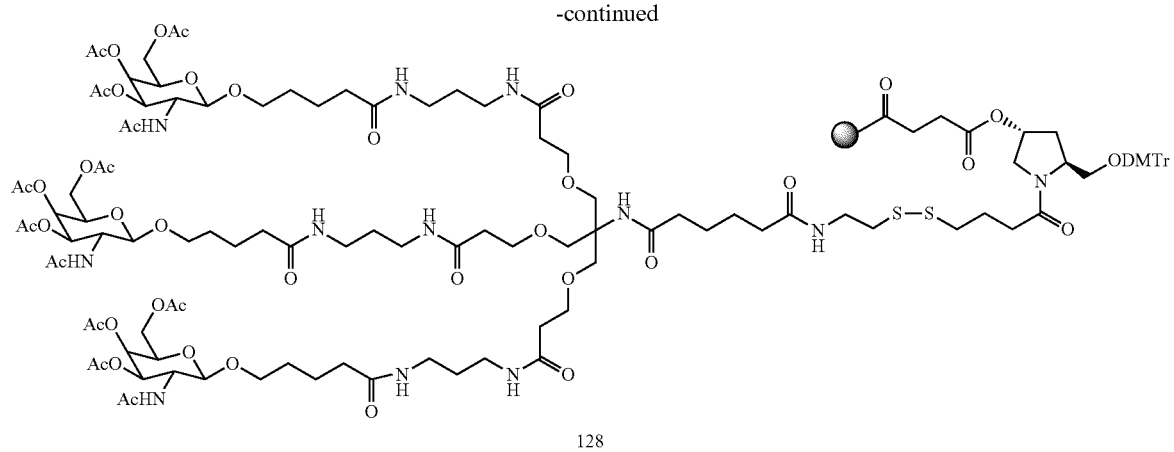

128

Preparation of 125: Amine 123 (2.75 g, 4.61 mmol) and Mono ethyl hexane dioic acid (0.886 g, 5.09 mmol) were dissolved in DMF (50 mL). To that HBTU (2.09 g, 5.51 mmol) and DIEA (2.88 mL, 16.53 mmol) were added and stirred the reaction mixture overnight. Reaction mixture was poured in to an ice water mixture and extracted with DCM, washed with bicarbonate solution and dried over sodium sulfate. Solvent was removed and the residue was purified by chromatography (eluted with 50% EtOAc/Hexane, EtOAc, followed by 5-10% MeOH/DCM) to get the required product as a fluffy white solid (2.25 g, 65%). MS: Calculated for $C_{40}H_{52}N_2O_8S_2$, 752.32. Found 753.31 (M+Na).

Preparation of 126: Compound 125 (2.20 g, 2.97 mmol) was dissolved in a mixture of THF/Water (20 mL, 2:1). LiOH (0.187 g, 4.45 mmol) was added and the mixture stirred 4 hrs. Reaction was monitored TLC, after 4 hrs, cooled and citric acid was added to quench the reaction mixture. Solvent was removed and the residue was extracted DCM, washed with water. Dried over sodium sulfate and removed the solvent. The residue was purified by chromatography (EtOAc, 3-20% MeOH/DCM) to get the required product 126 (0.750 g, 35%) as its TEA salt. MS: Calculated for $C_{38}H_{48}N_2O_8S_2$, 724.29. Found 723.28 (M-H).

Preparation of 127: Compound 126 (1.008 g, 1.390 mmol), 110 (1.904 g, 1.007 mmol) and HBTU (0.400 g, 1.054 mmol) were dissolved in DMF (20 mL). To that DIEA (0.525 mL, 3 eq.) was added and stirred the reaction for 2 days. Reaction mixture was monitored by TLC and MALDI. Solvents were removed and the residue dissolved in DCM, washed with water and bicarbonate solution. DCM layer was dried over sodium sulfate and removed the solvent. It was then purified by chromatography (first ethyl acetate, followed by 3-15% MeOH/DCM) to get the required product as a fluffy off white solid (1.90 g, 76%). MS: Calculated for $C_{117}H_{174}N_{12}O_{43}S_2$, 2499.12. Found 2522.12 (M+Na).

Preparation of Solid Support 128: Compound 127 (2.00 g, 0.800 mmol), succinic anhydride (0.160 g, 2 eq), DMAP (0.300 g, 3 eq.) are taken together in DCM and stir overnight. Solvent is removed and the residue filter through a small pad of silica gel to get the succinate as its TEA salt. Compound 127 (2.00 g, 0.769 mmol) and HBTU (0.290 g, 0.769 mmol) are dissolved in DMF (100 mL). To that DIEA (0.500 mL, 3 mmol) is added and swirl the reaction for 3-4 minutes. Polystyrene support (10.00 g) is added to that and shaken the mixture for 24 hrs. Filter through a frit and washed with DCM, 10% MeOH/DCM, DCM and ether, it is capped with acetic anhydride to get the solid support 128.

Example 5

Synthesis of Carbohydrate Conjugate 136

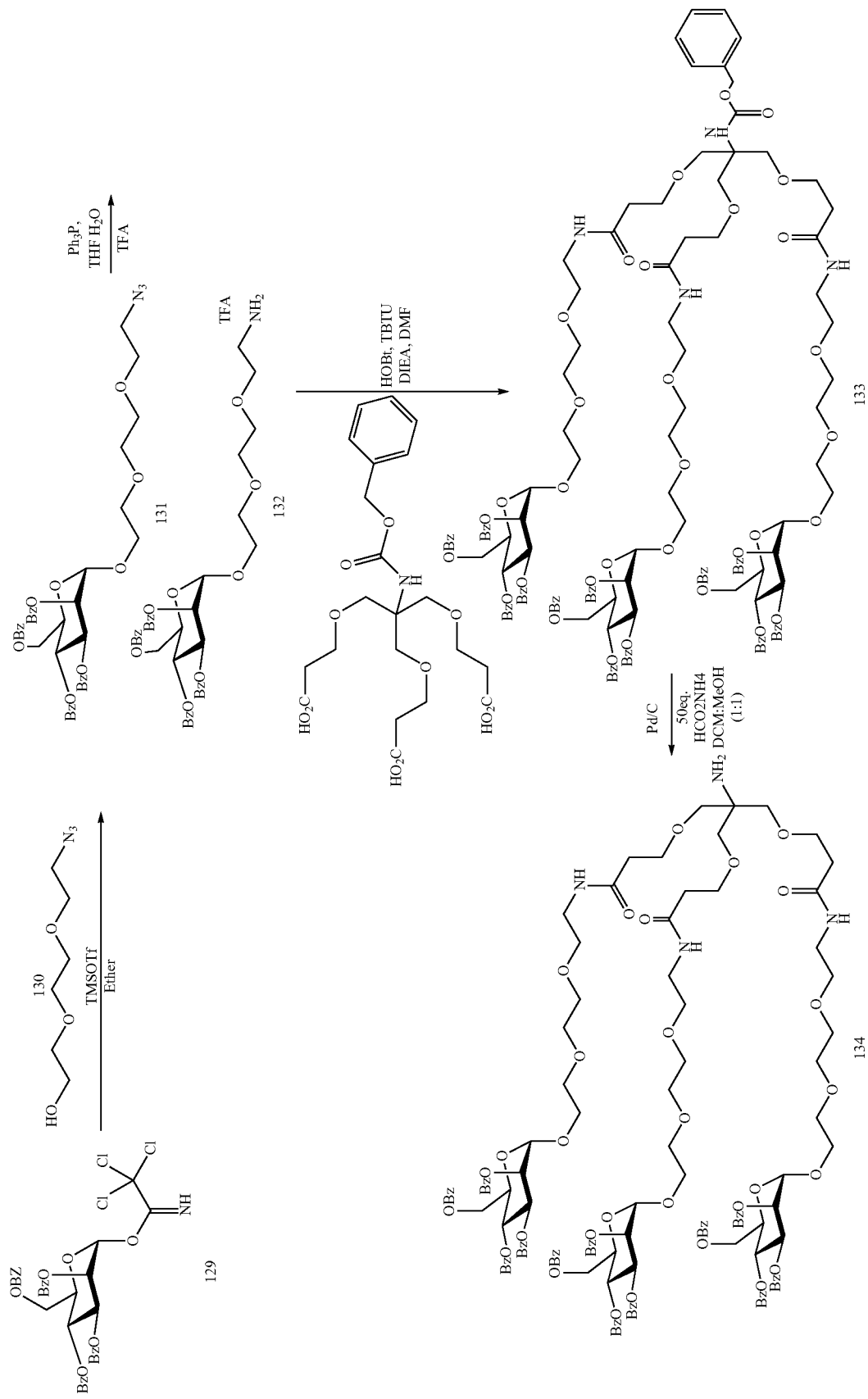

Preparation of 131: Mannose trichloroacetimidate 129 (15.00 g, 20.24 mmol) and azido alcohol (4.25 g, 1.2 eq) were dissolved in Toluene and aziotroped two times. The residue dried under high vacuum overnight. Anhy. diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (20-50% EtOAc/Hexane) to get compound as colorless liquid (8.36 g, 55%). MS: Calculated for $C_{40}H_{39}N_3O_{12}$, 753.25. Found 776.23 ((M+Na)

Preparation of 132: Compound 131 (8.30 g, 11.01 mmol) was dissolved in anhy. THF (70 mL), to that PPh3 (3.46 g, 1.2 eq) was added and the mixture stirred for two days at ambient temperature. Water (1 mL) was added to that and stirred the mixture for another 24 hrs. Reaction was monitored by TLC. Trifluoro acetic acid (1.06 mL, 1.25 eq) and toluene (50 mL) was added to that. Solvents were removed under reduced pressure and residue was co-evaporated toluene two times and dried under high vacuum. This used as such for the next reaction without further purification. MS: Calculated for $C_{40}H_{41}NO_{12}$, 727.26. Found 750.23 (M+Na).

Preparation of 133: Tricarboxylic acid (11.05 g, 23.45 mmol), and amine (68.19 g, 94 mmol, crude from previous reaction) was dissolved in DMF (200 mL). To that TBTU (27.09 g, 84 mmol), HOBt (11.34 g, 84 mmol) and DIEA (28 mL, 160 mmol) was added and stirred the reaction mixture for 24 h. After stirring 24 hrs an additional amount of DIEA (28 mL) was added continued stirring. After 48 hrs solvents were removed under reduced pressure, the residue was dissolved in dichloromethane, washed with 1M phosphoric acid solution, sodium bicarbonate solution, and water and dried over sodium sulfate. Solvents were removed and the residue was purified by chromatography (ethyl acetate, followed by 3-15% MeOH/DCM) to get the required compound 133 as a white solid (41.95 g, 67%) MS: Calculated for $C_{141}H_{146}N_4O_{44}$, 2598.93. Found 2621.89 (M+Na).

Preparation of 134: Compound 133 (3.05 g, 1.176 mmol) was dissolved in a mixture of DCM/MeOH. To that 50 eq. of ammoniumformate was added followed by 5% Pd/C (1.5 g, 50 wt %) and stirred for 8 hrs at ambient temperature. It was filtered through small pad of celite, washed with MeOH/DCM, solvent was removed and residue dried under high vacuum over night to the compound as a white solid (2.65 g, 92%). MS: Calculated for $C_{133}H_{140}N_4O_{42}$, 2464.89. Found 2487.92 (M+Na).

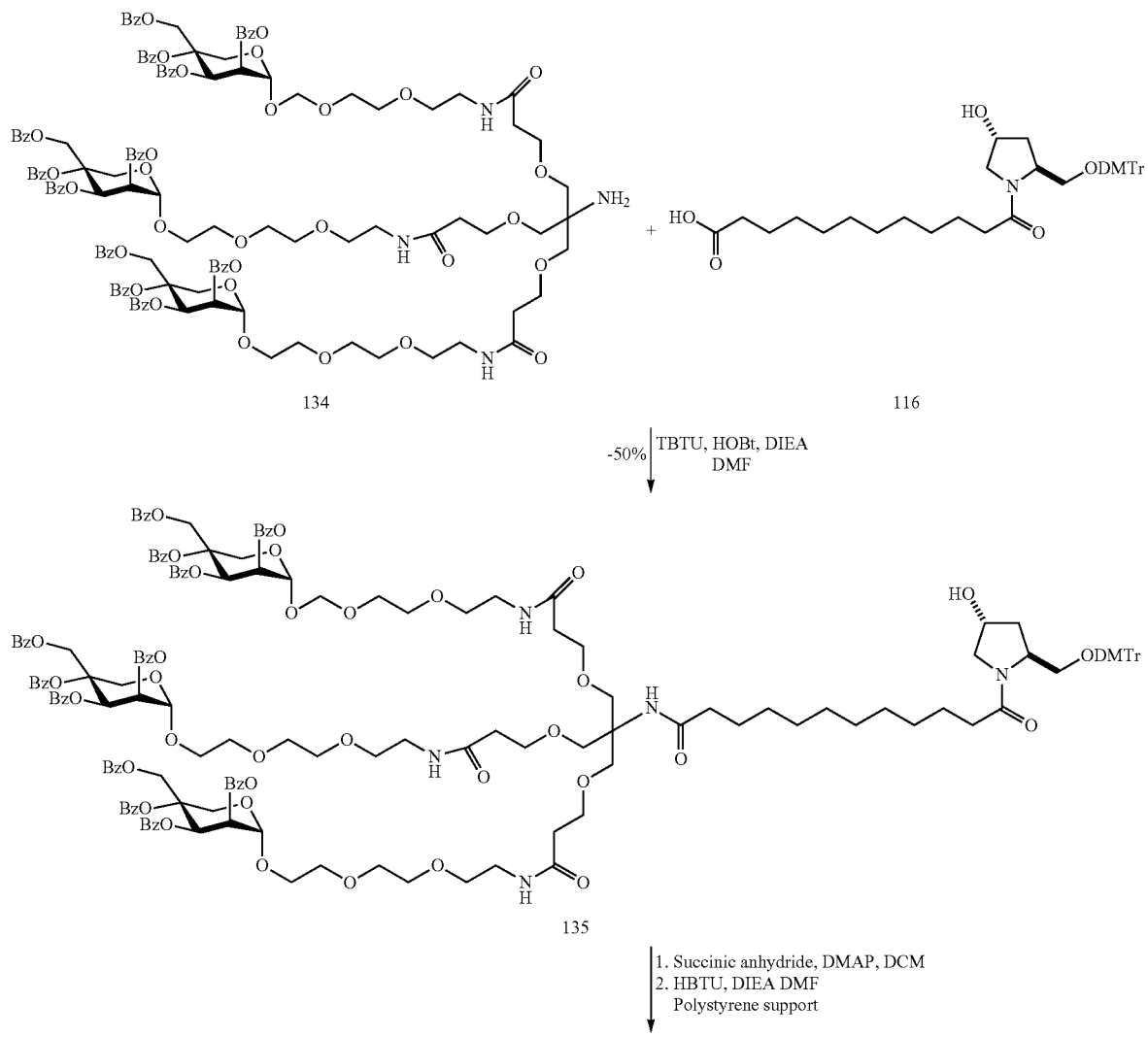

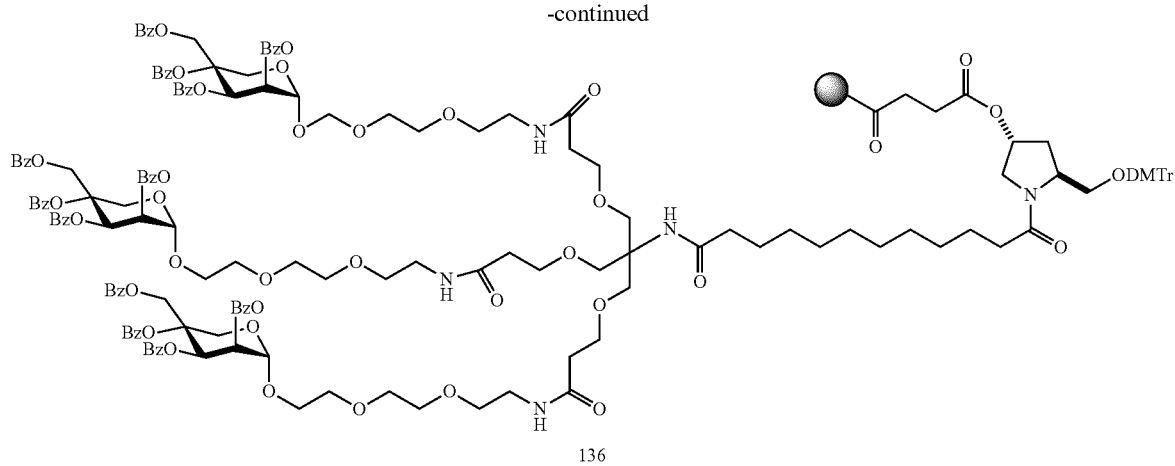

Preparation of 135: Mannose amine (2.076 g, 0.842 mmol), 116 (0.740 g, 1.00 mmol) and TBTU (0.0.353 g, 1.1 eq.) and HOBt (0.149 g, 1.1 eq) were dissolved in DMF (30 mL). To that DIEA (0.0.869 mL, 5 eq.) was added and stirred the reaction for 2 days. Reaction mixture was monitored by TLC and MALDI. Solvents were removed and the residue dissolved in DCM, washed with water and bicarbonate solution. DCM layer was dried over sodium sulfate and removed the solvent. It was then purified by chromatography (first ethyl acetate, followed by 2-4% MeOH/DCM) to get the required product as a fluffy off white solid (1.48 g, 57%). MS: Calculated for $C_{71}H_{187}N_5O_{48}$, 3078.23. Found 3101.25 (M+Na).

Preparation of Solid Support 136: Compound 117 (2.10 g, 0.681 mmol), succinic anhydride (0.136 g, 2 eq) and DMAP (0.249 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid (1.56 g) as its TEA salt. MS: Calculated for $C_{175}H_{191}N_5O_{51}$, 3178.25. Found 3201.20 (M+Na). Succinate (1.00 g, 0.305 mmol) and HBTU (0.138 g, 1.2 eq.) were dissolved in DMF (100 mL). To that DIEA (0.50 mL, excess) was added and swirl the reaction for 3-4 minutes. Polystyrene support (6.05 g) was added to that and shaken the mixture for 24 hrs. Filtered through a frit and washed with DCM, 10% MeOH/DCM, DCM and ether. Solid support dried under vacuum for 2 hrs. It was capped with 25% Ac$_2$O/Py mixture for 2 hr. The same washing and drying procedure repeated to the solid support 136 (6.70 g, 42 mol/g loading).

Example 6

Synthesis of Carbohydrate Conjugate 143

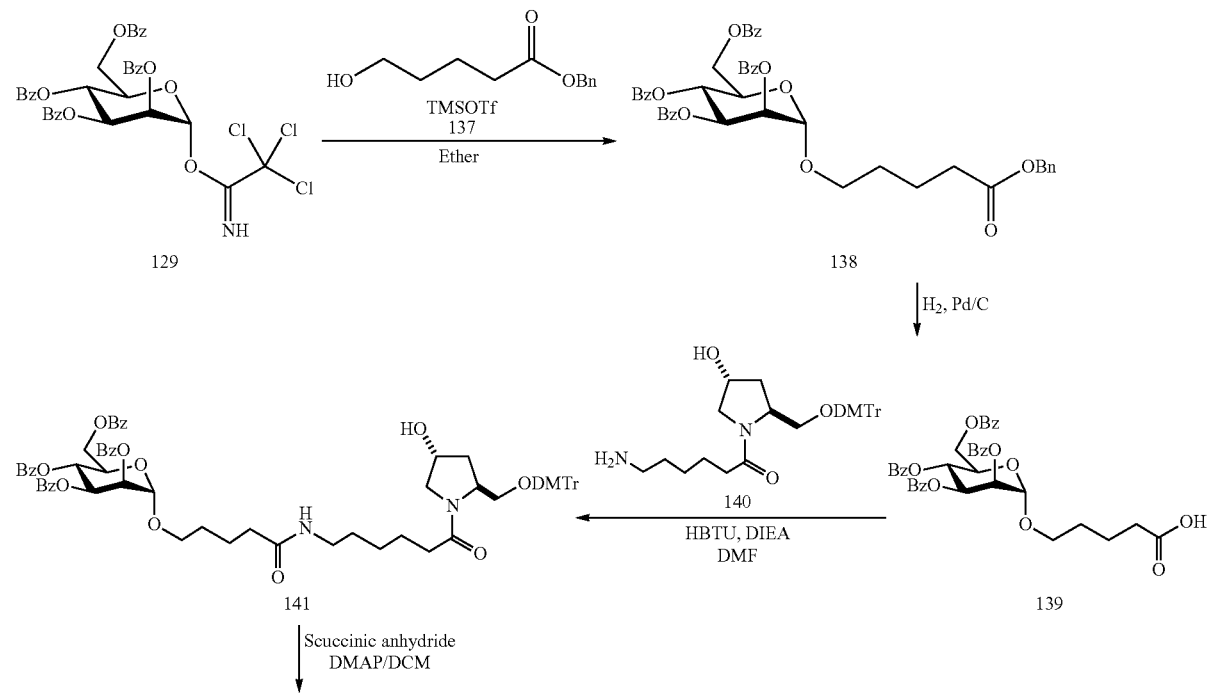

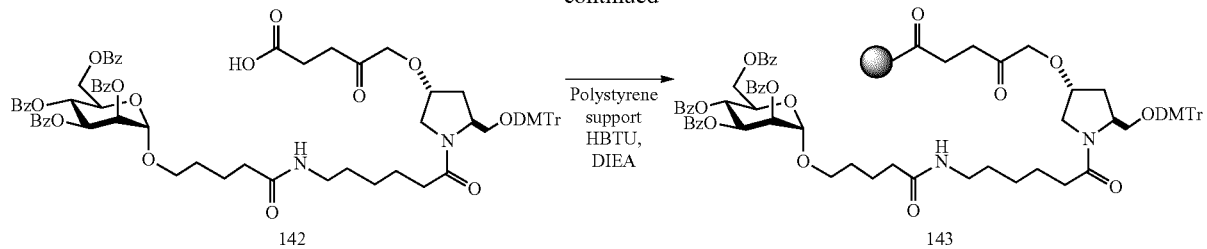

Preparation of 138: Mannose trichloroacetimidate 129 (15.23 g, 20.55 mmol) and 137 (4.36 g, 1.02 eq.) were dissolved in Toluene and aziotroped two times. The residue dried under high vacuum overnight. Anhy. diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (hexane, 15-25% EtOAc/Hexane) to get compound as colorless liquid (14.52 g, 90%). MS: Calculated for $C_{46}H_{42}O_{12}$, 786.27; Found 809.25 ((M+Na).

Preparation of 139: Mannose benzyl ester (14.30 g, 18.17 mmol) was dissolved in Ethyl acetate (100 mL) to that two drops of acetic acid was added. Degassed, Pd/C (1.50 g, 10 wt % Degussa wet type) was added and hydrogenated under balloon pressure for 24 hrs. Reaction was monitored by TLC and MALDI. It was filtered through a small pad of celite, washed with ethyl acetate. Solvent was removed and the residue dried under high vacuum to get the compound as color less oil (11.20 g, 90%). MS: Calculated for $C_{39}H_{36}O_{12}$, 696.22; Found 719.18 ((M+Na).

Preparation of 141: Hydroxy Proline amine 140 (3.82 g, 7.18 mmol), 141 (5.00 g, 7.18 mmol) and HBTU (2.65 g, 7.18 mmol) were dissolved in DMF (50 mL). To that DIEA (3.65 mL, 5 eq.) was added and stirred the reaction for 3 hrs. Reaction mixture was monitored by TLC. Solvents were removed and the residue dissolved in DCM, washed with water and bicarbonate solution. DCM layer was dried over sodium sulfate and removed the solvent. It was then purified by chromatography (first ethyl acetate, followed by 5-10% MeOH/EtOAc) to get the required product as a white solid (4.08 g, 46%). MS: Calculated for $C_{71}H_{74}N_2O_{16}$, 1210.50. Found 1233.40 (M+Na).

Preparation of Solid Support 143: Compound 141 (2.00 g, 1.652 mmol), succinic anhydride (0.330 g, 2 eq), DMAP (0.604 g, 3 eq.) are taken together in DCM and stir overnight. Solvent is removed and the residues filter through a small pad of silica gel to get the succinate as its TEA salt 142. Succinate (2.00 g, 1.526 mmol) and HBTU (0.578 g, 1.526 mmol) are dissolved in DMF (100 mL). To that DIEA (1.32 mL, 5 eq.) is added and swirl the reaction for 3-4 minutes. Polystyrene support (10.00 g) is added to that and shaken the mixture for 24 hrs. Filter through a frit and washed with DCM, 10% MeOH/DCM, DCM and ether, it is capped with acetic anhydride to get the solid support 143.

Example 7

Synthesis of Carbohydrate Conjugate 152

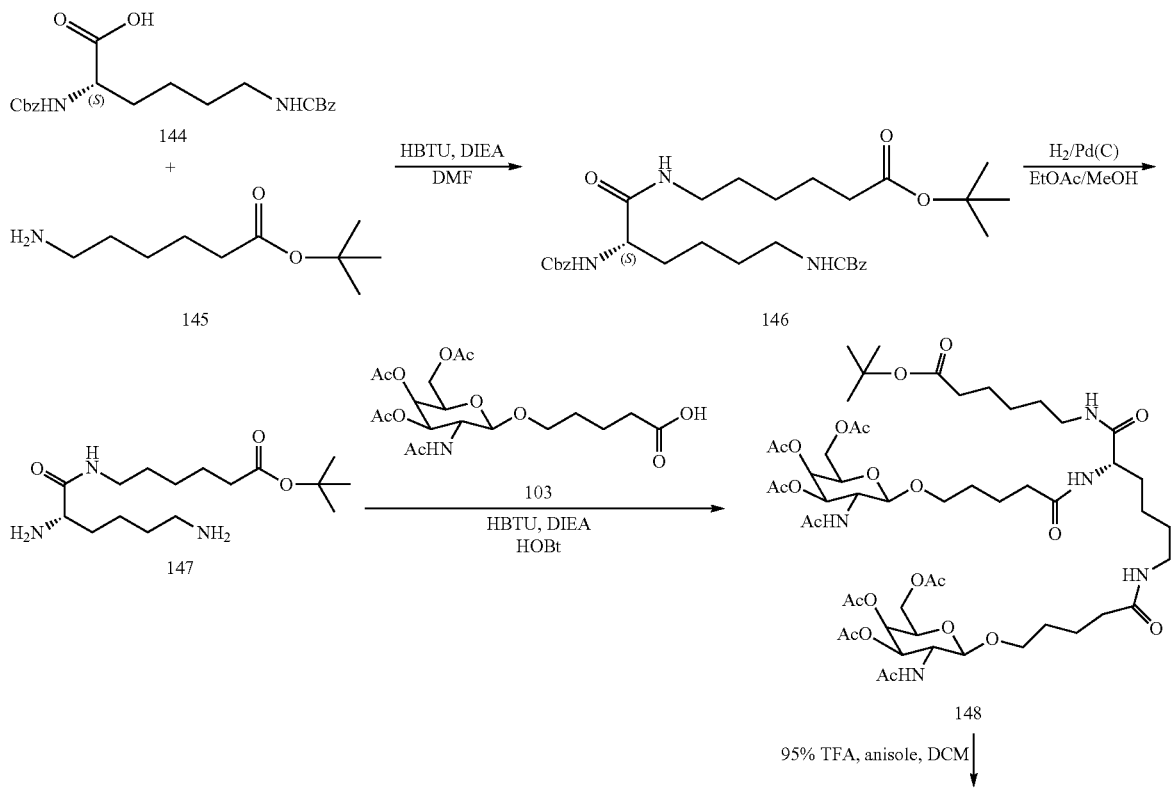

115

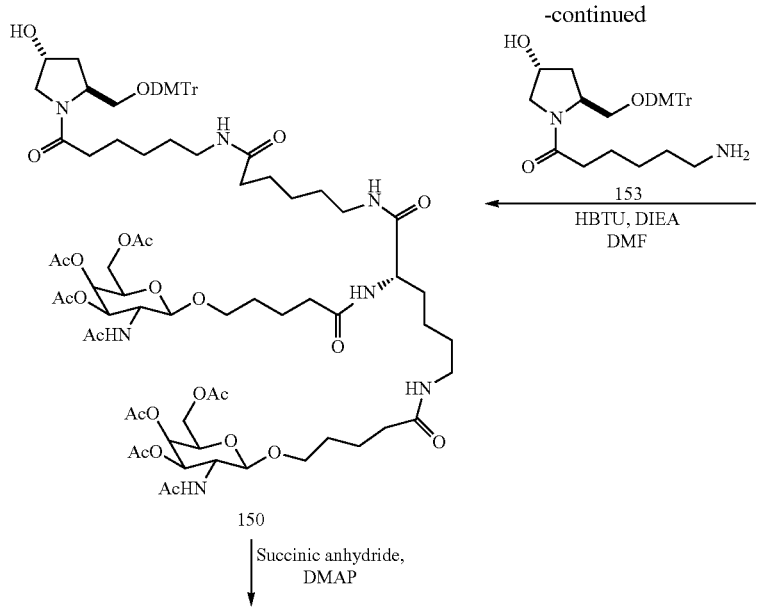

150

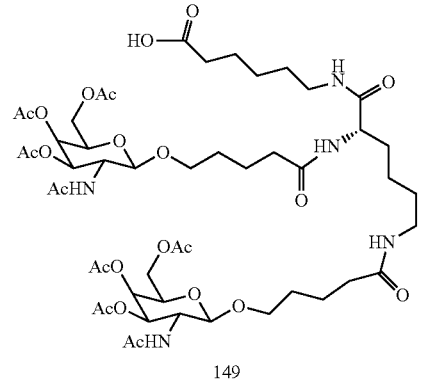

116

149

Succinic anhydride, DMAP ↓

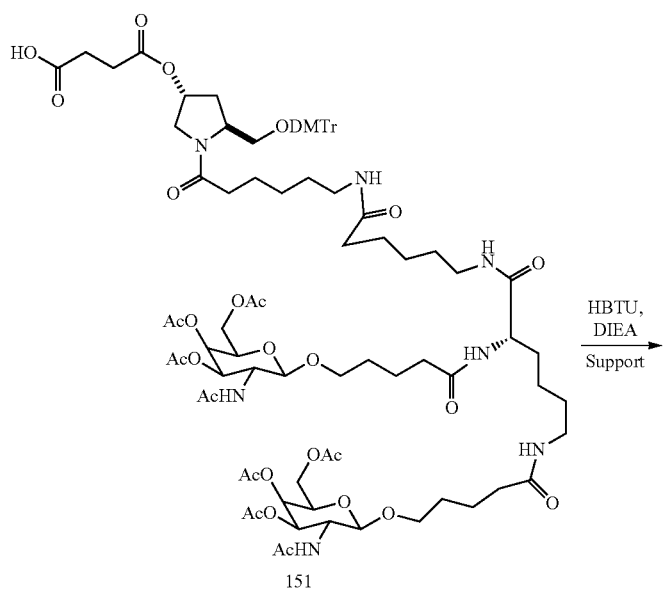

151

HBTU, DIEA Support →

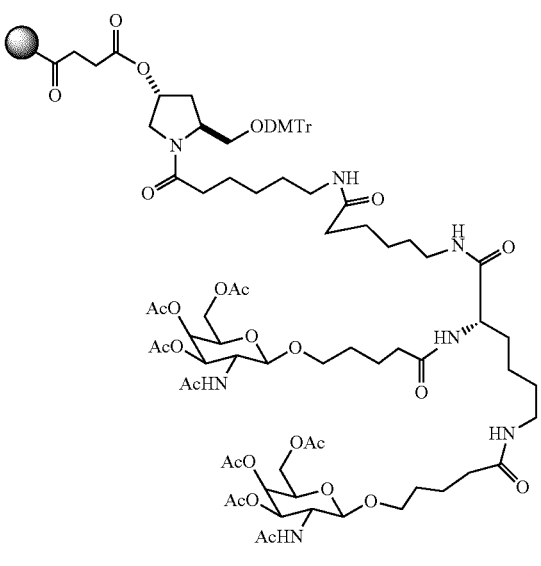

152

Preparation of 146: Compound 144 (26.55 g, 64.06 mmol) and 145 (10.00 g, 53.43 mmol) were dissolved in DMF (150 mL). To that HBTU (24.12 g, 64 mmol) and DIEA (46 mL, 5 eq) were added and stirred the reaction mixture overnight. TLC checked and the mixture was added to ice cold water and extracted with a mixture of ether and ethyl acetate dried over sodium sulfate. Solvents were removed and the crude product was purified by chromatography (20-50% ethylacetate/Hexane) to get the required product as an off white solid (23.20 g, 74%). MS. MW calc. for $C_{32}H_{45}N_3O_7$: 583.72. Found 584.73 (M+H).

Preparation of 147: Compound 146 (3.30 g, 5.65 mmol) was dissolved in a mixture of ethyl acetate/MeOH and hydrogenated under balloon pressure using Pd/C (500 mg) as catalyst overnight. Filtered through a small pad of celite and removed the solvent, this product used for the next reaction without further purification. MS. MW calc. for $C_{16}H_{33}N_3O_3$: 315.25. Found 316.26 (M+H).

Preparation of 148: Compound 147 (5.65 mmol) and GalNAc acid 103 (5.81 g, 12.99 mmol) were dissolved in DMF (80 mL). To that HBTU (4.97 g, 13.10 mmol) and DIEA (7.00 mL, 3 eq) were added and stirred the reaction mixture overnight. Solvents were removed and the residue dissolved in DCM and washed with water and brine, dried over sodium sulfate. Solvents were removed and the crude product was purified by chromatography (EtOAc, followed by 3-10%

MeOH/DCM) to get the required product as an off white solid (5.25 g, 79%). MS. MW calc. for $C_{54}H_{87}N_5O_{23}$: 1173.58. Found 1196.60 (M+Na).

Preparation of 149: Biantineary GalNAc derivative 148 (5.15 g, 4.40 mmol) was dissolved in 15 mL of anhydrous DCM, to that 3 mL of anisole and 30 mL of TFA were added and stirred the reaction mixture for 2 hrs at ambient temperature. TLC checked and toluene was added to the reaction mixture, removed the solvents under reduced pressure. Co-evaporated with toluene two times and the residue dissolved in DCM, washed with water, dried over anhydrous sodium sulfate. Crude product was purified by filtration column (10% MeOH/DCM) to get the required product as pale brown solid (4.40 g, 91%). MS. MW calc. for $C_{50}H_{79}N_5O_{23}$: 1117.52. Found 1140.62 (M+Na).

Preparation of 150: Biantineary GalNAc acid 149 (4.30 g, 3.84 mmol) and hydroxyl proline amine 153 (2.25 g, 1.1 eq) were dissolved in DMF (50 mL). To that HBTU (1.46 g, 3.84 mmol) and DIEA (3.3 mL) were added and stirred the reaction mixture for 3 hrs. Solvents were removed and the residue dissolved in DCM, washed with water and bicarbonate, dried over sodium sulfate. Solvents were removed and the crude product purified by chromatography (3-10% MeOH/DCM) to get the required product as white solid (3.25 g, 52%). MS. MW calc. for $C_{82}H_{117}N_7O_{27}$: 1631.80. Found 1654.45 (M+Na).

Preparation of 151: Compound 150 (3.30 g, 2.02 mmol), succinic anhydride (0.404 g, 2 eq), DMAP (0.740 g, 3 eq.) are taken together in DCM (30 mL) and stir overnight. Solvent is removed and the residues filter through a small pad of silica gel to get the succinate as its TEA salt 151. MS. MW calc. for $C_{86}H_{121}N_7O_{30}$: 1731.82. Found 1753.87 (M+Na).

Preparation of Solid Support 152: Succinate 151 (2.02 mmol) and HBTU (0.842 g, 1.1 eq.) were dissolved in DMF (100 mL). To that DIEA (1.50 mL, excess) was added and swirl the reaction for 3-4 minutes. Polystyrene support (28 g) was added to that and shaken the mixture overnight. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 152 (30.10 g, 30 µmol/g loading).

Example 8

Synthesis of Carbohydrate Conjugate 161

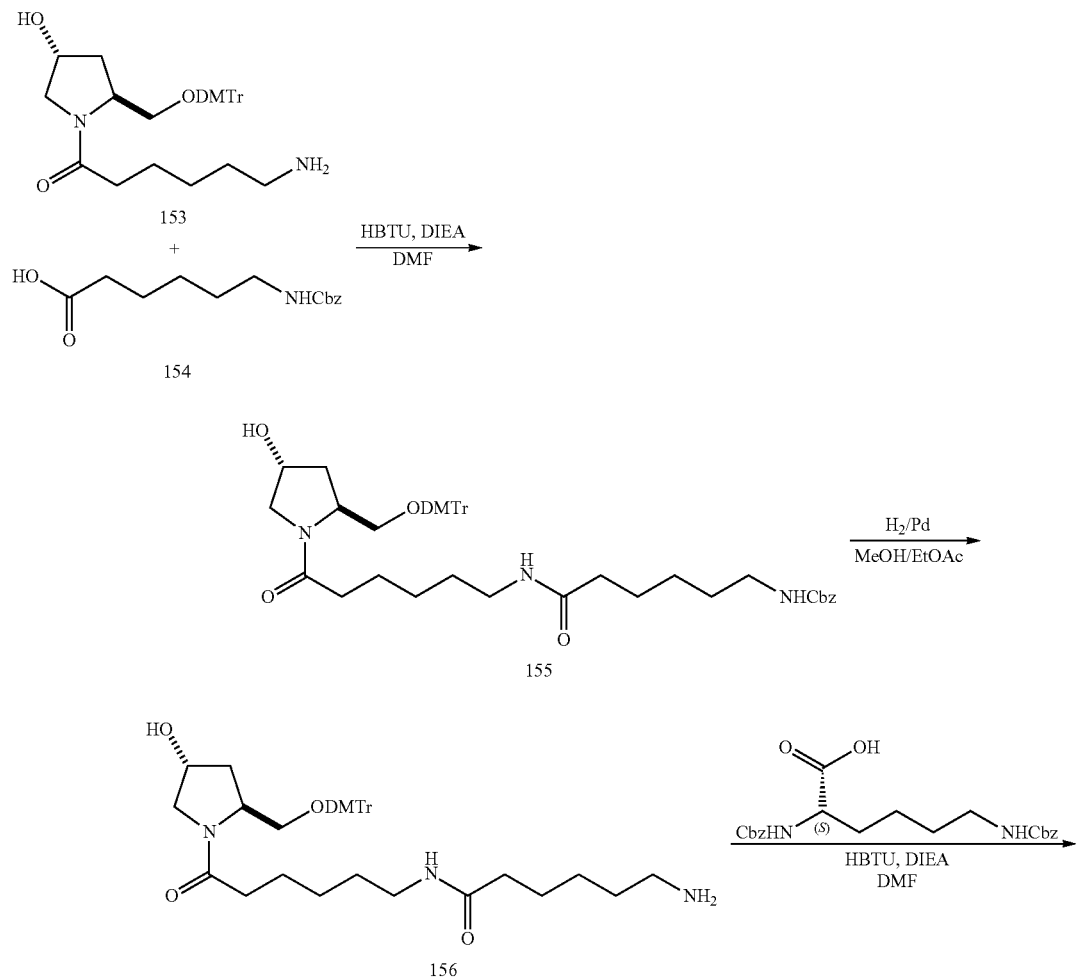

-continued
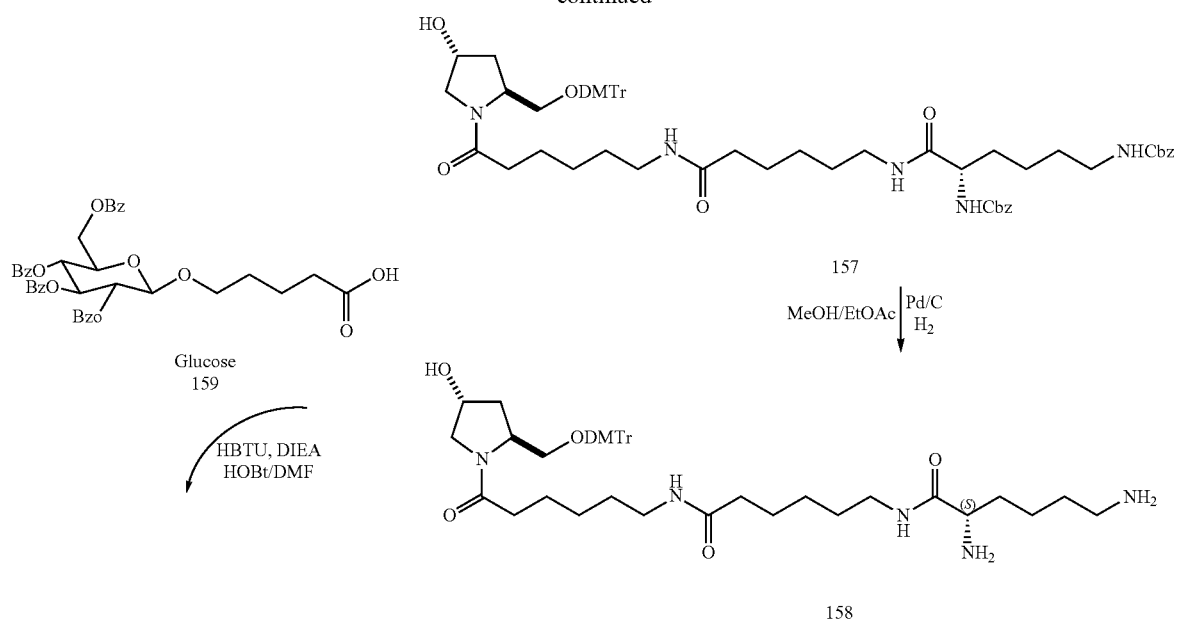
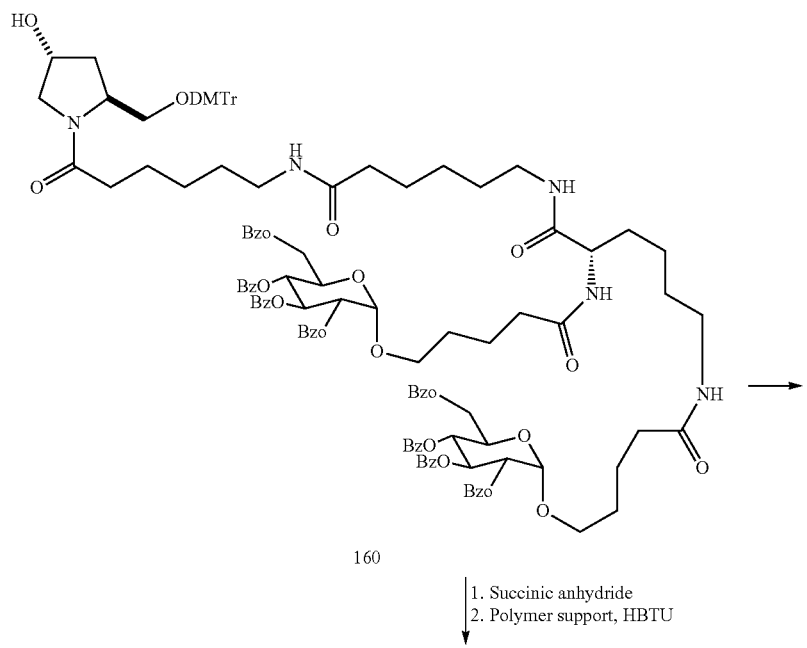

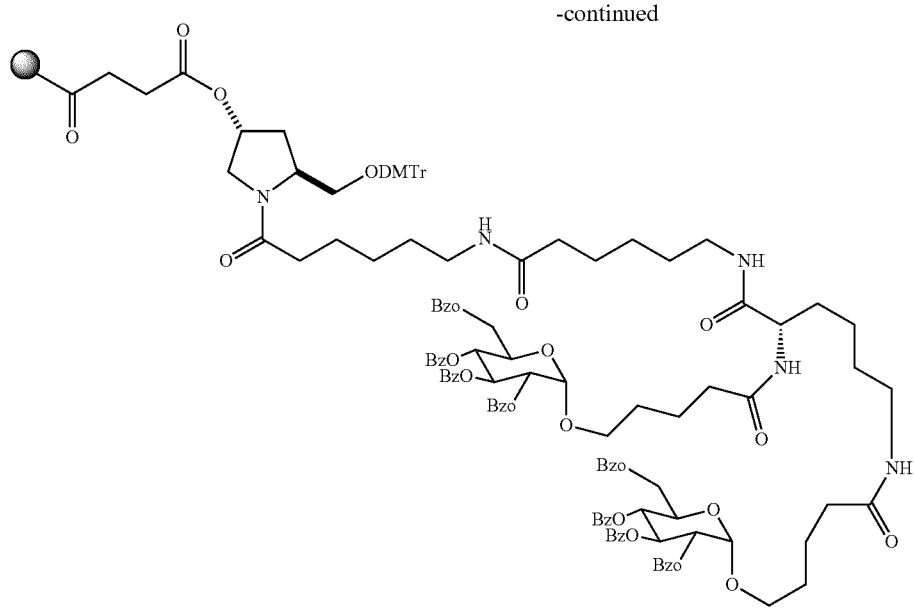

161

Preparation of 155: Hydroxy proline amine 153 (10.00 g, 18.76 mmol) and 154 (4.98 g, 18.76 mmol) were dissolved in DMF (100 mL). To that HBTU (7.83 g, 20.64 mmol) and DIEA (9.81 mL, 56.29 mmol) were added and stirred the reaction for 2 hrs. TLC checked and the mixture was added to ice cold water and extracted with a mixture of ether and ethyl acetate dried over sodium sulfate. Solvents were removed and the crude product was purified by chromatography (0-15% MeOH/DCM) to get the required product as an off white solid (13.20 g, 90%). MS. MW calc. for $C_{46}H_{57}N_3O_8$: 779.41. Found 780.42 (M+H).

Preparation of 156: Compound 155 (13.00 g, 16.66 mmol) was dissolved in a mixture of ethyl acetate/MeOH and hydrogenated under balloon pressure using Pd/C (1.50 g) as catalyst overnight in presence of small amount of triethyl amine. Filtered through a small pad of celite and removed the solvent, this product used for the next reaction without further purification (9.93 g, 92%). MS. MW calc. for $C_{38}H_{51}N_3O_6$: 645.38. Found 646.40 (M+H).

Preparation of 157: Compound 156 (9.90 g, 15.33 mmol) and diCbz lysine (6.36 g, 15.33 mmol) were dissolved in DMF (100 mL). To that HBTU (6.11 g, 15.33 mmol) and DIEA (8 mL, excess) were added and stirred the reaction for 2 hrs. TLC checked and the mixture was added to ice cold water and extracted with a mixture of ether and ethyl acetate dried over sodium sulfate. Solvents were removed and the crude product was purified by chromatography (0-10% MeOH/DCM) to get the required product as an off white solid (13.10 g, 83%). MS. MW calc. for $C_{60}H_{75}N_5O_{11}$: 1041.55. Found 1042.57 (M+H).

Preparation of 158: Compound 157 (12.90 g, 12.37 mmol) was dissolved in a mixture of ethyl acetate/MeOH and hydrogenated under balloon pressure using Pd/C (1.30 g) as catalyst. TLC checked after 3 hrs filtered through a small pad of celite and removed the solvent, this product used for the next reaction without further purification. MS. MW calc. for $C_{44}H_{63}N_5O_7$: 773.47. Found 774.50 (M+H).

Preparation of 160: Compound 158 (2.32 g, 3 mmol) and Glucose acid 159 (4.50 g 6.45 mmol) were dissolved in DMF (60 mL). To that HBTU (2.44 g, 6.45 mmol) and DIEA (3.36 mL, 3 eq) were added and stirred the reaction for 2 hrs and poured the reaction mixture to ice cold water and extracted with EtOAc/DCM, dried over sodium sulfate. Solvents were removed and the crude product was purified by chromatography (EtOAc, followed by 0-10% MeOH/DCM) to get the required product as an off white solid (5.40 g, 85%). MS. MW calc. for $C_{122}H_{31}N_5O_{29}$: 2129.89. Found 2152.90 (M+Na).

Preparation of Solid Support 161: Compound 160 (5.20 g, 2.44 mmol), succinic anhydride (0.488 g, 2 eq) and DMAP (0.894 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid as its TEA salt. MS: MW calc. for $C_{126}H_{135}N_5O_{32}$: 2229.91. Found 2252.50 (M+Na). Succinate (2.44 mmol) and HBTU (0.925 g, 1.2 eq.) were dissolved in DMF (200 mL). To that DIEA (1.27 mL, excess) was added and swirl the reaction for 3-4 minutes. Polystyrene support (24 g) was added to that and shaken the mixture for 24 hrs. Filtered through a frit and washed with DCM, 10% MeOH/DCM, DCM and ether. Solid support dried under vacuum for 2 hrs. It was capped with 25% Ac₂O/Py mixture for ½ hr. The same washing and drying procedure repeated to the solid support 161 (27 g, 31 umol/g loading).

Example 9
Synthesis of Carbohydrate Conjugate 165 and 166
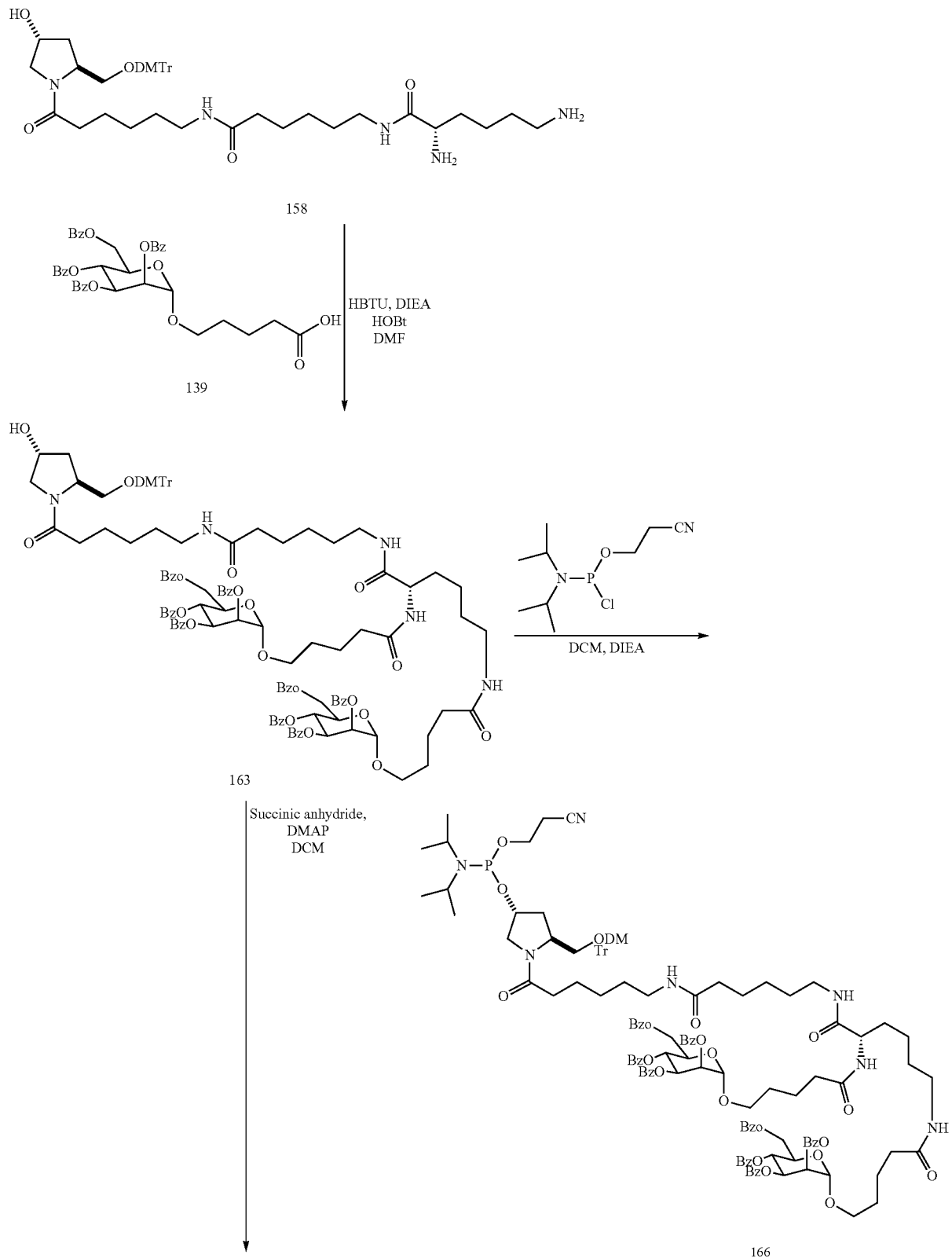

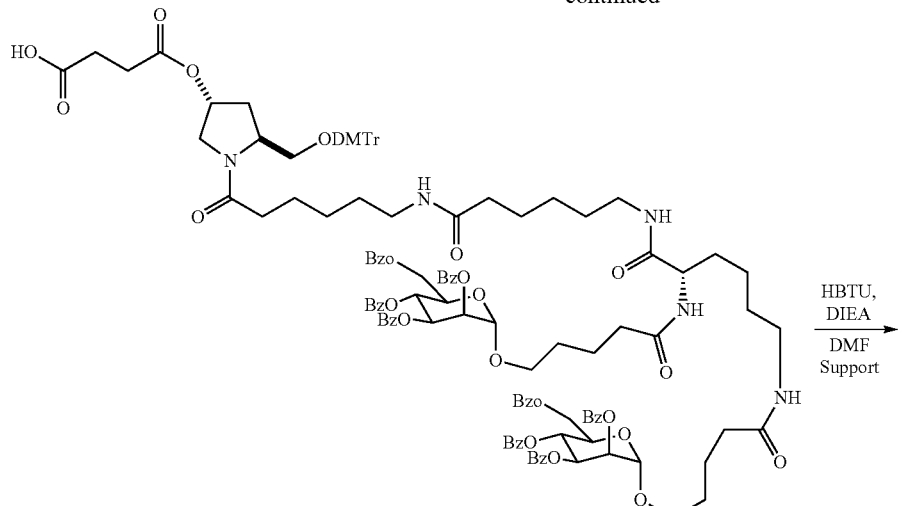

164

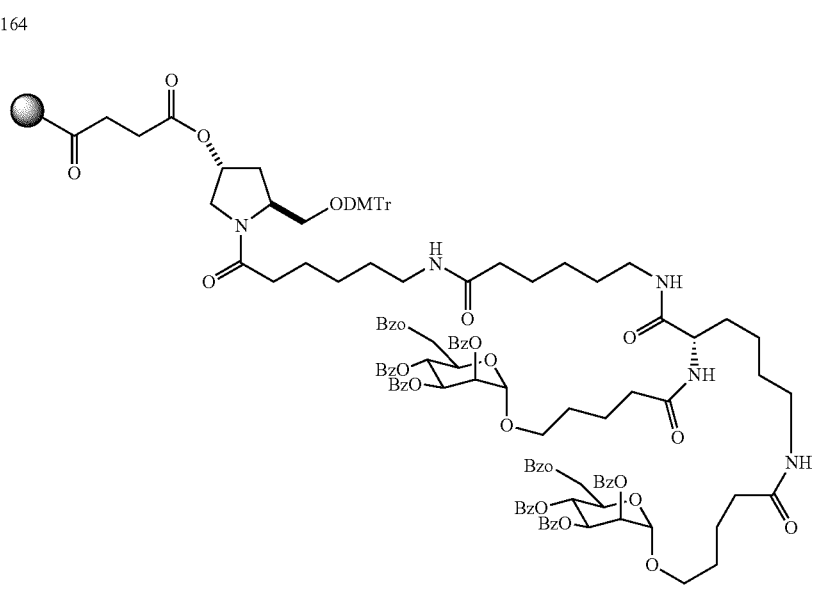

165

Preparation of 163: Compound 158 (5.40 g, 6.97 mmol) and mannose acid 139 (9.96 g 14.30 mmol) were dissolved in DMF (100 mL). To that HBTU (5.42 g, 14.30 mmol) and DIEA (7.45 mL, excess) were added and stirred the reaction for 2 hrs and poured the reaction mixture to ice cold water and extracted with EtOAc/DCM, dried over sodium sulfate. Solvents were removed and the crude product was purified by chromatography (EtOAc, followed by 2-10% MeOH/DCM) to get the required product as an off white solid (9.20 g, 62%). MS. MW calc. for $C_{122}H_{131}N_5O_{29}$: 2129.89, Found 2152.65 (M+Na).

Preparation of Solid Support 165: Compound 163 (3.20 g, 1.408 mmol), succinic anhydride (0.2835 g, 2 eq) and DMAP (0.516 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid as its TEA salt. MS: MW calc. for $C_{126}H_{135}N_5O_{32}$: 2229.91. Found 2252.90 (M+Na). Succinate (1.408 mmol) and HBTU (0.640 g, 1.2 eq.) were dissolved in DMF (200 mL). To that DIEA (1.22 mL, excess) was added and swirl the reaction for 3-4 minutes. Polystyrene support (20 g) was added to that and shaken the mixture for 24 hrs. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 161 (23.2 g, 54.7 umol/g loading).

Preparation of 166: Compound 163 (4.01 g, 1.88 mmol) was dissolved in DCM (50 mL) and DIEA (0.65 mL, 3.75 mmol) was added. Amidite reagent (0.629 mL, 2.822 mmol) was added to this mixture and stirred the reaction mixture for 15 minutes. TLC checked and transferred the reaction mixture to a separatory funnel, washed with water and sodium bicarbonate solution. Dried over anhydrous sodium sulfate and removed the solvent. The crude product was purified by chromatography (30-80% Acetone/DCM) to get the product (4.20 g, 96%). $^{31}P$ NMR ($CDCl_3$, 400 MHz) δ=148.19, 147.79, 147.33. MS. MW calc. for $C_{131}H_{148}N_7O_{30}P$: 2330.00. Found 2353.20 (M+Na).

Example 10
Synthesis of Carbohydrate Conjugate Building Blocks
Synthesis of 171, 172, 173 and 174. Building blocks 171 and 172 are synthesized using a procedure similar to that for synthesis of 103. Building blocks 173 and 174 are synthesized using a procedure similar to that for synthesis of 105.
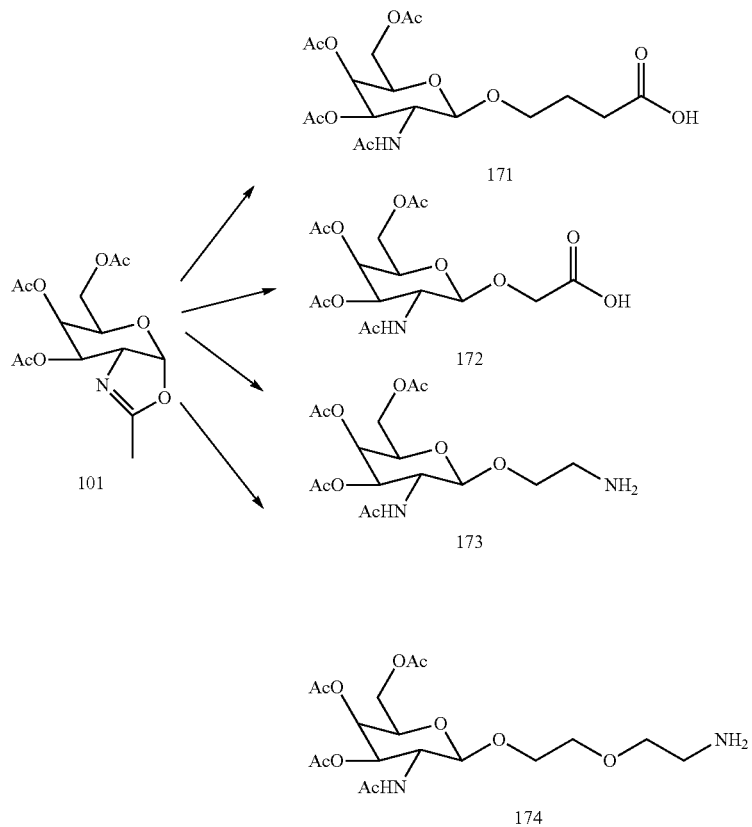
Synthesis of 180. Building block 180 is synthesized using a procedure similar to that for synthesis of 110.
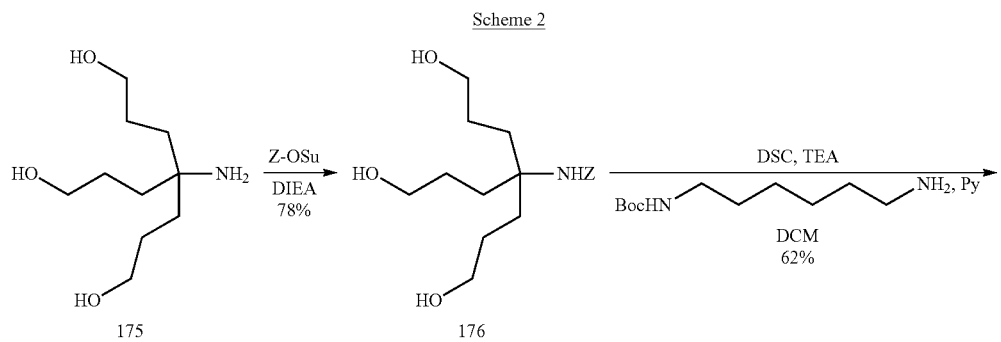

-continued
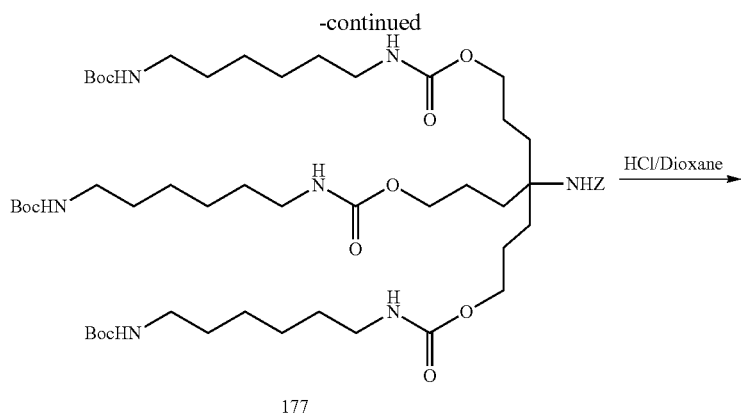
177
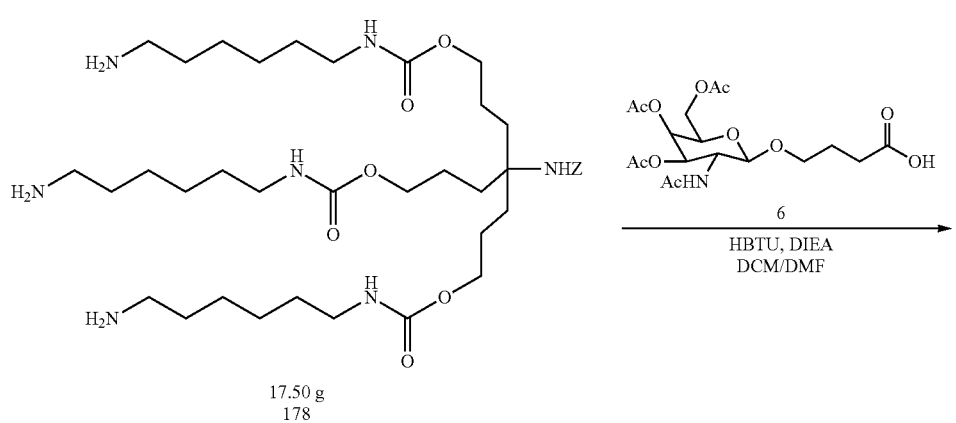
17.50 g
178
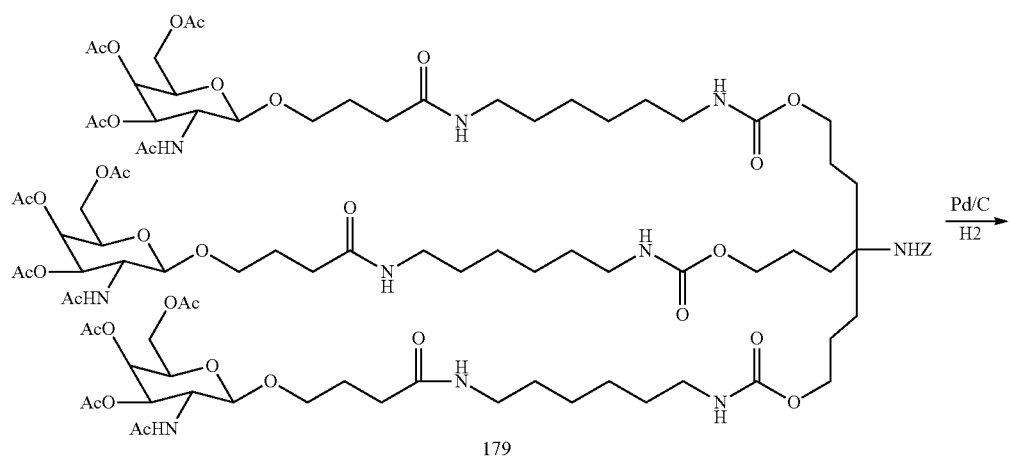
179

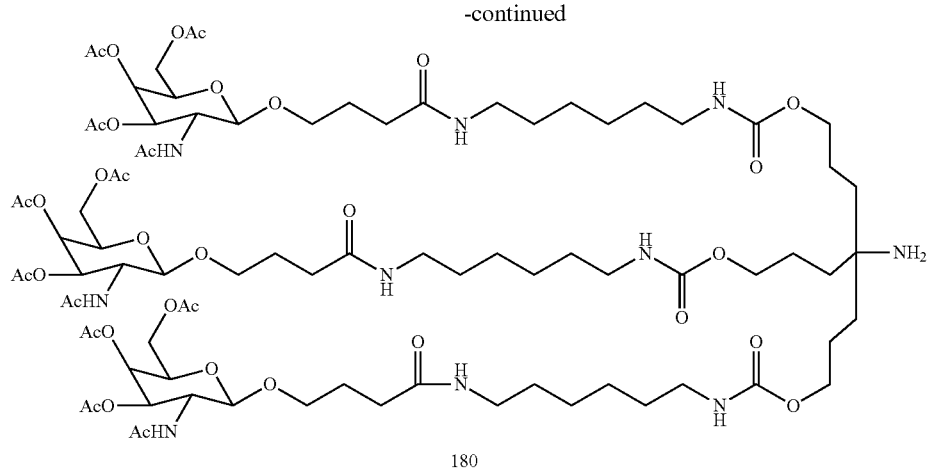
180
Synthesis of Building Block 188.
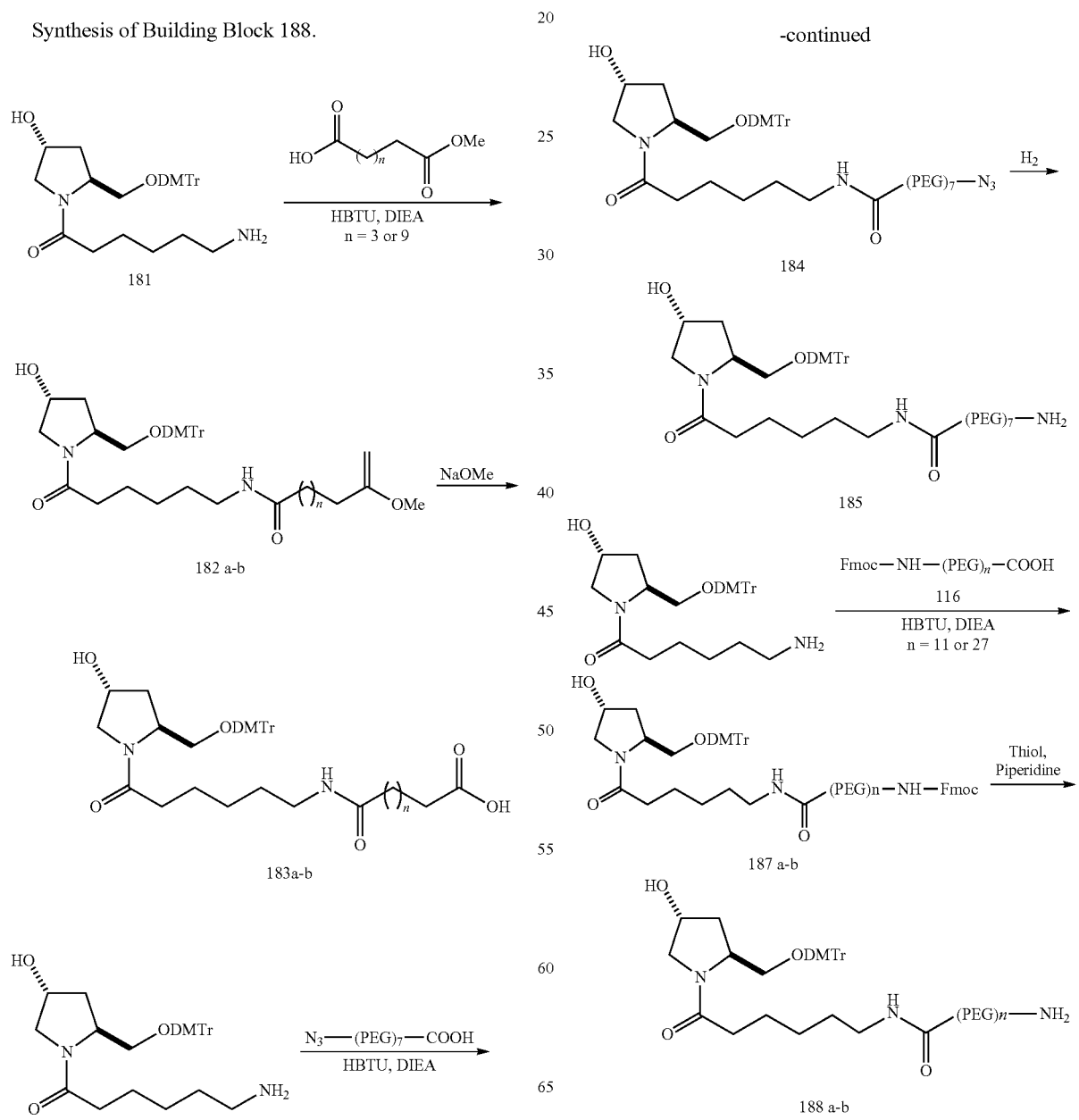

Example 11
Synthesis of Carbohydrate Conjugates
Scheme 4
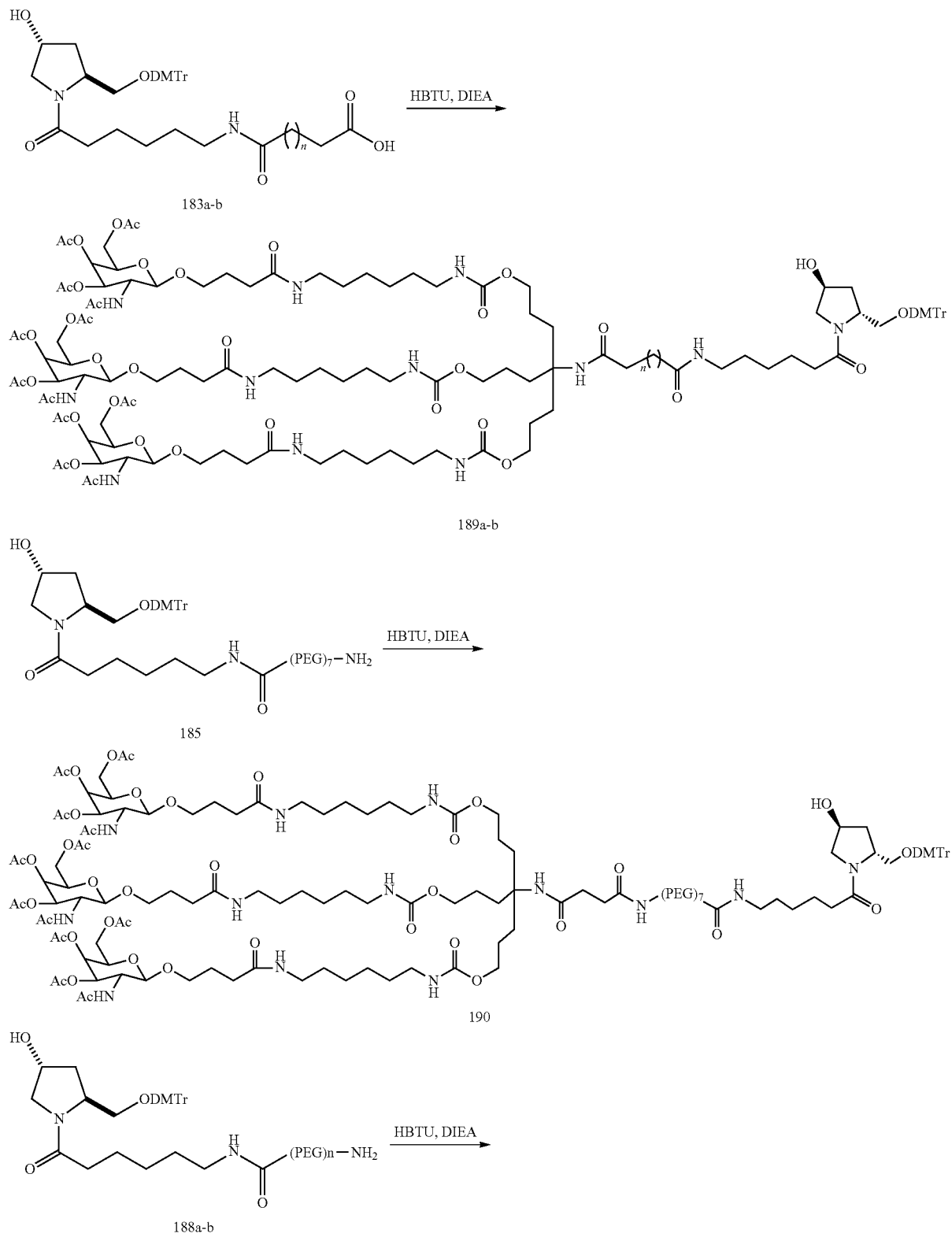

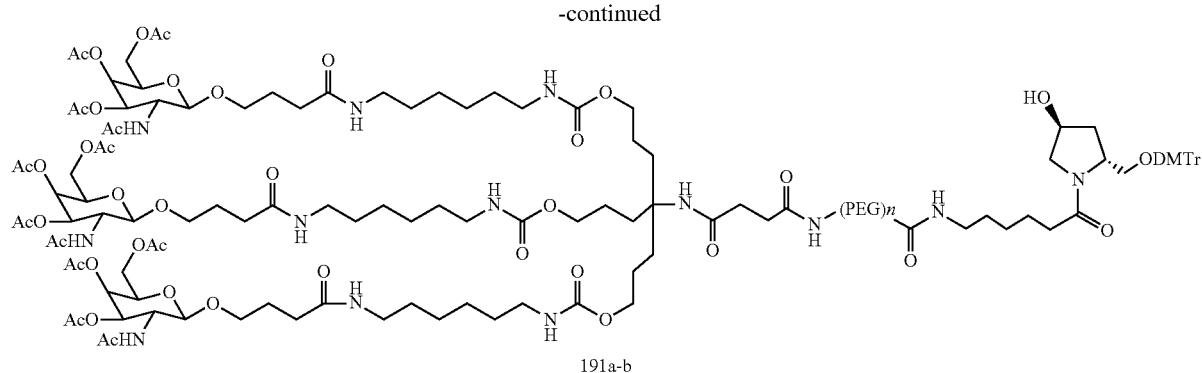
191a-b
The building block 180 is coupled with amines 183, 185 and 188 to provide carbohydrate conjugates 189, 190 and 191 respectively.
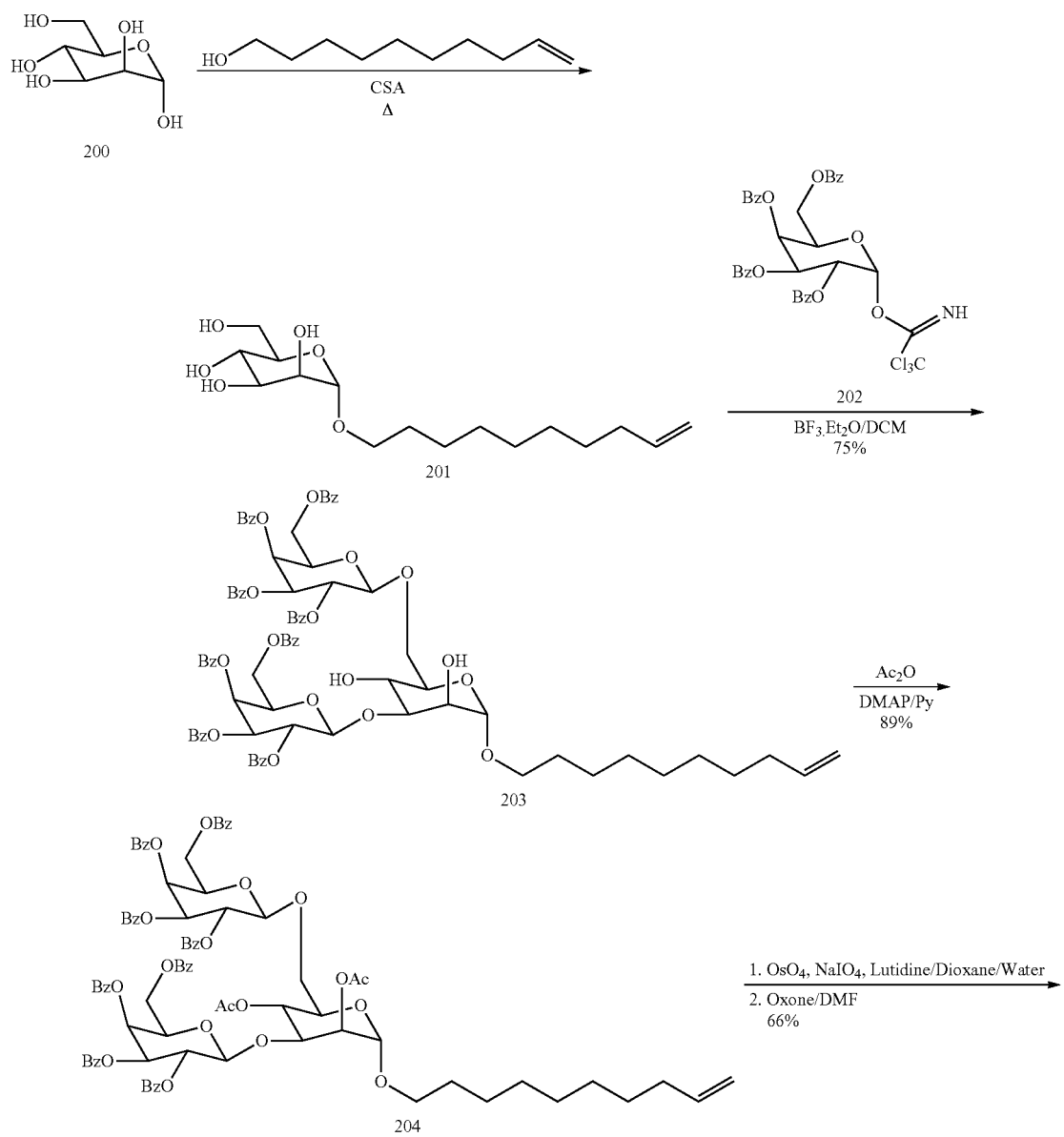

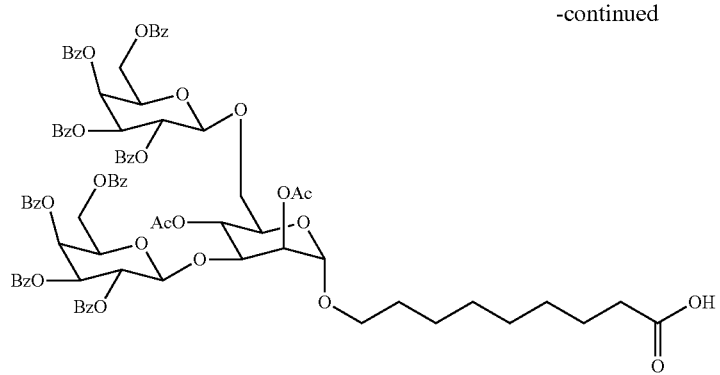

205

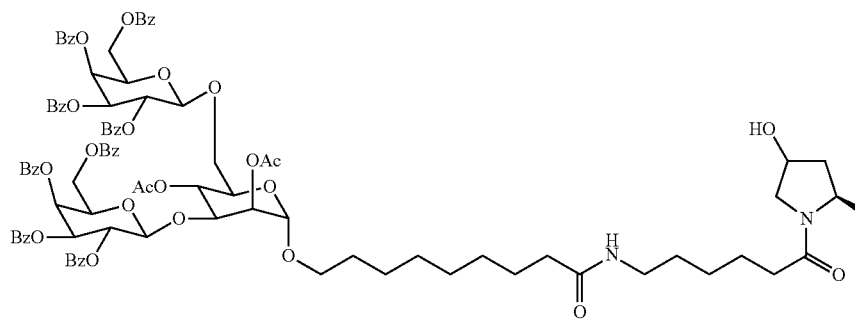

206

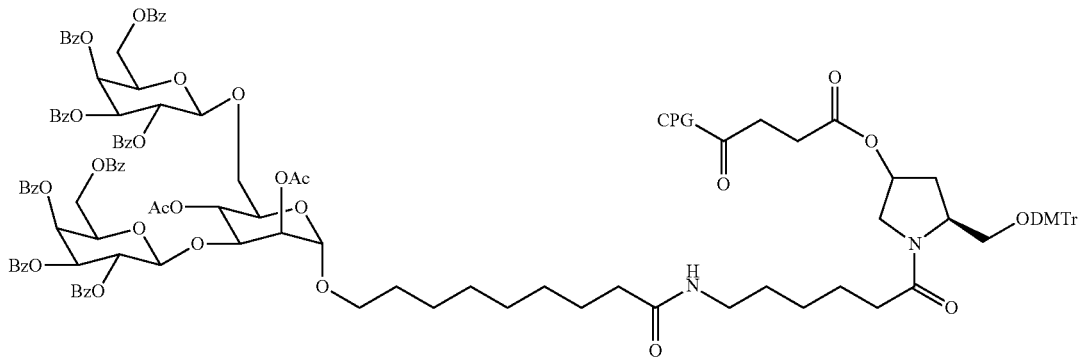

207
(Loading 36 μmol/g)

Preparation of 201: Mannose (10.00 g, 55.53 mmol) and Decinol (100 g, solvent) and CSA (500 mg) were stirred at 110° C. in an oil bath for overnight. The color of the decinol turned to dark brown overnight. Bulk of the decinol was distilled out under reduced pressure. The residue was dissolved in DCM and neutralized with TEA. Extracted the solution with water and dried over sodium sulfate. Solvent was removed and the residue was purified by filtration through a small pad of silica gel, first ethyl acetate followed by 10-15% MeOH/DCM to get the product (7.52 g, 42%). $^1$H NMR (CDCl$_3$, 400 MHz) δ=5.90-5.75(m, 1H), 5.02-4.85(m, 2H), 4.00-3.30(m, 7H), 2.10-1.94(m, 2H), 1.60-1.49(m, 2H), 1.41-1.20(m, 12H).

Preparation of 203: Compound 201 (0.172 g, 0.541 mmol) was dissolved in anhydrous DCM (10 mL) under argon. MS was added to that and cooled the reaction in an ice bath. BF$_3$.Et$_2$O (10 μl) was added to the reaction mixture with stirring. Galactose trichloroacetimidate 202 (1.00 g. 1.35 mmol) in 5 mL of DCM was added drop wise over a period of 15 minutes. Reaction was monitored by TLC, once the acceptor was finished the reaction was quenched with TEA and diluted with DCM, filtered off MS and dried. The residue was purified by chromatography (gradient elution 10-40% EtOAc/Hexane) to the compound as a white fluffy solid (0.550 g, 69%). $^1$H NMR (CDCl$_3$, 400 MHz) δ=7.95-7.20(m, 40 H), 5.90-5.50(m, 7H), 5.35(d, J=8.05 Hz, 1 H), 5.17 (d, J=8.06 Hz, 1H), 4.98-4.81(m, 3H), 4.65-4.09(m, 9H), 3.81-3.42(m, 5H), 3.20(bs, 1H), 2.79(bs, 1H), 2.01-1.88 (m, 2H), 1.30-0.92(m, 12H). $^{13}$C NMR (CDCl$_3$, 100 MHz) δ=166.28, 166.20, 165.88, 165.76, 165.66, 165.64, 165.40, 139.34, 134.04, 133.82, 133.71, 133.66, 133.42, 133.30, 130.21, 129.99, 129.86, 129.70, 129.59, 129.28, 129.03, 129.00, 128.94, 128.77, 128.73, 128.63, 128.61, 128.54, 128.47, 128.44, 114.37, 102.74, 102.68, 98.81, 85.27, 72.43, 71.96, 71.37, 71.31, 71.01, 70.30, 70.26, 70.05, 68.31, 68.23, 67.41, 66.11, 62.63, 62.08, 33.96, 29.65, 29.58, 29.53, 29.58, 29.08, 26.20. MS. Molecular weight calculated for C$_{84}$H$_{82}$O$_{24}$, Cal. 1474.52. Found 1497.60 (M+Na).

Preparation of 204: Compound 203 (0.104 g, 0.07 mmol) was dissolved in a mixture of DCM/Py (10 mL, 1:1). Ac$_2$O (0.5 mL, excess) and DMAP (0.050 g) and stirred the reaction overnight. The reaction was quenched with MeOH, solvents were removed and residue was purified by chromatography (gradient elution 10-30% EtOAc/Hexane) to the compound was white fluffy solid (0.108 g, 99%). $^1$H NMR (CDCl$_3$, 400 MHz) δ=8.10-7.20(m, 40H), 5.99(dd, J=3.1, 7.8 Hz, 2H), 5.88-5.75(m, 2H), 5.70(dd, J=7.82, 10.43 Hz, 1H), 5.65-5.47 (m, 2H), 5.10-4.07(m, 13H), 3.90-3.80(m, 1H), 3.69-3.61 (m, 1H), 3.36-3.28(m, 1H), 2.98-2.81 (m, 1H), 2.08(s, 3H), 2.10-2.01 (m, 4H), 1.35(s, 3H), 1.42-1.20(m, 12H). $^{13}$C NMR (CDCl$_3$, 100 MHz) δ=170.12, 170.08, 166.16, 165.67, 165.64, 165.48, 165.46, 164.78, 139.29, 133.80, 133.70, 133.70, 133.54, 133.44, 133.41, 133.35, 130.13, 130.02, 129.92, 129.69, 129.58, 129.49, 129.40, 129.15, 129.10, 128.88, 128.83, 128.79, 128.73, 128.66, 128.47, 128.40, 114.35, 102.32, 99.58, 96.64, 74.51, 72.11, 71.91, 71.46, 71.21, 69.78, 69.72, 69.51, 69.28, 68.19, 68.03, 67.82, 67.12, 61.97, 61.83, 33.94, 29.63, 29.61, 29.55, 29.49, 29.27, 29.20, 29.05, 26.11, 21.06, 20.02. MS: Molecular weight calculated for C$_{88}$H$_{86}$O$_{26}$, Cal. 1558.54. Found 1581.8 (M+Na).

Preparation of 205: Compound 205 (1.36 g, 0.873 mmol) was dissolved in a mixture of Dioxane: Water (40 mL, 3:1). To the reaction mixture lutidine (0.203 mL, 2 eq), followed by OsO$_4$ solution (1 mL. 0.05M solution in $^t$Butanol) were added. Sodium periodate (0.774 g, 4 eq) was added and stirred for 4 hr's at room temperature. Reaction was monitored by TLC, once the starting material was consumed; the mixture was diluted with water and extracted with DCM (3 times) and dried over sodium sulfate. All the solvents were removed and the residue was directly used next reaction. Residue from the above reaction was dissolved in DMF (20 mL) to that Oxone (0.590 g, 1.05 eq) and stirred at ambient temperature for 3 h. Once the starting material was consumed, 2 mL of 1M HCl was added and diluted with Ethyl acetate. Washed with water, brine and dried over sodium sulfate. Solvents were removed and the residue was purified by chromatography (gradient elution 20-40% EtOAc/hexane) to get the compound as a white solid (1.08 g 79%). $^1$H NMR (DMSO-d$_6$, 400 MHz) δ=11.96(s, 1H), 8.00-7.23(m, 40H), 5.85(d, J=3.41 Hz, 1H), 5.82(d, J=3.17 Hz, 1H), 5.79-5.63 (m, 2H), 5.56(dd, J=8.00, 10.01 Hz, 1H), 5.41 (dd, J=8.00, 10.01 Hz, 1H), 5.25 (d, J=7.8 Hz, 1H), 5.15(d, J=7.8 Hz, 1H), 4.90-4.35(m, 7H), 4.10-3.55 (m, 4H), 3.30-3.20(m, 1H), 2.96-2.87 (m, 1H), 2.18-2.10(m, 2H), 1.96(s, 3H), 2.01-1.95 (m, 1H), 1.51-1.39(m, 2H), 1.27(s, 3H), 1.20-1.01 (m, 12H). $^{13}$C NMR (CDCl$_3$, 100 MHz) δ=178.68, 178.48, 170.26, 170.16, 166.25, 165.78, 165.73, 165.70, 165.54, 165.53, 164.83, 133.85, 133.75, 133.60, 133.49, 130.18, 130.08, 128.85, 129.61, 129.52, 129.44, 129.20, 129.13, 128.91, 128.89, 128.81. 128.78, 128.71, 128.51, 128.45, 102.34, 99.67, 96.65, 74.60, 72.17, 71.94, 71.49, 71.21, 69.82, 69.79, 69.55, 69. 37, 68.22, 68.11, 67.81, 67.20, 64.55, 61.99, 61.85, 60.59, 44.06, 33.96, 30.79, 29.39, 29.31, 29.24, 29.20, 29.17, 29.08, 26.08, 24.85, 24.79, 22.20, 21.24, 21.11, 20.07.

MS: Molecular weight calculated for C$_{87}$H$_{84}$O$_{28}$, Cal. 1576.51. Found 1599.50 (M+Na).

Preparation of 206: Compound 205 (0.850 g, 0.539 mmol), hydroxyl proline amine (0.300 g, 0.563 mmol) and HBTU (0.265 g, 0.698 mmol) were dissolved in DMF under argon. DIEA (0.281 mL, 3 eq.) was added to that and stirred for 3 hrs at ambient temperature. The reaction was monitored by TLC; once the starting material was consumed the mixture was poured in to an ice water mixture; extracted with ethyl acetate. washed with water, brine and dried over sodium sulfate. Solvents was removed and the residue was purified by chromatography (first ethyl acetate followed by a gradient elution 3-10% MeOH/DCM) to get the product as a pale yellow solid (1.09 g, 96%). $^1$H NMR (CDCl$_3$, 400 MHz) δ=8.00-7.10(m, 53H), 6.90-6.80(m, 4H), 5.85 (d, J=3.41 Hz, 1H), 5.82(d, J=3.17 Hz, 1H), 5.79-5.63(m, 2H), 5.56(dd, J=8.00, 10.01 Hz, 1H), 5.41 (dd, J=8.00, 10.01 Hz, 1H), 5.25 (d, J=7.8 Hz, 1H), 5.15 (d, J=7.8 Hz, 1H), 4.97 (d, J=4.15 Hz, 1H), 4.90-4.80(m, 3H), 4.70-4.30(m, 7H), 4.20-4.00(m, 2H), 3.95-3.85 (m, 2H), 3.70(s, 6H), 3.69-3.50 (m, 1H), 3.30-3.20 (m, 2H), 2.96-2.87(m, 1H), 2.18-2.10(m, 2H), 1.96(s, 3H), 2.01-1.95 (m, 1H), 1.51-1.39(m, 2H), 1.27 (s, 3H), 1.20-1.01 (m, 20H). $^{13}$C NMR (CDCl$_3$, 100 MHz) δ=171.87, 170.85, 169.46, 169.04, 165.25, 165.21, 165.09, 164.95, 164.48, 164.53, 162.29, 158.09, 157.97, 145.08, 135.87, 135.73, 134.04, 133.74, 133.56, 129.60, 129.18, 129.06, 128.91, 128.84, 128.81, 128.75, 128.67, 128.63, 128.52, 128.41, 127.77, 127.58, 113.19, 113.09, 102.30, 99.60, 96.60, 85.10, 75.68, 71.48, 70.02, 69.81, 68.99, 68.58, 66.55, 61.86, 6=54.96, 45.74, 38.27, 36.32, 35.76, 35.46, 34.15, 30.74, 28.69, 26.20, 25.34, 26.20, 25.34, 24.15, 20.48, 19.54. MS: Molecular weight calculated for C$_{119}$H$_{122}$N$_2$O$_{32}$, Cal. 2090.80, Found 2013.90 (M+Na).

Preparation of Long Alkyl Chain CPG 207: Hydroxy derivative 206 (0.550 g, 0.263 mmol) was dissolved in DCM (10 mL) to that Succinic anhydride (0.078 g, 3 eq) and DMAP (0.128 g, 4 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under high vacuum to get the succinate. PPh$_3$ (0.90 g, 1.3 eq.), DMAP (0.048 g, 1.5 eq.) and the succinate from the previous step were dissolved in a mixture of acetonitrile and DCM (6 mL). A solution of DTNP (0.086 g, 1.05 eq.) in DCM (1 mL) was added to the above solution. The mixture was slowly shaken for 3-4 minutes. Long chain alkylamine-CPG (lcaa CPG, 1.40 g, 133 µmol/g) was added to the mixture and gently shaken for 2 h. The CPG was filtered, successively washed with DCM, mixture of MeOH/DCM (1:9) and DCM until filtrate remained colorless and dried. The dried CPG was transferred into another flask treated with Ac$_2$O in pyridine (25%) in the presence of TEA (1 mL) for 15 min. under gentle shaking. Finally the CPG was filtered, washed with DCM, DCM: MeOH (9:1), followed by DCM and ether. The CPG 207 was dried under vacuum overnight and the loading was measured as reported (1.48 g, loading 36 µmol/g).

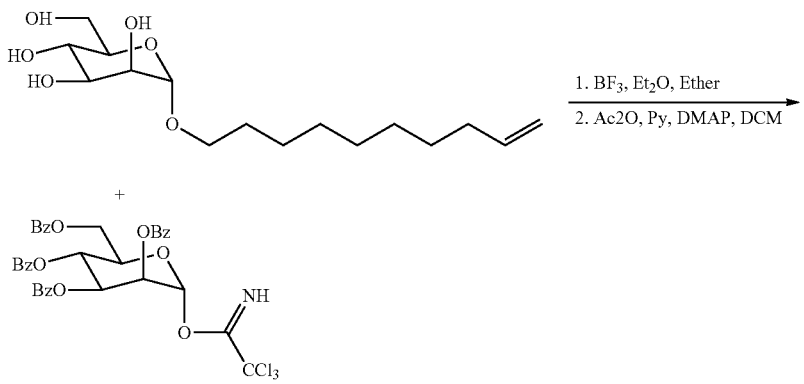

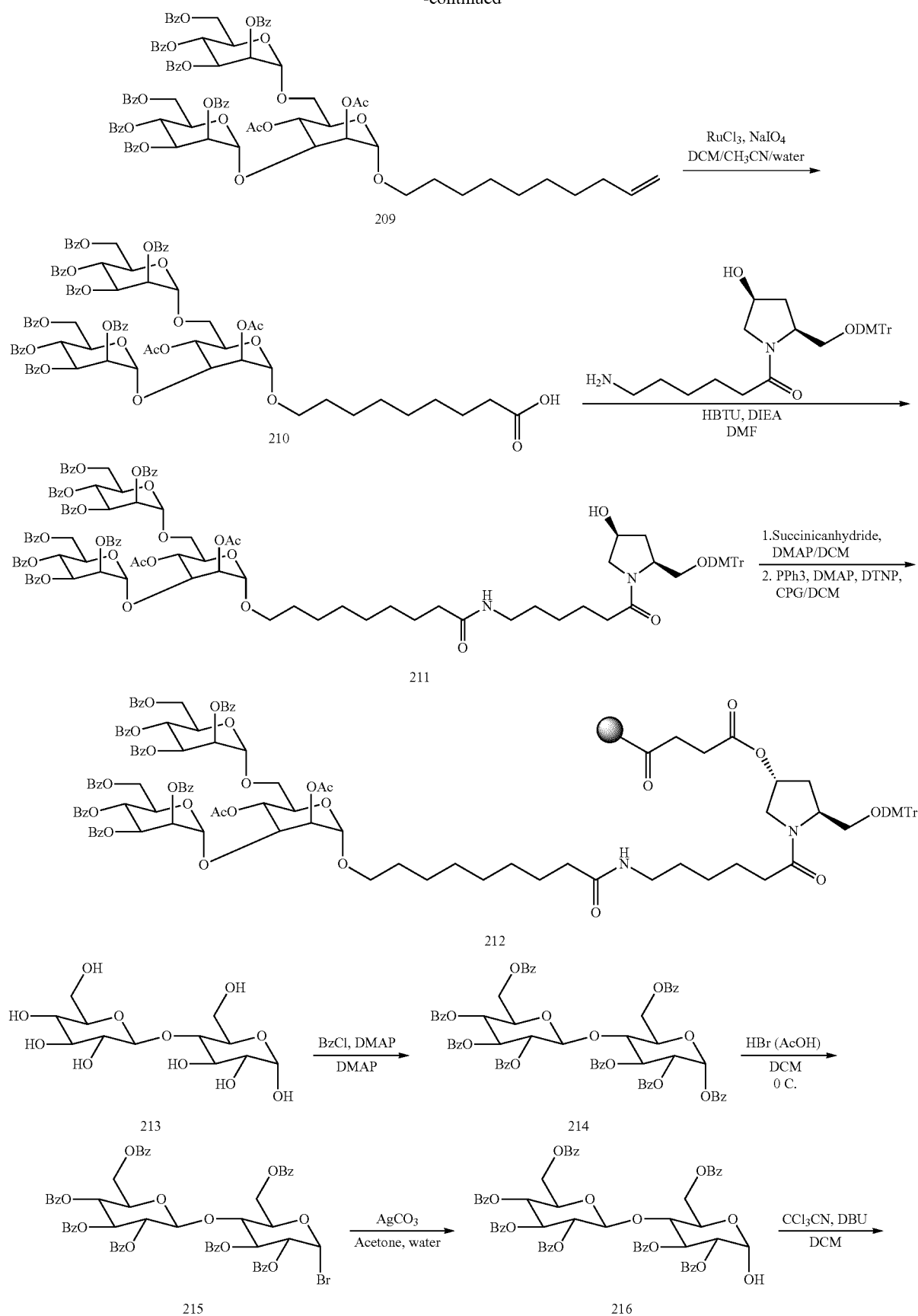

-continued
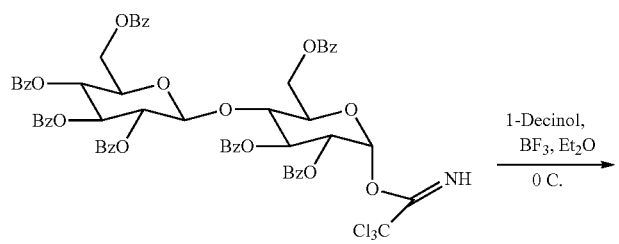
217
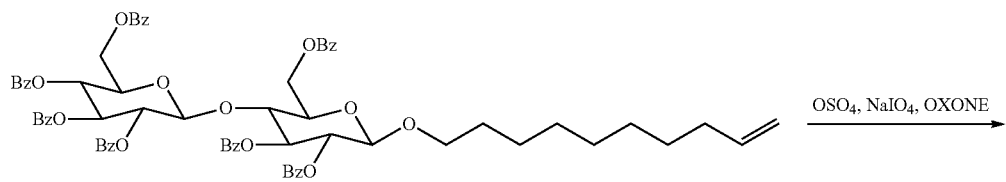
218
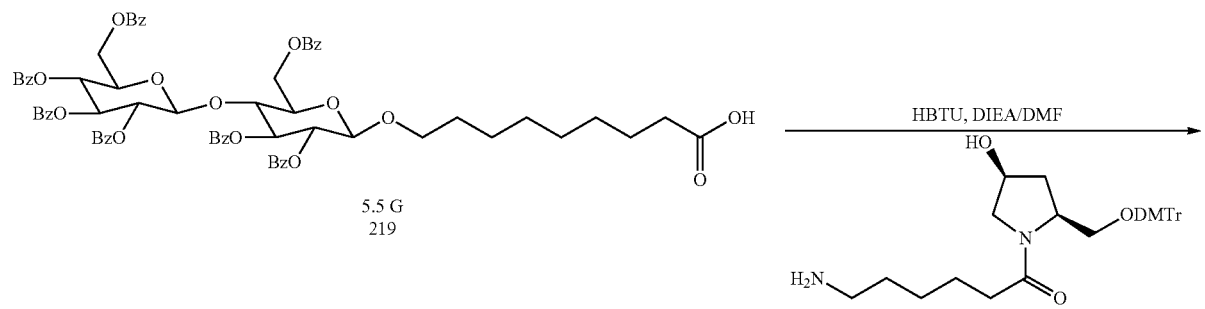
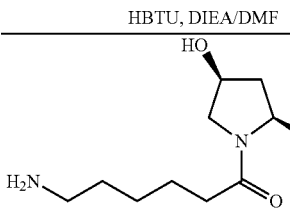
5.5 G
219
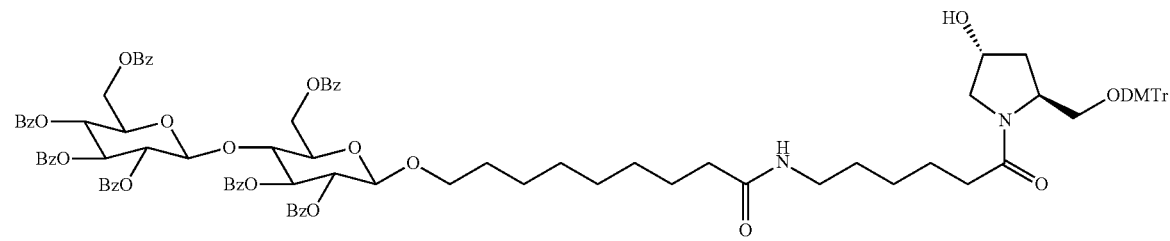
220
1. Succinic anhydride, DMAP, DCM
2. HBTU, DIEA, CPG
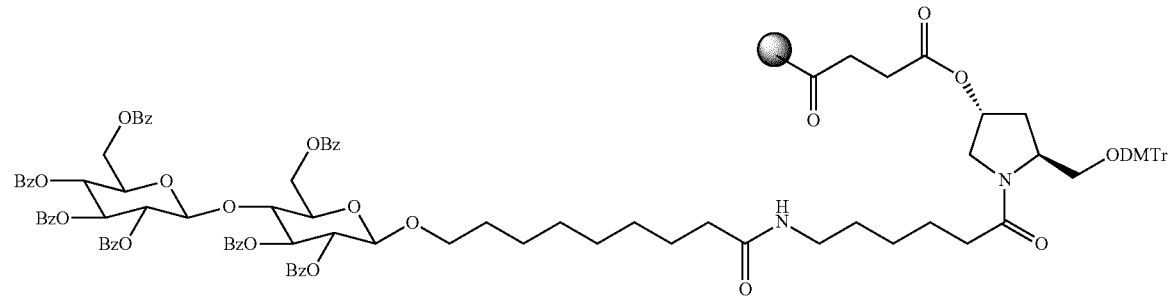
220
(Loading 42 μmol/g)

Compound 217 was synthesized according to the reported procedure (Martin, C.; Karen, P.; Laurence, V. Chem. Pharm. Bull. 2004, 52, 965-971.)

Preparation of 218: 1-Decinol (0.300 g, 1.92 mmol) and trichloroacetimidate 217 (2.33 g, 1.2 eq) was dissolved in anhydrous DCM (10 mL) under argon. MS was added to that and cooled the reaction in an ice bath. $BF_3.Et_2O$ (30 μl) was added to the reaction mixture with stirring. Reaction was monitored by TLC, once the donor reacted the reaction was quenched with TEA and diluted with DCM, filtered off MS and dried. The residue was purified by chromatography (gradient elution 10-40% EtOAc/Hexane) to the compound as a white fluffy solid (2.01 g, 86%). $^1$H NMR ($CDCl_3$, 400 MHz) δ=7.80-8.12(m, 10H), 7.60-7.78(m, 4H), 7.18-7.60(m, 21H), 6.20-6.05(m, 2H), 5.60-5.91 (m, 5H), 5.10-5.43(m, 3H), 3.80-5.02(m, 7H), 3.40-3.56(m, 1H), 1.95-2.10(m, 4H), 1.00-1.60(m, 11H). $^{13}$C NMR ($CDCl_3$, 100 MHz) δ=169.89, 166.51, 166.40, 166.35, 166.32, 166.24, 166.10, 166.03, 165.99, 165.96, 165.86, 165.61, 165.46, 166.38, 165.34, 165.27, 165.23, 163.68, 139.36, 133.71, 133.67, 133.56, 133.40, 133.27, 133.21, 130.12, 130.05, 129.98, 129.95, 129.92, 129.88, 129.80, 129.77, 129.73, 129.68, 129.62, 129.55, 129.50, 129.47, 129.41, 129.40, 129.29, 129.14, 129.11, 129.03, 128.96, 128.87, 128.84, 128.83, 128.78, 128.76, 128.63, 128.56, 128.54, 128.48, 128.37, 128.26, 114.33, 114.26, 100.92, 100.84, 97.04, 96.52, 75.36, 75.17, 74.84, 73.37, 72.95, 72.90, 72.81, 72.57, 72.507, 71.94, 71.58, 71.05, 70.37, 70.27, 70.19, 70.06, 69.86, 69.24, 69.19, 69.02, 63.71, 63.56, 63.20, 62.93, 62.69, 33.96, 33.91, 32.93, 29.60, 29.53, 29.50, 29.46, 29.42, 29.33, 29.30, 29.22, 29.14, 29.06, 29.00. MS. Molecular weight calculated for $C_{71}H_{68}O_{18}$, Cal. 1208.44. Found 1231.4 (M+Na).

Preparation of 219: Compound 218 (7.26 g, 6 mmol) was dissolved in a mixture of Dioxane: Water (100 mL, 3:1). To the reaction mixture lutidine (0.7 mL, 2 eq), followed by $OsO_4$ solution (5 mL. 0.05M solution in $^t$Butanol) were added. Sodium periodate (5.11 g, 4 eq) was added and stirred for 4 hr's at room temperature. Reaction was monitored by TLC, once the starting material was consumed; the mixture was diluted with water and extracted with DCM (3 times) and dried over sodium sulfate. All the solvents were removed and the residue was directly used next reaction. Residue from the above reaction was dissolved in DMF (60 mL) to that Oxone (3.86 g, 1.05 eq) and stirred at ambient temperature for 3 h. Once the starting material was consumed, 10 mL of 1M HCl was added and diluted with Ethyl acetate. Washed with water, brine and dried over sodium sulfate. Solvents were removed and the residue was purified by chromatography (gradient elution 20-40% EtOAc/hexane) to get the compound 219 as a white solid (5.50 g 75%). $^1$H NMR (DMSO-$d_6$, 400 MHz) δ=12.00(bs, 1H), 8.42-7.10(m, 35 H), 6.10-4.5(m, 13H), 4.20-3.30 (m, 3H), 2.20-2.03(m, 3H), 1.50-0.8 (11H). $^{13}$C NMR (DMSO-$d_6$, 100 MHz) δ=174.55, 174.51, 169.13, 165.59, 165.52, 165.39, 165.27, 165.24, 165.14, 164.99, 164.88, 164.75, 164.70, 164.66, 164.60, 164.54, 164.50, 162.92, 165.59, 165.51, 165.39, 165.27, 165.24, 165.14, 164.99, 164.88, 164.75, 164.70, 164.60, 164.54, 164.50, 133.80, 133.71, 133.58, 133.42, 133.29, 133.15, 129.88, 129.42, 129.36, 129.29, 129.23, 129.20, 129.12, 129.07, 129.05, 129.03, 128.91, 128.88, 128.72, 128.59, 128.48, 128.38, 99.96, 99.29, 99.22, 95.96, 95.64, 95.22, 93.10, 75.61, 74.86, 74.57, 74.37, 74.15, 73.59, 73.14, 72.58, 71.46, 71.15, 70.48, 70.31, 70.09, 69.97, 69.00, 68.87, 68.22, 67.81, 63.65, 62.49, 60.73, 59.76, 43.01, 33.68, 33.62, 32.54, 28.84, 28.82, 28.61, 28.55, 28.47, 28.40, 25.47, 25.21, 24.52, 24.43, 20.45. MS. Molecular weight calculated for $C_{70}H_{66}O_{20}$, Cal. 1226.41, Found 1249.4 (M+Na).

Preparation of 220: Compound 219 (1.65 g, 1.37 mmol), hydroxyl proline amine (0.945 g, 1.3 eq) and HBTU (0.623 g, 1.64 mmol) were dissolved in DMF under argon. DIEA (0.71 mL, 3 eq.) was added to that and stirred for 3 hrs at ambient temperature. The reaction was monitored by TLC; once the starting material was consumed the mixture was poured in to an ice water mixture; extracted with ethyl acetate washed with water, brine and dried over sodium sulfate. Solvents was removed and the residue was purified by chromatography (first ethyl acetate followed by a gradient elution 3-10% MeOH/EtOAc) to get the product 220 as a pale yellow solid (1.55 g, 65%). $^1$H NMR (DMSO-$d_6$, 400 MHz) δ=8.20-7.32 (m, 35 H), 7.32-7.10(m, 9H), 6.90-6.82(m, 4H), 6.00-5.63 (m, 4H), 5.41-5.37 (m, 1H), 5.20-5.03 (m, 2H), 4.98 (d, J=4.15 Hz, 1H), 4.90(d, J=4.15 Hz, 1H), 4.88-4.05 (m, 9H), 3.70(s, 6H), 3.65-2.93 (m, 10H), 2.20-0.80(m, 22H). $^{13}$C NMR (DMSO-$d_6$, 100 MHz) δ=171.81, 170.94, 170.90, 170.84, 165.56, 165.53, 165.49, 165.19, 165.12, 164.87, 164.72, 164.63, 164.58, 164.46, 158.09, 158.03, 157.96, 145.08, 144.74, 135.87, 135.73, 135.48, 135.42, 133.80, 133.57, 133.42, 133.29, 129.60, 129.55, 129.26, 129.20, 129.04, 129.00, 128.87, 128.74, 128.69, 128.59, 128.36, 128.34, 128.27, 128.02, 127.86, 127.77, 127.57, 126.74, 126.56, 113.19, 113.09, 99.26, 95.94, 85.77, 85.10, 74.83, 73.58, 72.55, 71.43, 70.44, 70.07, 69.01, 68.87, 68.58, 68.19, 67.45, 65.19, 63.29, 63.48, 63.33, 62.47, 59.75, 55.59, 54.99, 54.96, 53.44, 44.56, 38.21, 36.30, 35.76, 35.41, 34.15, 32.52, 30.74, 30.15, 29.09, 28.84, 28.66, 28.56, 28.52, 26.18, 25.27, 25.22, 24.54, 24.14. 21.22, 20.75, 20.71, 18.59, 14.07, 13.54 MS. Molecular weight calculated for $C_{102}H_{104}N_2O_{24}$, Cal. 1740.70, Found 1263.7 (M+Na).

Preparation of Long Alkyl Chain CPG 221: Hydroxy derivative 220 (1.50 g, 0.862 mmol) was dissolved in DCM (20 mL) to that Succinic anhydride (0.174 g, 2 eq) and DMAP (0.316 g, 3 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under high vacuum to get the succinate. The succinate from the above step and HBTU (0.392 g, 1.2 eq) were dissolved in DMF (30 mL). DIEA (0.450 mL) was added to that and the mixture stirred for 5 minutes under argon. Long chain alkyl amine-CPG (lcaa CPG, 5.30 g, 133 μmol/g) was added to the mixture and gently shaken for 2 h. The CPG was filtered, successively washed with DMF, a mixture of DCM/MeOH, DCM and dried. The dried CPG was transferred into another flask treated with $Ac_2O$ in pyridine (25%) in the presence of TEA (1 mL) for 15 min. under gentle shaking. Finally the CPG was filtered, washed with DCM, DCM:MeOH (9:1), followed by DCM and ether. The CPG 221 was dried under vacuum overnight and the loading was measured as reported (5.62 g, loading: 42 mol/g).

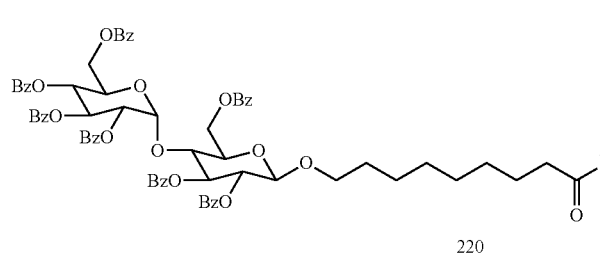
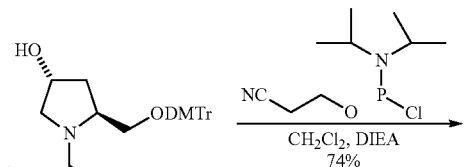

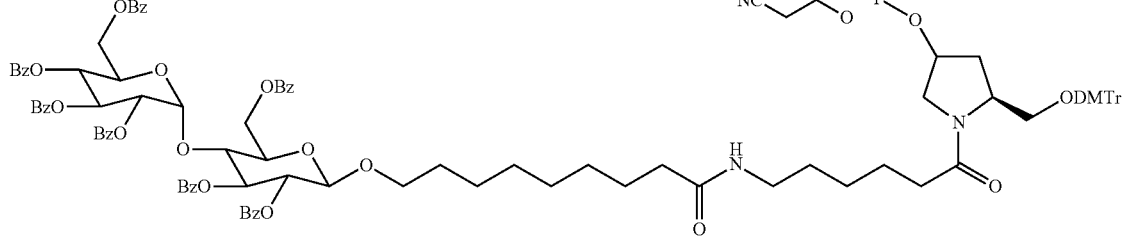

Hydroxy derivative 220 (0.200 g, 0.115 mmol) was dissolved in anhy. DCM (5 mL) to that DIEA (0.80 mL) and chloroamidite reagent (0.068 mL) was added and stirred overnight. The reaction was monitored by TLC, solvents were removed under reduced pressure and charged directly charged to a silica gel column (neutralized with TEA). First eluted with 2:1 (EtOAc/Hexane) followed by EtOAc to get the product (0.150 g, 67%). $^1$H NMR (CDCl$_3$, 400 MHz) δ=7.10-8.12 (m, 48H), 6.85-6.75 (m, 4H) 6.10(t, J=10.19 Hz, 1H), 5.80-5.60(m, 3H), 5.33-5.20 (m, 2H), 5.00-4.06(m, 12H), 3.77 (s, 6H), 3.90-3.05(m, 16H), 2.80-1.01 (27H). $^{31}$P (CDCl$_3$, 161 MHz) δ=145.83, 145.41, 144.95 MS. Molecular weight calculated for $C_{111}H_{121}N_4O_{25}$, Cal. 1940.81. Found 1963.80 (M+Na).

Example 12

RNA Synthesis and Duplex Annealing

1. Oligonucleotide Synthesis:

All oligonucleotides were synthesized on an AKTAoligopilot synthesizer or an ABI 394 synthsizer. Commercially available controlled pore glass solid support (dT-CPG, 500Å, Prime Synthesis) and RNA phosphoramidites with standard protecting groups, 5'-O-dimethoxytrityl N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis unless otherwise specified. The 2'-F phosphoramidites, 5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite were purchased from (Promega). All phosphoramidites were used at a concentration of 0.2M in acetonitrile (CH$_3$CN) except for guanosine which was used at 0.2M concentration in 10% THF/ANC (v/v). Coupling/recycling time of 16 minutes was used. The activator was 5-ethyl thiotetrazole (0.75M, American International Chemicals), for the PO-oxidation Iodine/Water/Pyridine was used and the PS-oxidation PADS (2%) in 2,6-lutidine/ACN (1:1 v/v) was used.

Ligand conjugated strands were synthesized using solid support containing the corresponding ligand. For example, the introduction of carbohydrate moiety/ligand (for e.g., GalNAc) at the 3'-end of a sequence was achieved by starting the synthesis with the corresponding carbohydrate solid support. Similarly a cholesterol moiety at the 3'-end was introduced by starting the synthesis on the cholesterol support. In general, the ligand moiety was tethered to trans-4-hydroxyprolinol via a tether of choice as described in the previous examples to obtain a hydroxyprolinol-ligand moiety. The hydroxyprolinol-ligand moiety was then coupled to a solid support via a succinate linker or was converted to phosphoramidite via standard phosphitylation conditions to obtain the desired carbohydrate conjugate building blocks. See Examples 1-11 for details. Fluorophore labeled siRNAs were synthesized from the corresponding phosphoramidite or solid support, purchased from Biosearch Technologies. The oleyl lithocholic (GalNAc)$_3$ polymer support made in house at a loading of 38.6 μmol/gram. The Mannose (Man)$_3$ polymer support was also made in house at a loading of 42.0 μmol/gram.

Conjugation of the ligand of choice at desired position, for example at the 5'-end of the sequence, was achieved by coupling of the corresponding phosphoramidite to the growing chain under standard phosphoramidite coupling conditions unless otherwise specified. An extended 15 min coupling of 0.1M solution of phosphoramidite in anhydrous CH$_3$CN in the presence of 5-(ethylthio)-1H-tetrazole activator to a solid bound oligonucleotide. Oxidation of the internucleotide phosphite to the phosphate was carried out using standard iodine-water as reported (1) or by treatment with tert-butyl hydroperoxide/acetonitrile/water (10:87:3) with 10 min oxidation wait time conjugated oligonucleotide. Phosphorothioate was introduced by the oxidation of phosphite to phosphorothioate by using a sulfur transfer reagent such as DDTT (purchased from AM Chemicals), PADS and or Beaucage reagent The cholesterol phosphoramidite was synthesized in house, and used at a concentration of 0.1 M in dichloromethane. Coupling time for the cholesterol phosphoramidite was 16 minutes.

Syntheses of 3'-Cholesterol-3'-Carbohydreate containing oligonucleotides was accomplished by coupling of the cholesterol phosphoramidite to the desired carbohydrate bearing solid support followed by coupling of the nucleoside phosphoramdites. PEGylated Oligonucleotides with or without a second ligand was obtained by post-synthetic conjugation of the corresponding PEG-NHS ester to amino-linked sequence. The amino linker was introduced at desired position in a sequence by using a corresponding trans-4-hydroxyprolinol based amino linker or commercially available amino linkers. For example, syntheses of 3'-PEG-3'-GalNAc containing oligonucleotides was accomplished by coupling of trans-4-hydroxyprolinol-amino linker phosphoramidite to the desired GalNAc bearing solid support followed by coupling of the nucleoside phosphoramdites. The oligonucleotide thus obtained was subjected to post-synthetic conjugation with PEG-NHS ester between pH 7.5 and 9 in sodium bicarbonate buffer depends on the nature of the sequence.

2. Deprotection-I (Nucleobase Deprotection)

After completion of synthesis, the support was transferred to a 100 ml glass bottle (VWR). The oligonucleotide was cleaved from the support with simultaneous deprotection of base and phosphate groups with 80 mL of a mixture of ethanolic ammonia [ammonia:ethanol (3:1)] for 6.5 h at 55° C. The bottle was cooled briefly on ice and then the ethanolic ammonia mixture was filtered into a new 250 ml bottle. The CPG was washed with 2×40 mL portions of ethanol/water (1:1 v/v). The volume of the mixture was then reduced to ~30 ml by roto-vap. The mixture was then frozen on dry ice and dried under vacuum on a speed vac.

3. Deprotection-II (Removal of 2' TBDMS Group)

The dried residue was resuspended in 26 ml of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction was then quenched with 50 ml of 20 mM sodium acetate and pH adjusted to 6.5, and stored in freezer until purification.

4. Analysis

The oligoncuelotides were analyzed by high-performance liquid chromatography (HPLC) prior to purification and selection of buffer and column depends on nature of the sequence and or conjugated ligand.

5. PEGylation of Sugar Conjugated Oligonucleotides

Oligonucleotide containing functionalized with an amino linker was treated with PEG-NHS ester of desired molecular weight in sodium bicarbonate buffer between pH 7.5 and 9.0. The progress of the reaction was monitored by HPLC. After completion of the reaction the PEGylated oligonucleotide was purified by HPLC and analyzed by MS.

6. HPLC Purification

The ligand conjugated oligonucleotides were purified reverse phase preparative HPLC. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. Approximately 0.15 OD of desalted oligonucleotidess were diluted in water to 150 μl and then pipetted in special vials for CGE and LC/MS analysis. Compounds were finally analyzed by LC-ESMS and CGE.

7. siRNA Preparation

For the preparation of siRNA, equimolar amounts of sense and antisense strand were heated in 1×PBS at 95° C. for 5 min and slowly cooled to room temperature. Integrity of the duplex was confirmed by HPLC analysis.

TABLE 2

| GalNAc Conjugated duplexes | | | | |
|---|---|---|---|---|
| Target | Duplex ID | SEQ ID No. | S/AS | Sequence 5'-3' |
| PCSK9 | AD-3672 | | A-30693 | GccuGGAGuuuAuucGGAAdTdTsL96 |
| | | | A-18242 | PUUCCGAAUAAACUCCAGGCdTsdT |
| PCSK9 | AD-3673 | | A-30693 | GccuGGAGuuuAuucGGAAdTdTsL96 |
| | | | A-30696 | PuUfcCfgAfaUfaAfaCfuCfcAfgGfcdTdTsL10 |
| PCSK9 | AD-3674 | | A-30694 | GccuGGAGuuuAuucGGAAdTdTsQ11L96 |
| | | | A-18242 | PUUCCGAAUAAACUCCAGGCdTsdT |
| PCSK9 | AD-3718 | | A-30983 | GccuGGAGuuuAuucGGAAdTdTsL101 |
| | | | A-18242 | PUUCCGAAUAAACUCCAGGCdTsdT |
| PCSK9 | AD-3627 | | A-30824 | GccuGGAGuuuAuucGGAAdTdTL96 |
| | | | A-18242 | PUUCCGAAUAAACUCCAGGCdTsdT |
| PCSK9 | AD-3628 | | A-30824 | GccuGGAGuuuAuucGGAAdTdTL96 |
| | | | A-30682 | PuUfcCfgAfaUfaAfaCfuCfcAfgGfcdTdTL43 |
| PCSK9 | AD-3629 | | A-16865 | GccuGGAGuuuAuucGGAAdTsdT |
| | | | A-18242 | PUUCCGAAUAAACUCCAGGCdTsdT |
| PCSK9 | AD-3671 | | A-16865 | GccuGGAGuuuAuucGGAAdTsdT |
| | | | A-30693 | GccuGGAGuuuAuucGGAAdTdTsL96 |
| apoB | AD-6490 | | A-5296 | 5'-GGAAUCuuAuAuuuGAUCcAsA |
| | | | A-5475 | uuGGAUcAAAuAuAAGAuUCcscsU |

TABLE 2 -continued

GalNAc Conjugated duplexes

| Target | Duplex ID | SEQ ID No. | S/AS | Sequence 5'-3' |
|---|---|---|---|---|
| apoB | AD-5544 | | A-5474 | GGAAUCuuAuAuuuGAUCcAAsL10 |
| | | | A-5475 | uuGGAUcAAAuAuAAGAuUCcscsU |
| apoB | AD-3697 | | A-30863 | GGAAUCuuAuAuuuGAUCcAAsL96 |
| | | | A-5475 | uuGGAUcAAAuAuAAGAuUCcscsU |
| apoB | AD-3698 | | A-30864 | GGAAUCuuAuAuuuGAUCcAAsQ11L96 |
| | | | A-5475 | uuGGAUcAAAuAuAAGAuUCcscsU |
| apoB | AD-3699 | | A-30863 | GGAAUCuuAuAuuuGAUCcAAsL96 |
| | | | A-30865 | uuGGAUcAAAuAuAAGAuUCccsUsL10 |
| apoB | AD-3717 | | A-30982 | GGAAUCuuAuAuuuGAUCcAAsL101 |
| | | | A-5475 | uuGGAUcAAAuAuAAGAuUCcscsU |
| apoB | AD-18117 | | A-5474 | GGAAUCuuAuAuuuGAUCcAAsL10 |
| | | | A-31849 | Q38uuGGAUcAAAuAuAAGAuUCcscsU |
| apoB | AD-18118 | | A-30863 | GGAAUCuuAuAuuuGAUCcAAsL96 |
| | | | A-31849 | Q38uuGGAUcAAAuAuAAGAuUCcscsU |
| apoB | AD-18119 | | A-30864 | GGAAUCuuAuAuuuGAUCcAAsQ11L96 |
| | | | A-31849 | Q38uuGGAUcAAAuAuAAGAuUCcscsU |
| apoB | Ad-18648 | | A-31644 | GGAAUCuuAuAuuuGAUCcAAsQ11L90 |
| | | | A-5475 | uuGGAUcAAAuAuAAGAuUCcscsU |
| apoB | AD-18649 | | A-31649 | GGAAUCuuAuAuuuGAUCcAAsQ51Q11L96 |
| | | | A-5475 | uuGGAUcAAAuAuAAGAuUCcscsU |
| apoB | AD-18650 | | A-32147 | GGAAUCuuAuAuuuGAUCcAAsQ11L80 |
| | | | A-547 | uuGGAUcAAAuAuAAGAuUCcscsU |
| apoB | AD-18651 | | A-32148 | Q11-GGAAUCuuAuAuuuGAUCcAAsL96 |
| | | | A-5475 | uuGGAUcAAAuAuAAGAuUCcscsU |
| apoB | AD-18652 | | A-32801 | GGAAUCuuAuAuuuGAUCcAAsQ11L110 |
| | | | A-5475 | uuGGAUcAAAuAuAAGAuUCcscsU |
| apoB | | | A-34132 | GGAAUCuuAuAuuuGAUCcAAsQ8L110 |
| | | | A-5475 | uuGGAUcAAAuAuAAGAuUCcscsU |
| apoB | | | A-34133 | GGAAUCuuAuAuuuGAUCcAAsQ90L110 |
| | | | A-5475 | uuGGAUcAAAuAuAAGAuUCcscsU |
| apoB | | | A-34134 | Q8GGAAUCuuAuAuuuGAUCcAAsL110 |
| | | | A-5475 | uuGGAUcAAAuAuAAGAuUCcscsU |
| apoB | | | A-34135 | Q90GGAAUCuuAuAuuuGAUCcAAsL110 |
| | | | A-5475 | uuGGAUcAAAuAuAAGAuUCcscsU |
| apoB | AD-19031 | | A-33593 | GGAAUCuuAuAuuuGAUCcAAsQ11L117 |
| | | | A-5475 | uuGGAUcAAAuAuAAGAuUCcscsU |
| apoB | | | A-34176 | GGAAUCuuAuAuuuGAUCcAAsL117 |
| | | | A-5475 | uuGGAUcAAAuAuAAGAuUCcscsU |
| apoB | | | A-32800 | GGAAUCuuAuAuuuGAUCcAAsL110 |
| | | | A-5475 | uuGGAUcAAAuAuAAGAuUCcscsU |
| apoB | | | A-34156 | GGAAUCuuAuAuuuGAUCcAAsL82 |
| | | | A-5475 | uuGGAUcAAAuAuAAGAuUCcscsU |
| apoB | | | A-34157 | GGAAUCuuAuAuuuGAUCcAAsL83 |
| | | | A-5475 | uuGGAUcAAAuAuAAGAuUCcscsU |
| FVII | AD-18572 | | A-31843 | GGAUfCfAUfCfUfCfAAGU1CfUfUfACfdTdTsL96 |
| | | | A-31848 | Q11UfAAGACfUfUMAGAUfGAUfCfCfdTsdT |
| FVII | AD-18567 | | A-31844 | GGAUfCfAUfCfUfCfAAGUfCfUfUfACfdTdTsQ51Q11L96 |
| | | | A-4724 | GUfAAGACfUfUfGAGAUfGAUfCfCfdTsdT |
| FVII | AD-18568 | | A-31845 | GGAUfCfAUfCfUfCfAAGUfCfUfUfACfdTdTsQ11L90 |
| | | | A-4724 | GUfAAGACfUfUfGAGAUfGAUfCfCfdTsdT |

TABLE 2 -continued

GalNAc Conjugated duplexes

| Target | Duplex ID | SEQ ID No. | S/AS | Sequence 5'-3' |
|---|---|---|---|---|
| FVII | AD-18569 | | A-31846 | GGAUfCfAUfCfUfCfAAGUfCfUfUfACfdTdTsQ11L80 |
| | | | A-4724 | GUfAAGACfUfUfGAGAUfGAUfCfCfdTsdT |
| FVII | AD-18570 | | A-31847 | Q11GGAUfCfAUfCfUfCfAAGUfCfUfUfACfdTdTsL96 |
| | | | A-4724 | GUfAAGACfUfUfGAGAUfGAUfCfCfdTsdT |
| FVII | AD-18571 | | A-32817 | GGAUfCfAUfCfUtUfAAGUtrfUfUfACfdTdTsQ11L110 |
| | | | A-4724 | GUfAAGACfUfUfGAGAUfQAUfCfCfdTsdT |
| FVII | | | A-35052 | GGAUCAUCUCAAGUCUUACdTsdTsL10 |
| | | | A-4724 | GUfAAGACfUfUfGAGAUfGAUfCfCfdTsdT |
| FVII | | | A-33571 | GGAUfCfAUfCfUfCfAAGUfCfUfUfACfdTdTsL116 |
| | | | A-4724 | GUfAAGACfUfUfGAGAUfGAUfCfCfdTsdT |
| FVII | | | A-33572 | GGAUfCfAUfCfUfCfAAGUfCfUfUfACfdTdTsQ92L96 |
| | | | A-4724 | GUfAAGACfUfUfGAGAUfGAUfCfCfdTsdT |
| FVII | | | A-4639 | GGAUCAUCUCAAGUCUUACdTdT |
| | | | A-4640 | GUAAGACUUGAGAUGAUCCdTdT |
| FVII | | | A-34128 | GGAUfCfAUfCfUfCfAAGUfCfUfUfACfdTdTsQ8L110 |
| | | | A-4724 | GUfAAGACfUfUfGAGAUfGAUfCfCfdTsdT |
| FVII | | | A-34129 | GGAUfCfAUfCfUfCfAAGUfCfUfUfACfdTdTsQ90L110 |
| | | | A-4724 | GUfAAGACfUfUfGAGAUfGAUfCfCfdTsdT |
| FVII | | | A-34130 | Q8GGAUfCfAUfCfUfCfAAGUfCfUfUfACfdTdTsL110 |
| | | | A-4724 | GUfAAGACfUfUfGAGAUfGAUfCfCfdTsdT |
| FVII | | | A-34131 | Q90GGAUfCfAUfCfUfCfAAGUfCfUfUfACfdTdTsL110 |
| | | | A-4724 | GUfAAGACfUfUfGAGAUfGAUfCfCfdTsdT |
| FVII | AD-19032 | | A-33573 | GGAUfCfAUftfUfCfAAGUfCfUfUfACfdTdTsQ11L117 |
| | | | A-4724 | GUfAAGACfUfUfGAGAUfGAUfCfCfdTsdT |
| FVII | AD-19033 | | A-33570 | GGAUfCfAUfCfUfCfAAGUfCflifUfACfdTdTsQ91L96 |
| | | | A-4724 | GUfAAGACfUfUfGAGAUfGAUfCfCfdTsdT |
| FVII | AD-18047 | | A-31841 | GGAUfCfAUfCfUfCfAAGUfCfUfUfACfdTdTsQ11L96 |
| | | | A-4724 | GUfAAGACfUfUIUfGAGAUfGAUfCfCfdTsdT |

Note:
S is PS linkge,
lowercase s 2'-O-methyl nucleotide,
Nf is 2'-fluoro nucleotide,
P is a phosphate group,
L10 is N-(cholesterylcarboxamidocaproyl)-4-hydroxyprolinol (Hyp-C6-Chol),
L43 is Quasar 570 CPG (BG5-5063, Biosearch Tech),
L80 is N-[tris(GalNAc-alkyl)-amidohexanoylcarboxamidoethyl-dithio-butyryl]-4-hydroxyprolinol (Hyp-S-S-(GalNAc-alkyl)3),
L82 is PEG 5 K CarboxymethylNHS,
L83 is PEG 20 K CarboxymethylNHS,
L96 is N-[tris(GalNAc-alkyl)-amidodecanoyl)]-4-hydroxyprolinol (Hyp-(GalNAc-alkyl)3),
L110 is N-[N',N"-(bis(GalNAc-alkyl)-lysine)-aminocapryl]-4-hydroxyprolinol (Hyp-Lys-(GalNAc-alkyl)2),
L101 is Hyp-(GalNAc-TEG)3-LCO,
L116 is N-(lithocholylcarboxamidocaproyl)-4-hydroxyprolinol (Hyp-C6-lithocholic acid),
Q8 is N-(aminocaproyl)prolinol-4-phosphate,
Q11 is N-(cholesterylcarboxamidocaproyl)prolinol-4-phosphate,
Q38 is Quasar 570 phosphate (BNS-5063, Biosearch Tech),
Q90 is N-(PEG(20 K)pentylcarboxamidocaproyl)-4-hydroxyprolinol,
Q91 is N-(myristylcarboxamidocaproyl)-4-hydroxyprolinol (Hyp-C6-C14),
Q92 is N-(lithocholylcarboxamidocaproyl)-4-hydroxyprolinol (Hyp-C6-lithocholic acid),
Q51 is 6-hydroxyhexyldithiohexylphosphate (Thiol-Modifier C6 S-S Glen Res. 10-1936) and
L117 is N-[N',N"-(bis(glucose-alkyl)-lysine)-aminocapryl]-4-hydroxyprolinol (Hyp-Lys-(Gluc-alkyl)2).

Example 13

In Vitro Silencing Activity with Various Chemical Modifications on apoB siRNA

The IC50 for each modified siRNA was determined in Hep3B cells by standard reverse transfection using Lipofectamine RNAiMAX. In brief, reverse transfection was carried out by adding 5 µL of Opti-MEM to 5 µL of siRNA duplex per well into a 96-well plate along with 10 µL of Opti-MEM plus 0.5 µL of Lipofectamine RNAiMax per well (Invitrogen, Carlsbad Calif. cat #13778-150) and incubating at room temperature for 15-20 minutes. Following incubation, 100 µL of complete growth media without antibiotic containing 12,000-15,000 Hep3B cells was then added to each well. Cells were incubated for 24 hours at 37° C. in an atmosphere of 5% $CO_2$ prior to lysis and analysis of ApoB and GAPDH mRNA by bDNA (Quantigene). Seven different siRNA concentrations ranging from 10 nM to 0.6 µM were assessed for IC50 determination and ApoB/GAPDH for ApoB transfected cells was normalized to cells transfected with 10 nM Luc siRNA.

The table below discloses "S ID" sequences as SEQ ID NO: 25 and "AS ID" sequences as SEQ ID NO: 26.

| Duplex | S ID | S 5'-3' | AS ID | AS 5'-3' | IC50 (nM) |
|---|---|---|---|---|---|
| AD-6490 | A-5296 | GGAAUCuuAuAuuuGAUCcAsA | A-5475 | uuGGAUcAAAuAuAAGAuUCcscsU | 0.0401 |
| AD-5544 | A-5474 | GGAAUCuuAuAuuuGAUCcAAs-Chol | A-5475 | uuGGAUcAAAuAuAAGAuUCcscsU | 0.5329 |
| AD-3698 | A30864 | GGAAUCuuAuAuuuGAUCcAAs-Chol-GalNAc3 | A-5475 | uuGGAUcAAAuAuAAGAuUCcscsU | 0.5677 |
| AD-3697 | A-30863 | GGAAUCuuAuAuuuGAUCcAAs GAlNAc3 | A-5475 | uuGGAUcAAAuAuAAGAuUCcscsU | 0.0336 |
| AD-25108 | A-56026 | GfgAfaUcUfuAfuAfuUfuGfaUfcCfasAf | A-55358 | PuUfgFfaUfcAfaAfuAfuAfaGfaUfuCfcsCfsu | 0.0231 |
| AD-27816 | A-63125 | GfgAfaUfcUfuAfuAfuUfuGfaUfcCfaAf-Chol | A-55358 | PuUfgFfaUfcAfaAfuAfuAfaGfaUfuCfcsCfsu | 0.0827 |
| AD-27818 | A-63127 | GfgAfaUfcUfuAfuAfuUfuGfaUfcCfaAf-Chol-GalNAc3 | A-55358 | PuUfgFfaUfcAfaAfuAfuAfaGfaUfuCfcsCfsu | 0.054 |
| AD-27817 | A-63126 | GfgAfaUfcUfuAfuAfuUfuGfaUfcCfaAf-GalNAc3 | A-55358 | PuUfgFfaUfcAfaAfuAfuAfaGfaUfuCfcsCfsu | 0.014 |

Example 14

Figure 2:
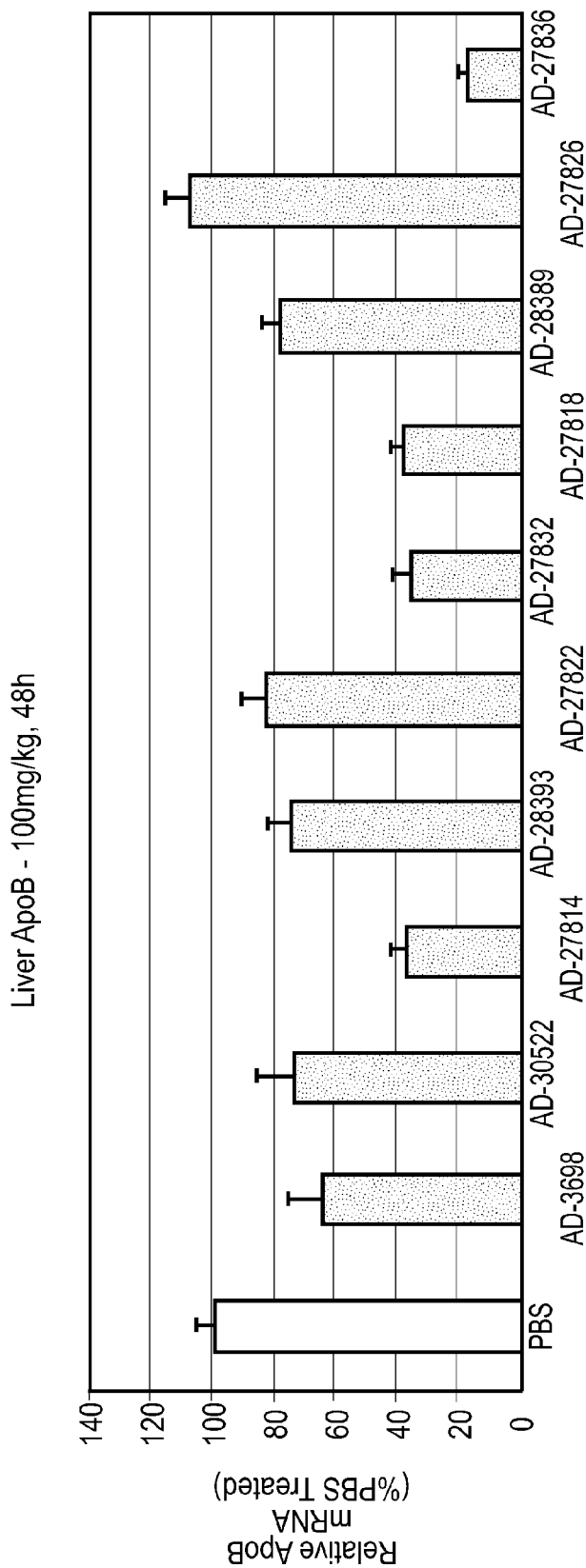
FIG. 2. In vivo silencing of ApoB siRNAs containing chemically modified motifs in combination with Chol-GalNAc3 conjugate.

In Vivo Silencing Activity of Cholesterol-(GalNAc)3 Conjugated apoB siRNAs with Various Motifs Relative to the Parent AD-3698 siRNA IV Bolus dosing of ApoB-Chol/GalNAc3 siRNAs in C57/BL6 mice (5/group, 8-10 weeks old, Charles River Laboratories, MA) was performed by low volume tail vein injection using a 27G needle at a dose volume of 10 ul/g. A single 100 mg/kg dose was administered and mice were sacrificed 48 hours later. Livers were harvested and flash frozen in liquid nitrogen followed by storage at –80 C.

bDNA Analysis: Frozen livers were ground using 6850 Freezer/Mill Cryogenic Grinder (SPEX CentriPrep, Inc) and powders stored at –80° C. until analysis. ApopB and GAPDH mRNA levels were detected using the branched-DNA technology based QuantiGene 1.0 Reagent System (Panomics, Fremont, Calif., USA) according to the protocol. 10-20 mg of frozen liver powders was lysed in 1000 ul of 0.3 ug/ml Proteinase K (Epicentre, #MPRK092) in Tissue and Cell Lysis Solution (Epicentre, #MTC096H) at 65° C. for 40 minutes. Then 10 ul of the lysates were added to 90 ul of Lysis Working Reagent (1 volume of stock Lysis Mixture in two volumes of water) and incubated at 55 C overnight on Panomics capture plates with probe sets specific to mouse ApoB and mouse GAPDH (Panomics, USA). Capture plates then were processed for signal amplification and detection according to the protocol and chemiluminescence was read as relative light units (RLUs) on a microplate luminometer Victor2-Light (Perkin Elmer). The ratio of ApoB mRNA to GAPDH mRNA in liver lysates was averaged over each treatment group and compared to a control group treated with PBS Results: As shown in FIG. 2, as compared to the parent AD-3698 siRNA, treatment with alternating motif with cholesterol-(GalNAc)3 conjugated siRNA (AD-27818) resulted in lowering of ApoB transcript levels (~65% vs ~40%, as indicated by a smaller ApoB to GAPDH transcript ratio when normalized to a PBS control group), indicating that the alternating motif with cholesterol-(GalNAc)3 conjugated siRNAs have superior knockdown.

TABLE 3

Sequences for comparison of cholesterol conjugated and cholesterol-(GalNAc)3 conjugated siRNAs.

| Duplex | Target | S ID | S 5'-3' | AS ID | AS 5'-3' |
|---|---|---|---|---|---|
| AD-3698 | ApoB | A-30864 | GGAAUCuuAuAuuuGAUCcAAsQ11L96 | A-5475 | uuGGAUcAAAuAuAAGAuUCcscsU |
| AD-30522 | ApoB | A-63123 | GGAAucuuAuAuuuGAuccAAQ11L96 | A-5475 | uuGGAUcAAAuAuAAGAuUCcscsU |
| AD-27814 | ApoB | A-63123 | GGAAucuuAuAuuuGAuccAAQ11L96 | A-55358 | PuUfgGfaUfcAfaAfuAfuAfaGfaUfuCfcsCfsu |
| AD-28393 | ApoB | A-63123 | GGAAucuuAuAuuuGAuccAAQ11L96 | A-62289 | PuUfgGfaUfcAfaAfuAfuAfaGfaUfuCfcCfuL131 |
| AD-27822 | ApoB | A-63123 | GGAAucuuAuAuuuGAuccAAQ11L96 | A-55359 | PuUfgGfaUfcAfaAfuAfuAfaGfaUfuCfc(Aeos)(Aeo) |
| AD-27832 | ApoB | A-63123 | GGAAucuuAuAuuuGAuccAAQ11L96 | A-63120 | PuUfgGfaUfcAfaAfuAfuMuAfaGfaUfuCf(m5Ceos)(m5Ceos)U |

TABLE 3 -continued

Sequences for comparison of cholesterol conjugated and cholesterol-(GalNAc)3 conjugated siRNAs.

| Duplex | Target | S ID | S 5'-3' | AS ID | AS 5'-3' |
|---|---|---|---|---|---|
| AD-27818 | ApoB | A-63127 | GfgAfaUfcUfuAfuAfuUfuGfaUfcCfaAfQ11L96 | A-55358 | PuUfgGfaUfcAfaAfuAfuAfaGfaUfuCfcsCfsu |
| AD-28389 | ApoB | A-63127 | GfgAfaUfcUfuAfuAfuUfuGfaUfcCfaAfQ11L96 | A-62289 | PuUfgGfaUfcAfaAfuAfuAfaGfaUfuCfcCfuL131 |
| AD-27826 | ApoB | A-63127 | GfgAfaUfcUfuAfuAfuUfuGfaUfcCfaAfQ11L96 | A-55359 | PuUfgGfaUfcAfaAfuAfuAfaGfaUfuCfc(Aeos)(Aeo) |
| AD-27836 | ApoB | A-63127 | GfgAfaUfcUfuAfuAfuUfuGfaUfcCfaAfQ11L96 | A-63120 | PuUfgGfaUfcAfaAfuAfuAfaGfaUfuCf(m5Ceos)(m5Ceos)U |

Lower case letters represent 2'-O-Me modified nucleotides;
Chol is cholesterol,
L96 is N-[tris(GalNAc-alkyl)-amidodecanoyl]-4-hydroxyprolinol Hyp-(GalNAc-alkyl)3;
L131 is N-(caproyl-4-hydroxyprolinol (Hyp-C6),
Q11 is N-(cholesterylcarboxamidocaproyl)prolinol-4-phosphate,
s is phosphorothioate linkage,
Aeo is 2'-O-methoxyethyladenosine-3'-phosphate,
Aeos is 2'-O-methoxyethyladenosine-3'-phosphorothioate,
m5Ceos is 2'-O-methoxyethyl-5-methylcytidine-3'-phosphorothioate, and
P is phosphate

Example 15

Mouse PK Study

Protocol: Mice were dosed at 100 mg/kg siRNA-Conjugate by i.v. or subcutaneous injection at a dose volume of 10 ul/g (n=2 per time point). At each time point indicated in the table below, 2 mice were sacrificed and blood was collected via the hepatic portal vein and collected into $K_2$EDTA-coated tubes, mixed by inversion, and placed on wet ice. The animals were then perfused with saline and the livers were harvested and flash frozen in liquid nitrogen. Blood was processed to plasma by centrifugation immediately after collection (2,000 g for 10 min at 4° C.). Plasma samples were separated from the RBC pellet, and aliquoted into eppendorf tubes for storage at −80 C.

Frozen livers were ground using a 6850 Freezer/Mill Cryogenic Grinder (SPEX CentriPrep, Inc) and powders stored at −80° C. until analysis. The amount of siRNA per g of liver tissue and per mL of plasma was quantitated using a Attoprobe assay.

PK study samples: 100 mg/kg at 24, 48, 96 and 168 h post-dose

The table below discloses "S ID"sequences as SEQ ID NO: 25 and "AS ID"sequences as SEQ ID NO: 26.

| Group | Duplexes | Dose (mg/kg) | Route | No. of Females | Blood and Tissues Collection Time Points (hours) | Tissues Harvested |
|---|---|---|---|---|---|---|
| 1 | AD-3698 (Chol-GalNAc3 Parent) | 100 | I.v. and s.c. | 44 | .083, 0.25, 0.5, 1, 2, 4, 8, 24, 48, 96, 168 | Liver, Jejunum, Kidney, Spleen, Plasma |
| 2 | AD-27818 (Chol-GalNAc3 New) | 100 | I.v. and s.c. | 44 | | |
| 3 | AD-3697 (GalNAc3 Parent) | 100 | I.v. and s.c. | 44 | | |
| 4 | AD-27817 (GalNAc3 New) | 100 | I.v. and s.c. | 44 | | |
| 5 | PBS | — | S.c. | | | |

| Duplex | S ID | S 5'-3' | AS ID | AS 5'-3' |
|---|---|---|---|---|
| AD-3698 | A-30864 | GGAAUCuuAuAuuuGAUCcAAsQ11L96 | A-5475 | uuGGAUcAAAuAuAAGAuUCcscsU |
| AD-3697 | A-30863 | GGAAUCuuAuAuuuGAUCcAAsL96 | A-5475 | uuGGAUcAAAuAuAAGAuUCcscsU |
| AD-27818 | A-63127 | GfgAfaUfcUfuAfuAfuUfuGfaUfcCfaAfQ11L96 | A-55358 | PuUfgGfaUfcAfaAfuAfuAfaGfaUfuCfcsCfsu |
| AD-27817 | A-63126 | GfgAfaUfcUfuAfuAfuUfuGfaUfcCfaAfL96 | A-55358 | PuUfgGfaUfcAfaAfuAfuAfaGfaUfuCfcsCfsu |

Q11 = Cholesterol
L96 = Gal NAc3

Figure 3:
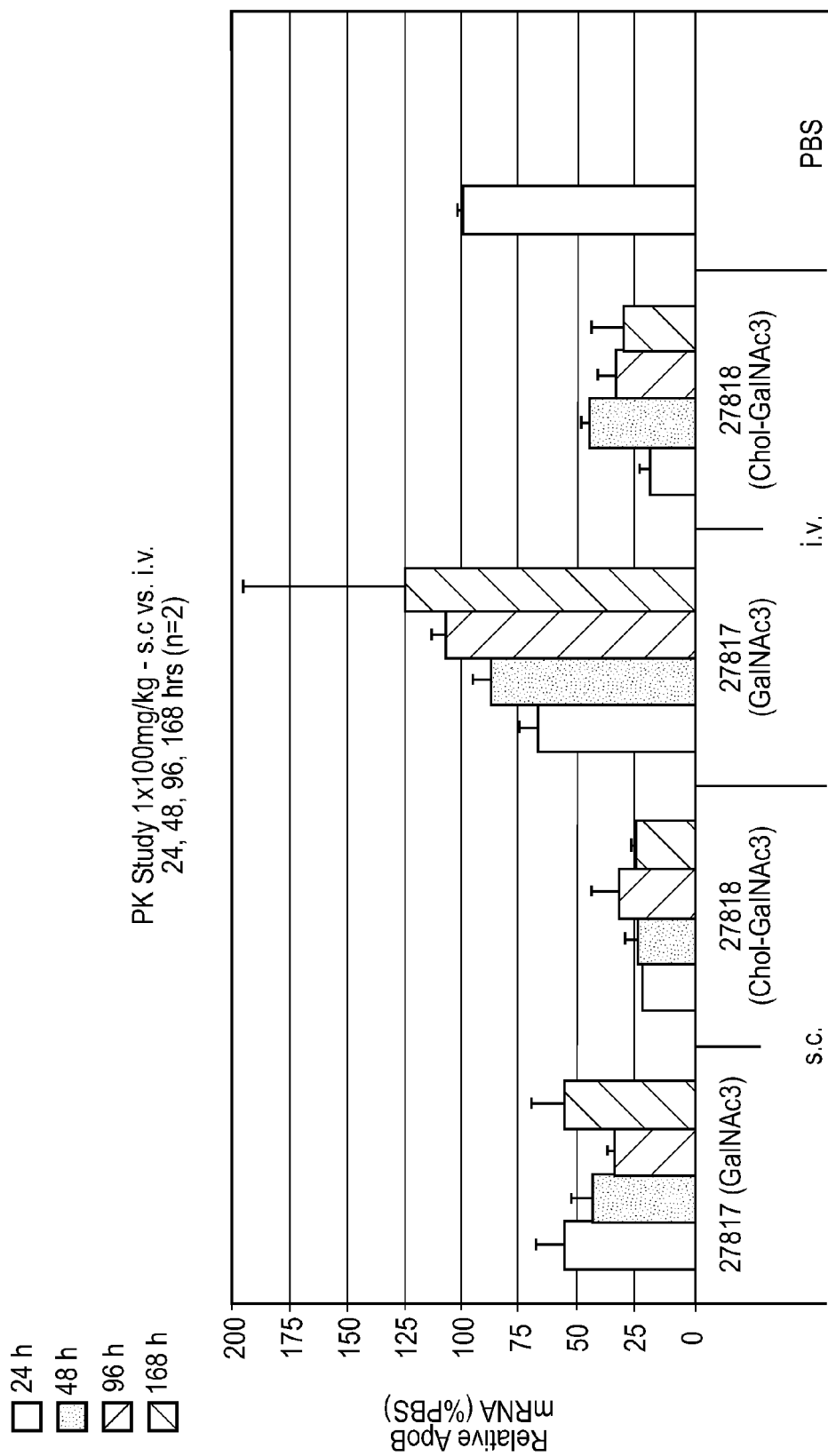
FIG. 3. PD-Liver Silencing After SC Dosing of GalNAc$_3$ Conjugates PK Study Samples: 100 mg/kg 24, 48, 96 and 168 h Post-dose.

FIG. 3 shows similar levels of silencing for SC and IV dosing of AD-27818 with durable silencing up to day 7. Approximately 65% ApoB silencing 96 h after SC dosing of AD-27817 (GalNAc$_3$).

Example 16

Figure 4:
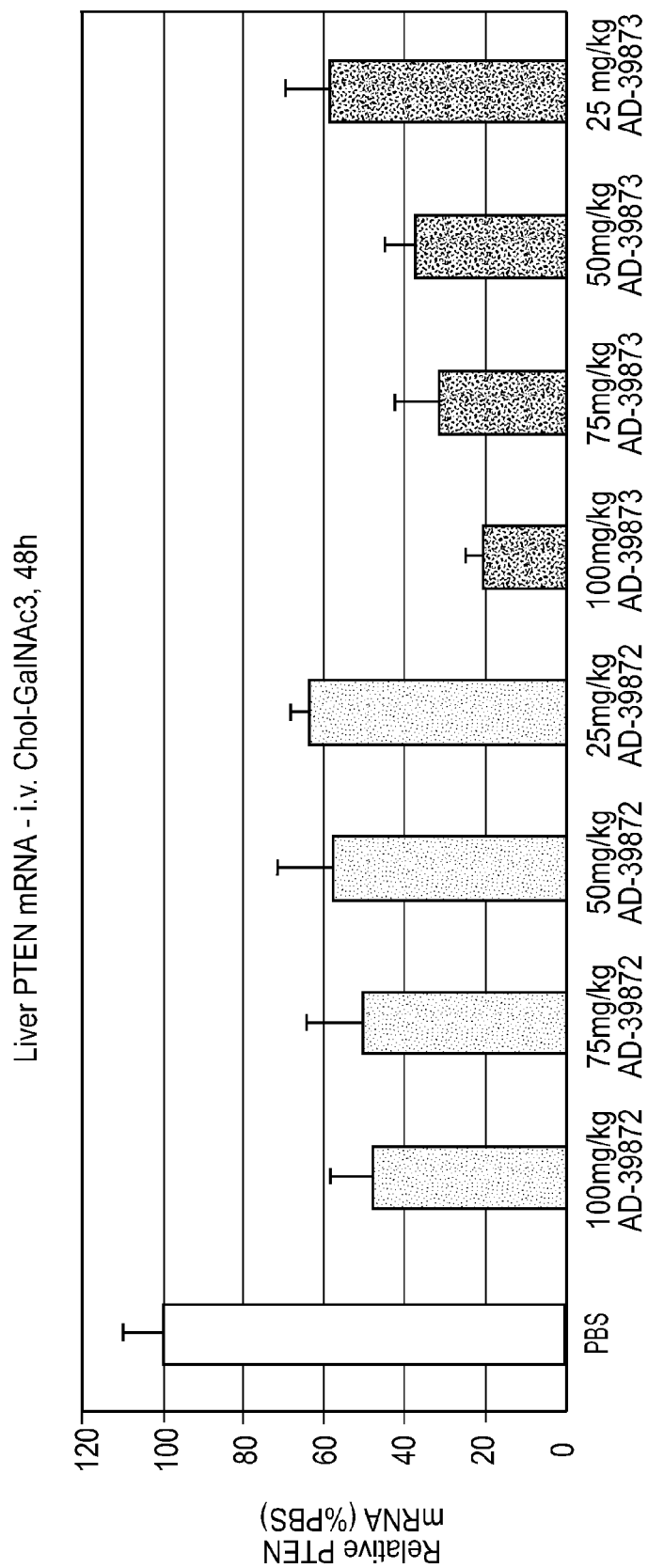
FIG. 4. In vivo silencing of PTEN siRNAs containing chemically modified motifs in combination with Chol-GalNAc3 conjugate.

In Vivo Silencing Activity of Cholesterol-(GalNAc)3 Conjugated PTEN siRNAs with Various Motifs Relative to the Parent AD-3698 siRNA IV Bolus dosing of PTEN-Chol/GalNAc3 siRNAs in C57/BL6 mice (5/group, 8-10 weeks old, Charles River Laboratories, MA) was performed by low volume tail vein injection using a 27G needle at a dose volume of 10 ul/g. Mice received a single i.v. dose at 100, 75, 50 or 25 mg/kg and were sacrificed 48 hours later. Livers were harvested and flash frozen in liquid nitrogen followed by storage at −80 C.

bDNA Analysis: Frozen livers were grinded using 6850 Freezer/Mill Cryogenic Grinder (SPEX CentriPrep, Inc) and powders stored at −80° C. until analysis. PTEN and GAPDH mRNA levels were detected using the branched-DNA technology based QuantiGene 2.0 Reagent System (Panomics, Fremont, Calif., USA) according to the protocol. 10-20 mg of frozen liver powders was lysed in 1000 ul of 0.3 ug/ml Proteinase K (Epicentre, #MPRK092) in Tissue and Cell Lysis Solution (Epicentre, #MTC096H) at 65° C. for 40 minutes. Then 10 ul of the lysates were added to 90 ul of Lysis Working Reagent (1 volume of stock Lysis Mixture in two volumes of water) and incubated at 55 C overnight on Panomics capture plates with probe sets specific to mouse PTEN and mouse GAPDH (Panomics, USA). Capture plates then were processed for signal amplification and detection according to the protocol and chemiluminescence was read as relative light units (RLUs) on a microplate luminometer Victor2-Light (Perkin Elmer). The ratio of PTEN mRNA to GAPDH mRNA in liver lysates was averaged over each treatment group and compared to a control group treated with PBS Results: As shown in FIG. 4, treatment with alterning motif with cholesterol-(GalNAc)3 conjugated PTEN siRNAs resulted in lowering of PTEN transcript levels (as indicated by a smaller PTEN to GAPDH transcript ratio when normalized to a PBS control group), indicating that the alternating motif with cholesterol-(GalNAc)3 conjugated siRNAs have superior knockdown. It was found that the best PTEN-Chol/GalNAc3 conjugate shows similar efficacy in vivo to best corresponding apoB conjugate suggesting that the motifs in combination with the conjugate is sequence independent.

TABLE 4

Sequences for PTEN cholesterol-(GalNAc)3 conjugated siRNAs with alternating motif

| Duplex ID | S ID | Sequence 5'-3' | AS ID | Sequence 5'-3' | Hep3B IC50 (nM) |
| --- | --- | --- | --- | --- | --- |
| AD-39872 | A-80979.1 | GfaUfgAfuGfuUfuGfaAfaCfuAfuUfdTdTQ11L96 | A-81738.1 | aAfuAfgUfuUfcAfaAfcAfuCfaUfcdTsdT | 0.013 |
| AD-39873 | A-80979.1 | GfaUfgAfuGfuUfuGfaAfaCtuAfuUfdTdTQ11L96 | A-81739.1 | aAfuAfgUfuUfcAfaAfcAfuCfaUfc(Teos)(Teos)G | 0.008 |

Lower case letters represent 2'-O-Me modified nucleotides;
L96 is N-[tris(GalNAc-alkyl)-amidodecanoyl]-4-hydroxyprolinol Hyp-(GalNAc-alkyl)3,
s is phosphorothioate linkage,
Teos is 2'-O-methoxyethyl-5-methyluridine-3'-phosphorothioate, and
P is phosphate.

---

We claim:

1. An iRNA duplex agent capable of silencing a target gene in vivo, comprising:
   (a) a sense strand, wherein said sense strand comprises
      (i) an alternating motif with at least 2 different chemically modified nucleotides; and
      (ii) one or more carbohydrate ligand; and
   (b) an antisense strand, wherein said antisense strand comprises
      (i) an alternating motif with at least 2 different chemically modified nucleotides,
   wherein the alternating motif is within the duplex region and the composition optionally further comprises one or more overhangs and/or capping groups.

2. The iRNA duplex agent of claim 1, further comprising a phosphate or phosphate derivative at the 5' carbon position of the antisense strand.

3. The iRNA duplex agent of claim 1, further comprising at least one phosphorothioate internucleotide linkage; or at least one methylphosphonate internucleoside linkage.

4. The iRNA duplex agent of claim 1, wherein the chemically modified nucleotide is selected from the group consisting of LNA, HNA, CeNA, 2'-methoxyethyl, 2'-OCH$_3$, 2'-O-allyl, 2'-C-allyl, and 2'-fluoro.

5. The iRNA duplex agent of claim 1, wherein the chemically modified nucleotides are 2'-OCH$_3$ and 2'-F.

6. The iRNA duplex agent of claim 1, wherein the overhang is at least 2 nucleotides in length and is selected from the group consisting of thymidine (T), 2'-O-methoxyethyl-5-methyluridine(Teo), 2'-O-methoxyethyladenosine (Aeo), 2-O-methoxyethyl-5-methylcytidine (m5Ceo), and combinations thereof, and optionally comprises a phosphorothioate between the two nucleotides, wherein the 2 nucleotides can be the same or different.

7. The iRNA duplex agent of claim 1, wherein the overhang can form a mismatch with the target mRNA or it can be fully complemented with the target mRNA.

8. The iRNA duplex agent of claim 1, wherein the duplex region is between 12-30 nucleotides in length.

9. The iRNA duplex agent of claim 1, wherein the carbohydrate ligand is attached to the 3' end of the sense strand.

10. The iRNA duplex agent of claim 1,
   wherein said sense strand comprises
      (i) an alternating 2'-fluoro modification, and
      (ii) one or more carbohydrate ligand at the 3'-end; and
   wherein said antisense strand comprises
      (i) an alternating 2'-fluoro modification; and
      (ii) a phosphorylated 5' terminal antisense nucleotide.

11. The iRNA duplex agent of claim 10, further comprising at least one phosphorothioate internucleotide linkage; or at least one methylphosphonate internucleoside linkage.

12. The iRNA duplex agent of claim 10, wherein the chemically modified nucleotide is selected from the group consisting of LNA, HNA, CeNA, 2'-methoxyethyl, 2'-OCH$_3$, 2'-O-allyl, 2'-C-allyl, and 2'-fluoro.

13. The iRNA duplex agent of claim 10, wherein the chemically modified nucleotides are 2'-OCH$_3$ and 2'-F.

14. The iRNA duplex agent of claim 10, wherein the overhang is at least 2 nucleotides in length and is selected from the group consisting of thymidine (T), 2'-O-methoxyethyl-5-methyluridine (Teo), 2'-O-methoxyethyladenosine (Aeo), 2'-O-methoxyethyl-5-methylcytidine (m5Ceo), and combinations thereof, and optionally comprises a phosphorothioate between the two nucleotides, wherein the 2 nucleotides can be the same or different.

15. The iRNA duplex agent of claim 10, wherein the overhang can form a mismatch with the target mRNA or it can be fully complemented with the target mRNA.

16. The iRNA duplex agent of claim 10, wherein the duplex region is between 12-30 nucleotides in length.

17. An iRNA duplex agent comprising a compound having the structure shown in formula (I'):

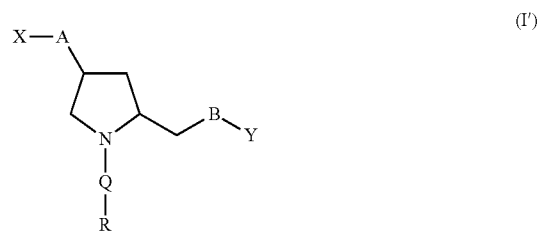

(I')

wherein:

A and B are each independently for each occurrence O, N(R$^N$) or S;

X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, annucleoside, —P(Z')(Z")O—R$^1$-Q'-R$^2$—OP(Z''')(Z"") O-oligonucleotide, or an oligonucleotide, —P(Z')(Z")-formula (I), -P(Z')(Z")— or -Q-R;

wherein the oligonucleotide comprises
   (a) a sense strand, wherein said sense strand comprises
      (i) an alternating 2'-fluoro modification and
      (ii) at least one ligand; and
   (b) an antisense strand, wherein said antisense strand comprises
      (i) an alternating 2'-halogen modification; and
      (ii) a first 5' terminal antisense nucleotide, wherein said first 5' terminal antisense nucleotide is phosphorylated at its 5' carbon position;

R is L$^1$ or has the structure shown in formula (II)-(V)

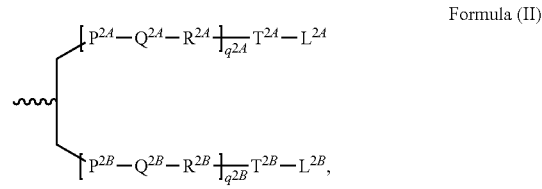

Formula (II)

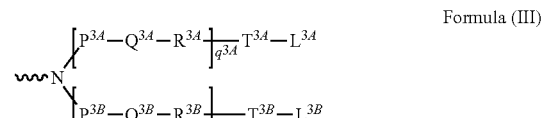

Formula (III)

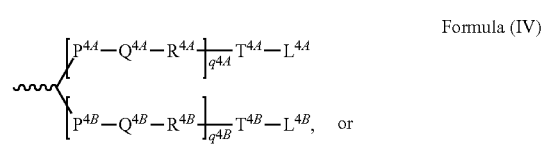

Formula (IV)

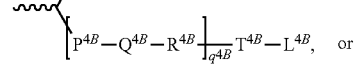

-continued

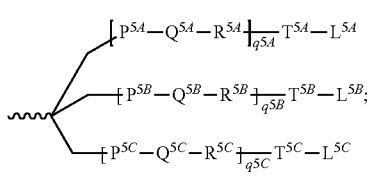
Formula (V)

$q^{2A}$, $q^{2B}$, $q^{3A}$, $q^{3B}$, $q4^A$, $q^{4B}$, $q^{5A}$, $q^{5B}$ and $q^{5C}$ represent independently for each occurrence 0-20 and wherein the repeating unit can be the same or different;

Q and Q' are independently for each occurrence absent, —$(P^7-Q^7-R^7)_p$-$T^7$- or -$T^7$-$Q^7$-$T^{7'}$-B-$T^{8'}$-$Q^8$-$T^8$;

$P^{2A}$, $P^{2B}$, $P^{3A}$, $P^{3B}$, $P^{4A}$, $P^{4B}$, $P^{5A}$, $P^{5B}$, $P^{5C}$, $P^7$, $T^{2A}$, $T^{2B}$, $T^{3A}$, $T^{3B}$, $T^{4A}$, $T^{4B}$, $T^{5A}$, $T^{5B}$, $T^{5C}$, $T^7$, $T^{7'}$, $T^8$ and $T^{8'}$ are each independently for each occurrence absent, CO, NH, O, S, OC(O), NHC(O), $CH_2$, $CH_2NH$ or $CH_2O$;

B is —$CH_2$—$N(B^L)$—$CH_2$—;

$B^L$ is -$T^B$-$Q^B$-$T^{B'}$-$R^x$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$, $Q^7$, $Q^8$ and $Q^B$ are independently for each occurrence absent, alkylene, substituted alkylene wherein one or more methylenes can be interrupted or terminated by one or more of O, S, S(O), $SO_2$, $N(R^N)$, $C(R')$=$C(R'')$, C≡C or C(O);

$T^B$ and $T^{B'}$ are each independently for each occurrence absent, CO, NH, O, S, OC(O), OC(O)O, NHC(O), NHC(O)NH, NHC(O)O, $CH_2$, $CH_2NH$ or $CH_2O$;

$R^x$ is a carbohydrate;

$R^1$, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^7$ are each independently for each occurrence absent, NH, O, S, $CH_2$, C(O)O, C(O)NH, $NHCH(R^a)C(O)$, —C(O)—$CH(R^a)$—NH—, CO, CH=N—O,

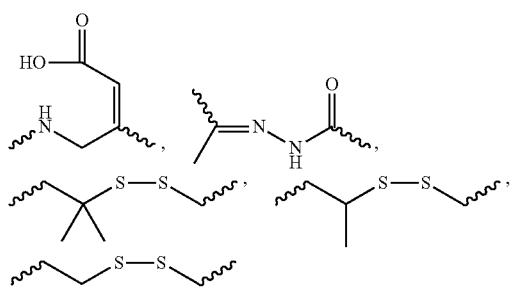

or heterocyclyl;

$L^1$, $L^{2A}$, $L^{2B}$, $L^{3A}$, $L^{3B}$, $L^{4A}$, $L^{4B}$, $L^{5A}$, $L^{5B}$ and $L^{5C}$ are each independently for each occurrence a carbohydrate, e.g., monosaccharide, disaccharide, trisaccharide, tetrasaccharide, oligosaccharide, polysaccharide;

R' and R" are each independently H, $C_1$-$C_6$ alkyl, OH, SH or $N(R^N)_2$;

$R^N$ is independently for each occurrence methyl, ethyl, propyl, isopropyl, butyl or benzyl;

$R^a$ is H or an amino acid side chain;

Z', Z", Z''' and Z'''' are each independently for each occurrence O or S;

p represents independently for each occurrence 0-20.

18. The iRNA duplex agent of claim 17, wherein the iRNA duplex agent further comprises at least one structure of formula (VI)

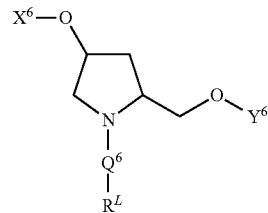
Formula (VI)

wherein $X^6$ and $Y^6$ are each independently H, a hydroxyl protecting group, a phosphate group, a phosphodiester group, an activated phosphate group, an activated phosphate group, a phosphoramidite, a solid support, —P(Z')(Z")O-nucleoside, —P(Z')(Z")O-oligonucleotide, a lipid, a PEG, a steroid, a polymer, —P(Z')(Z")O—$R^1$-Q'-$R^2$—OP(Z''')(Z'''')O-oligonucleotide, a nucleotide, or an oligonucleotide, —P(Z')(Z")-formula (I) or —P(Z')(Z")—;

$Q^6$ is absent or —$(P^6$-$Q^{6'},R^6)_v$-$T^6$-;

$P^6$ and $T^6$ are each independently for each occurrence absent, CO, NH, O, S, OC(O), NHC(O), $CH_2$, $CH_2NH$ or $CH_2O$;

$Q^{6'}$ is independently for each occurrence absent, alkylene, substituted alkylene wherein one or more methylenes can be interrupted or terminated by one or more of O, S, S(O), $SO_2$, $N(R^N)$, $C(R')$=$C(R'')$, C≡C or C(O);

$R^6$ is independently for each occurrence absent, NH, O, S, $CH_2$, C(O)O, C(O)NH, $NHCH(R^a)C(O)$, —C(O)—CH$(R^a)$—NH—, CO, CH=N—O,

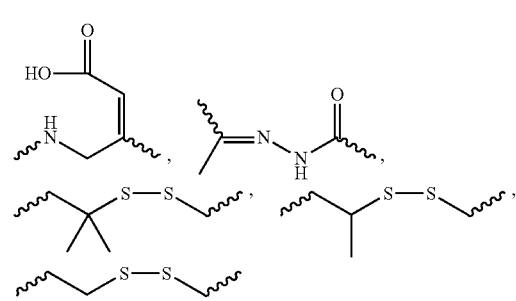

or heterocyclyl;

R' and R" are each independently H, $C_1$-$C_6$ alkyl, OH, SH, $N(R^N)_2$;

$R^N$ is independently for each occurrence H, methyl, ethyl, propyl, isopropyl, butyl or benzyl;

$R^a$ is H or an amino acid side chain;

Z', Z", Z''' and Z'''' are each independently for each occurrence O or S;

v represents independently for each occurrence 0-20;

$R^L$ is a lipophile or a cationic lipid.

19. The iRNA duplex agent of claim 18, wherein $R^L$ is a lipophile.

20. The iRNA duplex agent of claim 18, wherein $R^L$ is cholesterol.

21. The iRNA duplex agent of claim 18, wherein $R^L$ is
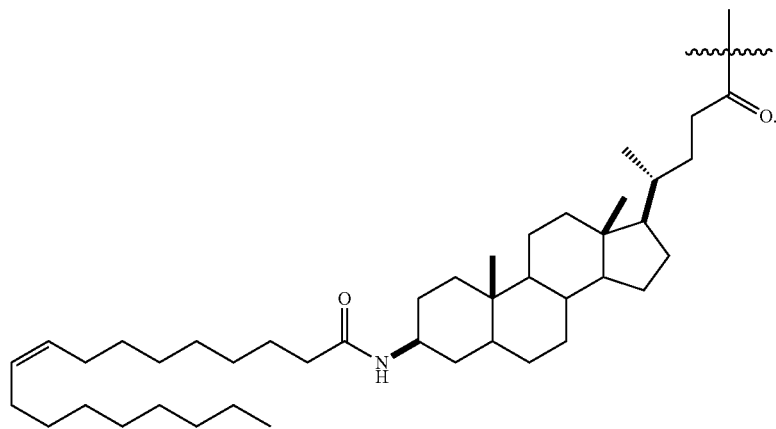
22. The iRNA duplex agent of claim 17, wherein R having the structure of formula (V):
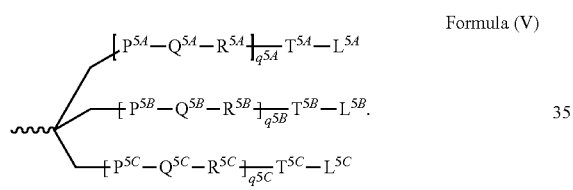
Formula (V)
23. The iRNA duplex agent of claim 22, wherein R is
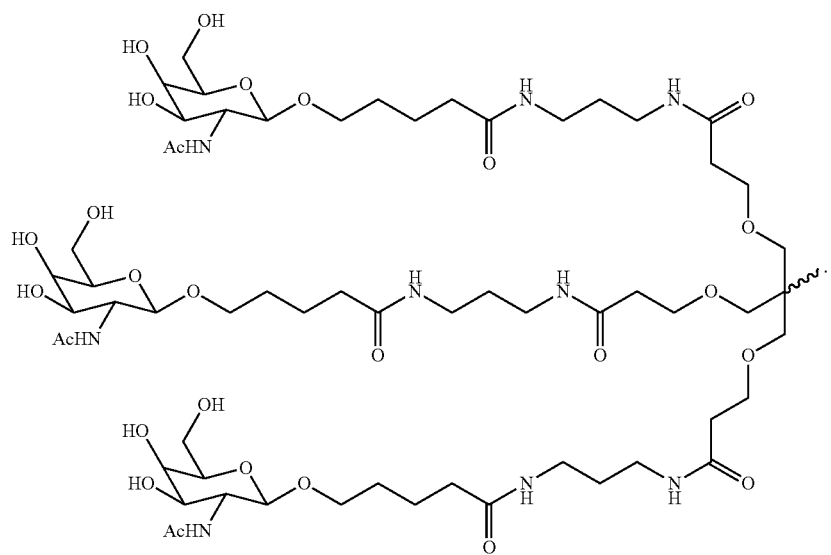 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O ; "."]

24. The iRNA duplex agent of claim 22, wherein R is
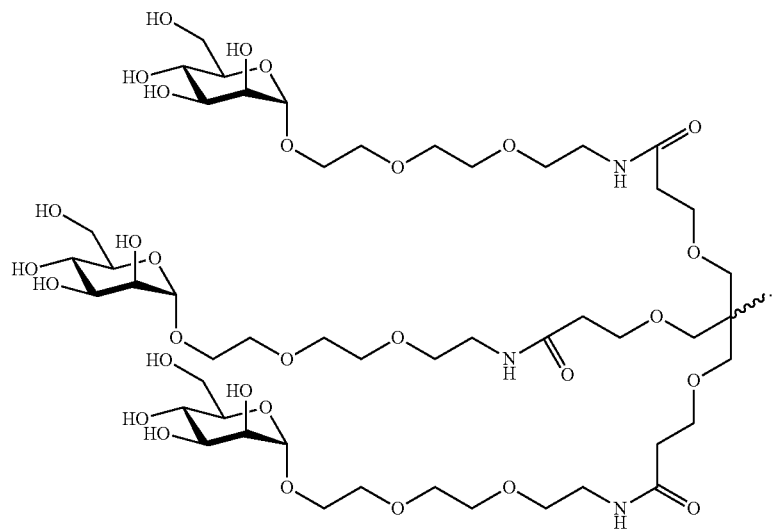
25. The iRNA duplex agent of claim 17, wherein said compound has the structure
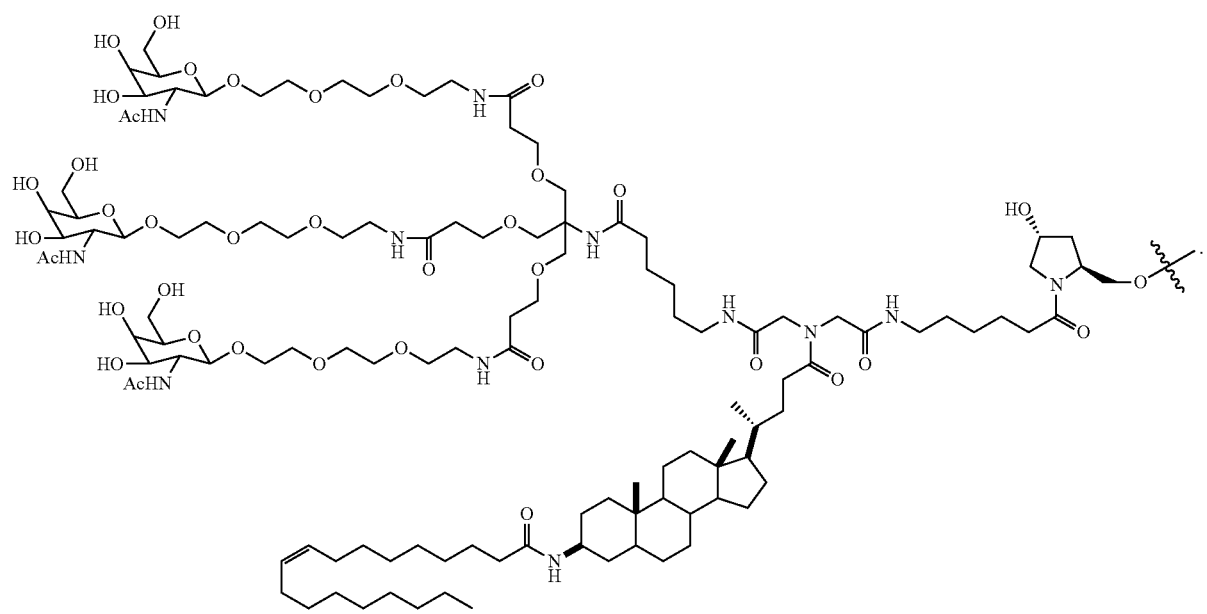

26. The iRNA duplex agent of claim 17, wherein said compound has the structure

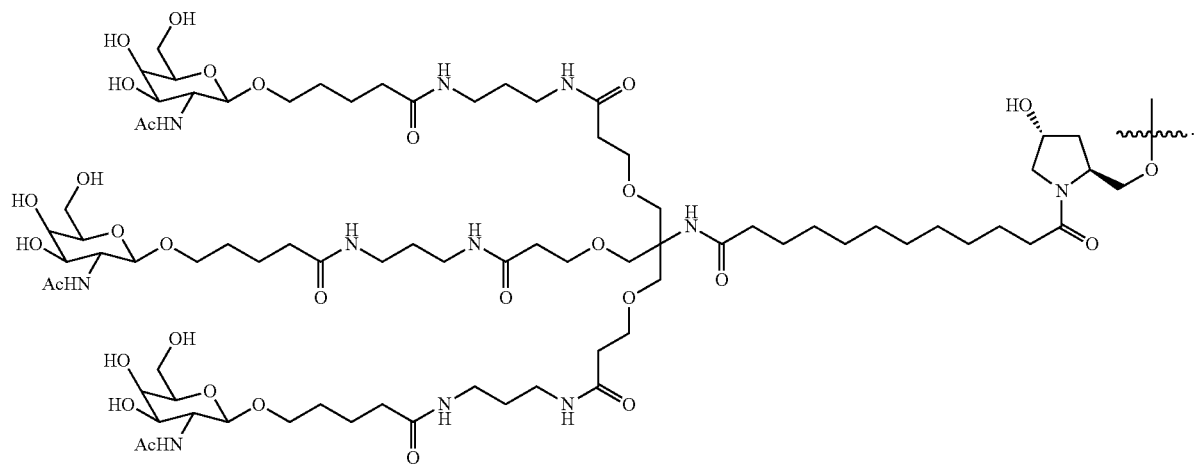 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O ; "."]

27. The iRNA duplex agent of claim 17, wherein said compound has the structure

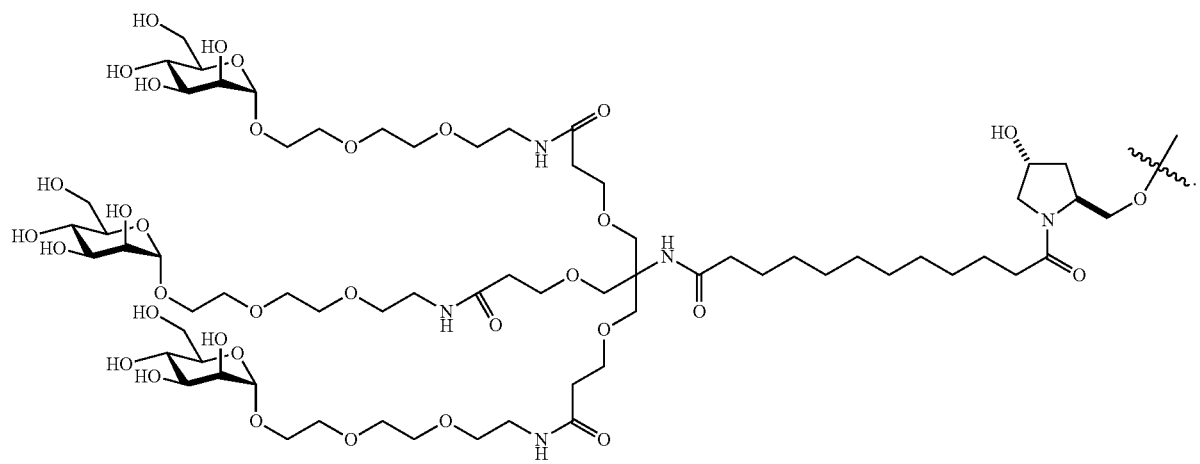

28. A method for delivering a polynucleotide to a specific target in a subject by administering an iRNA duplex agent comprising:
  (a) a sense strand, wherein said sense strand comprises
    (i) an alternating motif with at least 2 different chemically modified nucleotides; and
    (ii) one or more carbohydrate ligand; and
  (b) an antisense strand, wherein said antisense strand comprises
    (i) an alternating motif with at least 2 different chemically modified nucleotides.

29. The method of claim 28, wherein said administering step is carried out by an administration means comprising intramuscular, intrabronchial, intrapleural, intraperitoneal, intraarterial, lymphatic, intravenous, subcutaneous, cerebrospinal, or combinations thereof.

30. A method for delivering a polynucleotide to specific target of a subject, the method comprising: delivering an iRNA duplex agent according to claim 1 by subcutaneous means into the subject, such that the polynucleotide is delivered into specific target of the subject.

31. A pharmaceutical composition comprising an iRNA duplex agent of claim 1 alone or in combination with a pharmaceutically acceptable carrier or excipient.

32. The iRNA duplex agent of claim 1, wherein the carbohydrate ligand is N-Acetyl-Galactosamine (GalNAc).

33. The iRNA duplex agent of claim 1, wherein the iRNA duplex agent is capable of being delivered to specific target of a subject by a subcutaneous means.

* * * * *